US012655441B2

(12) United States Patent
Mo et al.

(10) Patent No.: US 12,655,441 B2
(45) Date of Patent: Jun. 16, 2026

(54) PPO POLYPEPTIDES TOLERANT TO PPO-INHIBITING HERBICIDES AND USE THEREOF

(71) Applicant: QINGDAO KINGAGROOT CHEMICAL COMPOUND CO., LTD., Qingdao (CN)

(72) Inventors: Sudong Mo, Qingdao (CN); Guizhi Liu, Qingdao (CN); Lei Wang, Qingdao (CN); Qiqi Hou, Qingdao (CN); Bo Chen, Qingdao (CN)

(73) Assignee: QINGDAO KINGAGROOT CHEMICAL COMPOUND CO., LTD., Qingdao (CN)

( * ) Notice: Subject to any disclaimer, the term of this patent is extended or adjusted under 35 U.S.C. 154(b) by 217 days.

(21) Appl. No.: 18/284,662

(22) PCT Filed: Mar. 25, 2022

(86) PCT No.: PCT/CN2022/082947
§ 371 (c)(1),
(2) Date: Sep. 28, 2023

(87) PCT Pub. No.: WO2022/206580
PCT Pub. Date: Oct. 6, 2022

(65) Prior Publication Data

US 2024/0368618 A1 Nov. 7, 2024

(30) Foreign Application Priority Data

Apr. 2, 2021 (CN) ......................... 202110361141.6
Feb. 15, 2022 (CN) ......................... 202210136187.2

(51) Int. Cl.
*C12N 15/82* (2006.01)
*C12N 9/02* (2006.01)
(Continued)

(52) U.S. Cl.
CPC ......... *C12N 15/8274* (2013.01); *C12N 9/001* (2013.01); *C12N 9/22* (2013.01);
(Continued)

(58) Field of Classification Search
None
See application file for complete search history.

(56) References Cited

U.S. PATENT DOCUMENTS 6,018,105 A * 1/2000 Johnson ............. C12N 15/8214
435/320.1
10,717,985 B2 * 7/2020 Sung ...................... C12N 9/001
(Continued)

FOREIGN PATENT DOCUMENTS

AU 2018200176 A1 2/2018
CN 1212724 A 3/1999
(Continued)

OTHER PUBLICATIONS

Parzych, Katherine R., and Daniel J. Klionsky. "An overview of autophagy: morphology, mechanism, and regulation." Antioxidants & redox signaling 20.3 (2014): 460-473. (Year: 2014).*
(Continued)

*Primary Examiner* — Weihua Fan
(74) *Attorney, Agent, or Firm* — Leydig, Voit & Mayer, Ltd.

(57) ABSTRACT

The present invention relates to the field of biotechnology, and specifically relates to a PPO polypeptide tolerant to PPO-inhibiting herbicides and use thereof. The said polypeptide contains the motif "LLLNYI", wherein leucine L at position 3 in the said motif is substituted with any other amino acid, or tyrosine Y at position 5 is substituted with any other amino acid. It can be used in plants, including commercial crops, to greatly improve plant resistance to PPO-inhibiting herbicides according to the herbicide resistance
(Continued)

characteristics and herbicide selectivity, so as to control weed growth economically.

20 Claims, 10 Drawing Sheets

Specification includes a Sequence Listing.

(51) Int. Cl.
*C12N 9/22* (2006.01)
*C12N 15/11* (2006.01)

(52) U.S. Cl.
CPC .......... *C12N 15/11* (2013.01); *C12N 15/8213* (2013.01); *C12Y 103/03004* (2013.01); *C12N 2310/20* (2017.05)

(56) References Cited

U.S. PATENT DOCUMENTS

| | | | | |
|---|---|---|---|---|
| 2004/0123343 | A1 | 6/2004 | La Rosa et al. | |
| 2018/0327773 | A1 * | 11/2018 | Gocal ................ | C12N 15/8274 |

FOREIGN PATENT DOCUMENTS

| | | | |
|---|---|---|---|
| CN | 1382377 | A | 12/2002 |
| CN | 103327809 | A | 9/2013 |
| CN | 107384911 | A | 11/2017 |
| WO | WO 95/34659 | A1 | 12/1995 |
| WO | WO 97/32011 | A1 | 9/1997 |
| WO | 01/68826 | A2 | 9/2001 |
| WO | WO 2012/018862 | A2 | 2/2012 |
| WO | 2013/028188 | A1 | 2/2013 |
| WO | WO 2017/217793 | A1 | 12/2017 |
| WO | 2019/106568 | A1 | 6/2019 |
| WO | 2020/251313 | A2 | 12/2020 |

OTHER PUBLICATIONS

China National Intellectual Property Administration, International Search Report and Written Opinion issued in International Patent Application No. PCT/CN2022/082947, mailed on Jun. 29, 2022.
Li et al., "Development of Protoporphyrinogen Oxidase as an Efficient Selection Marker for *Agrobacterium tumefaciens*-Mediated Transformation of Maize", *Plant Physiology*, 133: 736-747 (2003).
Zhou et al., "Progress on Protoporphyrinogen Oxidase-Inhibiting Herbicides", *Chinese Journal of Pesticide Science*, 4(1): 1-8 (2002).
"Predicted: Oryza sativa Japonica Group protoporphyrinogen oxidase, chloroplastic-like (LOC4327918), mRNA", NCBI Reference Sequence: XM_015770568.2, 2 pages (2018).
Hao et al., "Protoporphyrinogen Oxidase Inhibitor: An Ideal Target for Herbicide Discovery", Chimia, 65(12): 961-969 (2011).
European Patent Office, extended European Search Report issued in corresponding European Application No. 22778763.7, dated Jul. 1, 2025.
Japanese Patent Office, First Office Action issued in corresponding Japanese Patent Application No. 2023-560280, mailed: May 20, 2025.
Intellectual Property Organization of Pakistan, First Office Action issued in corresponding Pakistani Patent Application No. 234/2022, dated Jul. 29, 2025.
Watanabe, N. et al., Dual Targeting of Spinach Protoporphyrinogen Oxidase II to Mitochondria and Chloroplasts by Alternative Use of Two In-frame Initiation Codons, The Journal Of Biological Chemistry, vol. 276, No. 23, Issue of June 8, p. 20474-20481, 2001.

* cited by examiner

| | |
|---|---|
| OsPPO1 | LGTIYSSSLFPNRAPAGRVLLLNYIGGSTNTGIVSKTESELVEAVDRDLRKMLINPKAVD |
| ZmPPO1 | LGTIYSSSLFPNRAPDGRVLLLNYIGGATNTGIVSKTESELVEAVDRDLRKMLINSTAVD |
| AtPPO1 | LGTIYSSSLFPNRAPPGRILLLNYIGGSTNTGILSKSEGELVEAVDRDLRKMLIKPNSTD |
| GmPPO1 | LGTIYSSSLFPNRAPPGRVLLLNYIGGATNTGILSKTDSELVETVDRDLRKILINPNAQD |
| NtPPO1 | LGTIYSSSLFPNRAPKGRVLLLNYIGGAKNPEILSKTESQLVEVVDRDLRKMLIKPKAQD |
| SbPPO1 | LGTIYSSSLFPNRAPAGRVLLLNYIGGATNTGIVSKTESELVEAVDRDLRKMLINSTAVD |
| SlPPO1 | LGTIYSSSLFPNRAPNGRVLLLNYIGGATNTEIVSKTESQLVEAVDRDLRKMLIKPKAQD |
| HvPPO1 | LGTIYSSSLFPNRAPAGRVLLLNYIGGSTNTGIVSKTESDLVEAVDRDLRKMLINPRAAD |
| BnPPO1-A10 | LGTIYSSSLFPNRAPPGRVLLLNYIGGATNTGILSKSEGELVEAVDRDLRKMLIKPSSTD |
| BnPPO1-C5 | LGTIYSSSLFPNRAPPGRVLLLNYIGGATNTGILSKSEGELVEAVDRDLRKMLIKPSSTD |
| AhPPO1-A | LGTIYSSSLFPNRAPDGRVLLLNYIGGATNPGILSKTDSELVEAVDRDLRKMLINPNAGD |
| AhPPO1-B | LGTIYSSSLFPNRAPDGRVLLLNYIGGATNPGILSKTDSELVEAVDRDLRKMLINPNAGD |
| TaPPO1-A | LGTIYSSSLFPNRAPAGRVLLLNYIGGSTNTGIVSKTESDLVEAVDRDLRKMLINPRAAD |
| TaPPO1-B | LGTIYSSSLFPNRAPAGRVLLLNYIGGSTNTGIVSKTESDLVGAVDRDLRKMLINPRAAD |
| TaPPO1-D | LGTIYSSSLFPNRAPAGRVLLLNYIGGSTNTGIVSKTESDLVEAVDSDLRKMLINPRAAD |
| BoPPO1 | LGTIYSSSLFPNRAPPGRVLLLNYIGGATNTGILSKSEGELVEAVDRDLRKMLIMPSSTD |
| SiPPO1 | LGTIYSSSLFPNRAPAGRVLLLNYIGGATNTGIVSKSASELVEAVDRDLRKMLINPSAVD |
| RsPPO1 | LGTIYSSSLFPNRAPPGRVLLLNYIGGTTNTGILSKSEGELVEAVDRDLRKMLIKPSSTD |
| StPPO1 | LGTIYSSSLFPNRAPNGRVLLLNYIGGATNTEIVSKTESQLVEAVDRDLRKMLIKPKAQD |
| GhPPO1 | LGTIYSSSLFPNRAPSGRVLLLNYIGGATNTGILSKTEGELVEAVDRDLRKMLINPNAKD |
| DcPPO1 | LGTIYSSSLFPNRAPSGRVLLLNYIGGATNTGIVSKTEDELVEAVDRDLRKMLINPKAED |
| MePPO1 | LGTIYSSSLFPNRAPDGRILLLNYIGGATNPGILSKMDNELVEAVDRDLRRMLIKPNAKD |
| CaPPO1 | LGTIYSSSLFPNRAPNGRVLLLNYIGGATNTEILSKTESQLVEAVDRDLRKMLIKPKAQD |
| CmPPO1 | LGTIYSSSLFPNRAPDGRVLLLNYIGGSTNTEILAKTESELVEAVDRDLRKIIINTNAED |
| CsPPO1 | LGTIYSSSLFPNRAPDGRVLLLNYIGGATNTGILSQTESELIEVVDRDLRKILINPNAED |
| LsPPO1 | LGTIYSSSLFPNRAPPGRVLLLNYIGGATNPEILSKTEGQIVDAVDRDLRKMLIRRDAGD |
| SiPPO1 | LGTIYSSSLFPNRAPPGRVLLLNYIGGATNPGITLKTKSQLVDSVDRDLRKMLINTNAPD |
| HaPPO1 | LGTIYSSSLFPNRAPPGRVLLLNYIGGATNPGILSKTESQLVEAVDRDLRTMLINPKAGE |
| MaPPO1 | LGTIYSSSLFPDRAPTGRVLLLNYIGGATNPGILSKTEDELVEAVDRDLRKVLIRPNAED |
| VuPPO1 | LGTIYSSSLFPNRAPPGRVLLLNYIGGATNTGILQKTDSELVEAVDRDLRKMLINPNAQD |
| FaPPO1 | LGTIYSSSLFPNRAPAGRVLLLNYIGGATNPGILSQTESELVETVHQDLKKVLIKPNAKD |
| MdPPO1 | LGTIYSSSLFPNRAPPGRVLLLNYIGGATNPGILSETESKLVEAVDQDLRKVLLNHNAKE |
| PpPPO1 | LGTIYSSSLFPNRAPPGRVLLLNYIGGATNPGILSKKESELVEAVDQDLRNVLLNRNAKD |
| PpPPO1 | LGTIYSSSLFPNRAPPGRVLLLNYIGGATNPGILSKKESELVEAVDQDLRNVLLNRNAKD |
| PaPPO1 | LGTIYSSSLFPNRAPPGRVLLLNYIGGATNPGILSKKESELVEAVDRDLRNVLLNRNAKD |
| VvPPO1 | LGTIYSSSLFPNRAPPGRILLLNYIGGATNPGILSKTESELVEAVDRDLRKMLINPNAKD |
| CpPPO1 | LGTIYSSSLFPNRAPAGRVLLLNYIGGATNRGILSKTEAKLVEVVDRDLRKMLINPSAKD |
| MsPPO1 | LGTIYSSSLFPNRAPPGRVLLLNYIGGATNSGILSKTEGELVEAVDRDLRKILINPNAQD |

Wild-type Jinjing 818 T0-generation (L423S/Y425I replacement)

0nM Compound A 50nM Compound A 2μM Compound A wild-type pHSE-GmPPO1 WT pHSE-GmPPO1 L430S/Y432I 0nM Compound A 50nM Compound A 2μM Compound A wild-type pHSE-BnPPO1-C5 WT pHSE-BnPPO1-C5 L424S/Y426I 0nM Compound A
50nM Compound A
2μM Compound A wild-type
pHSE-ZmPPO1 WT
pHSE-ZmPPO1 L424W/Y426L 0nM Compound A
50nM Compound A
2μM Compound A wild-type
pHSE-OsPPO1 WT
pHSE-OsPPO1 L423S/Y425I 0nM flumioxazin
10nM flumioxazin
1μM flumioxazin Wild-type
pHSE-OsPPO1 WT
pHSE-OsPPO1 L423S/Y425I

SEQUENCE LISTING

```
<160> NUMBER OF SEQ ID NOS: 66

<210> SEQ ID NO 1
<211> LENGTH: 536
<212> TYPE: PRT
<213> ORGANISM: Artificial sequence
<220> FEATURE:
<223> OTHER INFORMATION: Amino-acid sequence of PPO1 from wild-type rice
      (OsPPO1 WT)

<400> SEQUENCE: 1

Met Ala Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg Arg
            20                  25                  30

Gly His Val Arg Cys Ala Val Ala Ser Gly Ala Ala Glu Ala Pro Ala
        35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300
```

```
Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Leu Asn Tyr Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535


<210> SEQ ID NO 2
<211> LENGTH: 537
<212> TYPE: PRT
<213> ORGANISM: Artificial sequence
<220> FEATURE:
<223> OTHER INFORMATION: Amino-acid sequence of PPO1 from wild-type corn
      (ZmPPO1 WT)

<400> SEQUENCE: 2

Met Val Ala Ala Thr Ala Thr Ala Thr Ala Met Ala Thr Ala Ala Ser
1               5                   10                  15

Pro Leu Leu Asn Gly Thr Arg Ile Pro Ala Arg Leu Arg His Arg Gly
            20                  25                  30

Leu Ser Val Arg Cys Ala Ala Val Ala Gly Gly Ala Ala Glu Ala Pro
        35                  40                  45

Ala Ser Thr Gly Ala Arg Leu Ser Ala Asp Cys Val Val Val Gly Gly
    50                  55                  60

Gly Ile Ser Gly Leu Cys Thr Ala Gln Ala Leu Ala Thr Arg His Gly
65                  70                  75                  80

Val Gly Asp Val Leu Val Thr Glu Ala Arg Ala Arg Pro Gly Gly Asn
                85                  90                  95

Ile Thr Thr Val Glu Arg Pro Glu Glu Gly Tyr Leu Trp Glu Glu Gly
            100                 105                 110

Pro Asn Ser Phe Gln Pro Ser Asp Pro Val Leu Thr Met Ala Val Asp
        115                 120                 125
```

-continued

```
Ser Gly Leu Lys Asp Asp Leu Val Phe Gly Asp Pro Asn Ala Pro Arg
    130                 135                 140

Phe Val Leu Trp Glu Gly Lys Leu Arg Pro Val Pro Ser Lys Pro Ala
145                 150                 155                 160

Asp Leu Pro Phe Phe Asp Leu Met Ser Ile Pro Gly Lys Leu Arg Ala
                165                 170                 175

Gly Leu Gly Ala Leu Gly Ile Arg Pro Pro Pro Pro Gly Arg Glu Glu
            180                 185                 190

Ser Val Glu Glu Phe Val Arg Arg Asn Leu Gly Ala Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Arg Leu Glu Glu
225                 230                 235                 240

Thr Gly Gly Ser Ile Ile Gly Gly Thr Ile Lys Thr Ile Gln Glu Arg
                245                 250                 255

Ser Lys Asn Pro Lys Pro Pro Arg Asp Ala Arg Leu Pro Lys Pro Lys
            260                 265                 270

Gly Gln Thr Val Ala Ser Phe Arg Lys Gly Leu Ala Met Leu Pro Asn
        275                 280                 285

Ala Ile Thr Ser Ser Leu Gly Ser Lys Val Lys Leu Leu Trp Lys Leu
    290                 295                 300

Thr Ser Ile Thr Lys Ser Asp Asp Lys Gly Tyr Val Leu Glu Tyr Glu
305                 310                 315                 320

Thr Pro Glu Gly Val Val Ser Val Gln Ala Lys Ser Val Ile Met Thr
                325                 330                 335

Ile Pro Ser Tyr Val Ala Ser Asn Ile Leu Arg Pro Leu Ser Ser Asp
            340                 345                 350

Ala Ala Asp Ala Leu Ser Arg Phe Tyr Tyr Pro Pro Val Ala Ala Val
        355                 360                 365

Thr Val Ser Tyr Pro Lys Glu Ala Ile Arg Lys Glu Cys Leu Ile Asp
    370                 375                 380

Gly Glu Leu Gln Gly Phe Gly Gln Leu His Pro Arg Ser Gln Gly Val
385                 390                 395                 400

Glu Thr Leu Gly Thr Ile Tyr Ser Ser Ser Leu Phe Pro Asn Arg Ala
                405                 410                 415

Pro Asp Gly Arg Val Leu Leu Leu Asn Tyr Ile Gly Gly Ala Thr Asn
            420                 425                 430

Thr Gly Ile Val Ser Lys Thr Glu Ser Glu Leu Val Glu Ala Val Asp
        435                 440                 445

Arg Asp Leu Arg Lys Met Leu Ile Asn Ser Thr Ala Val Asp Pro Leu
    450                 455                 460

Val Leu Gly Val Arg Val Trp Pro Gln Ala Ile Pro Gln Phe Leu Val
465                 470                 475                 480

Gly His Leu Asp Leu Leu Glu Ala Ala Lys Ala Ala Leu Asp Arg Gly
                485                 490                 495

Gly Tyr Asp Gly Leu Phe Leu Gly Gly Asn Tyr Val Ala Gly Val Ala
            500                 505                 510

Leu Gly Arg Cys Val Glu Gly Ala Tyr Glu Ser Ala Ser Gln Ile Ser
        515                 520                 525

Asp Phe Leu Thr Lys Tyr Ala Tyr Lys
    530                 535
```

-continued

<210> SEQ ID NO 3
<211> LENGTH: 537
<212> TYPE: PRT
<213> ORGANISM: Artificial sequence
<220> FEATURE:
<223> OTHER INFORMATION: Amino-acid sequence of PPO1 wild-type from oilseed rape (BnPPO1-C5)

<400> SEQUENCE: 3

```
Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Pro Asn Leu Arg Cys
            20                  25                  30

Ser Val Ser Gly Gly Ser Val Val Gly Gly Ser Ser Thr Ile Glu Gly
        35                  40                  45

Gly Arg Gly Gly Lys Thr Val Ala Ala Asp Cys Val Ile Val Gly Gly
    50                  55                  60

Gly Ile Ser Gly Leu Cys Ile Ala Gln Ala Leu Val Thr Lys His Pro
65                  70                  75                  80

Asp Ala Ala Lys Ser Val Met Val Thr Glu Ala Lys Asp Arg Val Gly
                85                  90                  95

Gly Asn Ile Ile Thr Arg Glu Glu Gln Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Ile Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ala
    210                 215                 220

Lys Leu Ser Met Lys Ala Ala Phe Gly Lys Val Trp Lys Leu Glu Glu
225                 230                 235                 240

Asn Gly Gly Ser Ile Ile Gly Gly Ala Phe Lys Ala Ile Gln Ala Arg
                245                 250                 255

Asn Lys Ala Pro Lys Thr Thr Arg Asp Pro Arg Leu Pro Lys Pro Lys
            260                 265                 270

Gly Gln Thr Val Gly Ser Phe Arg Lys Gly Leu Thr Met Leu Pro Asp
        275                 280                 285

Ala Ile Ser Ala Arg Leu Gly Asp Lys Val Lys Val Ser Trp Lys Leu
    290                 295                 300

Ser Ser Ile Ser Lys Leu Pro Ser Gly Gly Tyr Ser Leu Thr Tyr Glu
305                 310                 315                 320

Thr Pro Glu Gly Ile Val Thr Val Gln Ser Lys Ser Val Val Met Thr
                325                 330                 335

Val Pro Ser His Val Ala Ser Ser Leu Leu Arg Pro Leu Ser Asp Ser
            340                 345                 350

Ala Ala Glu Ala Leu Ser Lys Leu Tyr Tyr Pro Pro Val Ala Ala Val
        355                 360                 365
```

```
Ser Ile Ser Tyr Pro Lys Glu Ala Ile Arg Ser Glu Cys Leu Ile Asp
    370                 375                 380

Gly Glu Leu Lys Gly Phe Gly Gln Leu His Pro Arg Thr Gln Lys Val
385                 390                 395                 400

Glu Thr Leu Gly Thr Ile Tyr Ser Ser Ser Leu Phe Pro Asn Arg Ala
                405                 410                 415

Pro Pro Gly Arg Val Leu Leu Leu Asn Tyr Ile Gly Gly Ala Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Ser Ser Thr Asp Pro Leu
    450                 455                 460

Val Leu Gly Val Lys Val Trp Pro Gln Ala Ile Pro Gln Phe Leu Ile
465                 470                 475                 480

Gly His Ile Asp Leu Val Asp Ala Ala Lys Ala Ser Leu Ser Ser Ser
                485                 490                 495

Gly His Glu Gly Leu Phe Leu Gly Gly Asn Tyr Val Ala Gly Val Ala
            500                 505                 510

Leu Gly Arg Cys Val Glu Gly Ala Tyr Glu Thr Ala Thr Gln Val Asn
        515                 520                 525

Asp Phe Met Ser Arg Tyr Ala Tyr Lys
    530                 535
```

<210> SEQ ID NO 4
<211> LENGTH: 536
<212> TYPE: PRT
<213> ORGANISM: Artificial sequence
<220> FEATURE:
<223> OTHER INFORMATION: Amino-acid sequence of PPO1 from wild-type oilseed rape (BnPPO1-A10)

<400> SEQUENCE: 4

```
Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Leu Asn Leu Arg Cys
            20                  25                  30

Ser Val Ser Gly Gly Ser Val Val Gly Ser Ser Thr Ile Glu Gly Gly
        35                  40                  45

Gly Gly Gly Lys Thr Val Thr Ala Asp Cys Val Ile Val Gly Gly Gly
    50                  55                  60

Ile Ser Gly Leu Cys Ile Ala Gln Ala Leu Val Thr Lys His Pro Asp
65                  70                  75                  80

Ala Ala Lys Asn Val Met Val Thr Glu Ala Lys Asp Arg Val Gly Gly
                85                  90                  95

Asn Ile Ile Thr Arg Glu Glu Gln Gly Phe Leu Trp Glu Glu Gly Pro
            100                 105                 110

Asn Ser Phe Gln Pro Ser Asp Pro Met Leu Thr Met Val Val Asp Ser
        115                 120                 125

Gly Leu Lys Asp Asp Leu Val Leu Gly Asp Pro Thr Ala Pro Arg Phe
    130                 135                 140

Val Leu Trp Asn Gly Lys Leu Arg Pro Val Pro Ser Lys Leu Thr Asp
145                 150                 155                 160

Leu Pro Phe Phe Asp Leu Met Ser Ile Gly Gly Lys Ile Arg Ala Gly
                165                 170                 175

Phe Gly Ala Ile Gly Ile Arg Pro Ser Pro Pro Gly Arg Glu Glu Ser
```

-continued

```
            180                 185                 190

Val Glu Glu Phe Val Arg Arg Asn Leu Gly Asp Glu Val Phe Glu Arg
        195                 200                 205

Leu Ile Glu Pro Phe Cys Ser Gly Val Tyr Ala Gly Asp Pro Ala Lys
    210                 215                 220

Leu Ser Met Lys Ala Ala Phe Gly Lys Val Trp Lys Leu Glu Glu Asn
225                 230                 235                 240

Gly Gly Ser Ile Ile Gly Gly Ala Phe Lys Ala Ile Gln Ala Lys Asn
                245                 250                 255

Lys Ala Pro Lys Thr Thr Arg Asp Pro Arg Leu Pro Lys Pro Lys Gly
            260                 265                 270

Gln Thr Val Gly Ser Phe Arg Lys Gly Leu Thr Met Leu Pro Glu Ala
        275                 280                 285

Ile Ser Ala Arg Leu Gly Asp Lys Val Lys Val Ser Trp Lys Leu Ser
    290                 295                 300

Ser Ile Thr Lys Leu Ala Ser Gly Glu Tyr Ser Leu Thr Tyr Glu Thr
305                 310                 315                 320

Pro Glu Gly Ile Val Thr Val Gln Ser Lys Ser Val Val Met Thr Val
                325                 330                 335

Pro Ser His Val Ala Ser Ser Leu Leu Arg Pro Leu Ser Asp Ser Ala
            340                 345                 350

Ala Glu Ala Leu Ser Lys Leu Tyr Tyr Pro Pro Val Ala Ala Val Ser
        355                 360                 365

Ile Ser Tyr Ala Lys Glu Ala Ile Arg Ser Glu Cys Leu Ile Asp Gly
    370                 375                 380

Glu Leu Lys Gly Phe Gly Gln Leu His Pro Arg Thr Gln Lys Val Glu
385                 390                 395                 400

Thr Leu Gly Thr Ile Tyr Ser Ser Ser Leu Phe Pro Asn Arg Ala Pro
                405                 410                 415

Pro Gly Arg Val Leu Leu Leu Asn Tyr Ile Gly Gly Ala Thr Asn Thr
            420                 425                 430

Gly Ile Leu Ser Lys Ser Glu Gly Glu Leu Val Glu Ala Val Asp Arg
        435                 440                 445

Asp Leu Arg Lys Met Leu Ile Lys Pro Ser Ser Thr Asp Pro Leu Val
    450                 455                 460

Leu Gly Val Lys Leu Trp Pro Gln Ala Ile Pro Gln Phe Leu Ile Gly
465                 470                 475                 480

His Ile Asp Leu Val Asp Ala Ala Lys Ala Ser Leu Ser Ser Ser Gly
                485                 490                 495

His Glu Gly Leu Phe Leu Gly Gly Asn Tyr Val Ala Gly Val Ala Leu
            500                 505                 510

Gly Arg Cys Val Glu Gly Ala Tyr Glu Thr Ala Thr Gln Val Asn Asp
        515                 520                 525

Phe Met Ser Arg Tyr Ala Tyr Lys
    530                 535
```

<210> SEQ ID NO 5
<211> LENGTH: 558
<212> TYPE: PRT
<213> ORGANISM: Artificial sequence
<220> FEATURE:
<223> OTHER INFORMATION: Amino-acid sequence of PPO1 from wild-type peanut (AhPPO1-A)

<400> SEQUENCE: 5

-continued

```
Met Pro Ala Met Leu Thr Leu Pro Asn Asp Thr Val Phe Leu Gln Asn
1               5                   10                  15

Thr Met His Ser Pro Thr Ser Ser Phe Ser Pro His Ser Pro Leu Ile
            20                  25                  30

Ile Pro Phe Pro Ser Pro Cys Arg His Pro Ser Thr Thr Lys Phe Pro
        35                  40                  45

Leu Ile Arg Cys Ser Leu Ala Gly Glu Ser Ser Thr Ala Ser Pro Ala
    50                  55                  60

Lys Pro Ala Ala Leu Pro Arg Ser Ala Val Gly Ala Ser Val Asp Cys
65                  70                  75                  80

Val Val Val Gly Gly Gly Ile Ser Gly Leu Cys Ile Ala Gln Ala Leu
                85                  90                  95

Ser Thr Lys His Ala Lys Ala Ala Ala Asn Val Val Val Thr Glu Ala
            100                 105                 110

Arg Asp Arg Val Gly Gly Asn Ile Thr Thr Ile Glu Arg Asp Gly Tyr
        115                 120                 125

Leu Trp Glu Glu Gly Pro Asn Ser Phe Gln Pro Ser Asp Pro Met Leu
    130                 135                 140

Thr Met Val Val Asp Ser Gly Leu Lys Asp Glu Leu Val Leu Gly Asp
145                 150                 155                 160

Pro Asn Ala Pro Arg Phe Val Leu Trp Asn Gly Glu Leu Arg Pro Val
                165                 170                 175

Pro Gly Lys Pro Thr Asp Leu Pro Phe Phe Asp Leu Met Ser Phe Gly
            180                 185                 190

Gly Lys Leu Arg Ala Gly Phe Gly Ala Leu Gly Ile Arg Pro Pro Pro
        195                 200                 205

Pro Gly His Glu Glu Ser Val Glu Glu Phe Val Arg Arg Asn Leu Gly
    210                 215                 220

Asp Glu Val Phe Glu Arg Leu Ile Glu Pro Phe Cys Ser Gly Val Tyr
225                 230                 235                 240

Ala Gly Asp Pro Ser Lys Leu Ser Met Lys Ala Ala Phe Gly Lys Val
                245                 250                 255

Trp Arg Leu Glu Gln Asn Gly Gly Ser Ile Ile Gly Gly Thr Phe Lys
            260                 265                 270

Ala Ile Gln Glu Arg Lys Ser Thr Ser Lys Pro Pro Arg Asp Pro Arg
        275                 280                 285

Leu Pro Thr Pro Lys Gly Gln Thr Val Gly Ser Phe Arg Lys Gly Leu
    290                 295                 300

Thr Met Leu Pro Glu Ala Ile Ser Ala Lys Leu Gly Asn Lys Val Lys
305                 310                 315                 320

Leu Ser Trp Lys Leu Leu Gly Ile Ser Lys Leu Asp Ser Gly Glu Tyr
                325                 330                 335

Ser Leu Thr Tyr Asp Thr Pro Glu Gly Val Val Ser Leu Gln Thr Lys
            340                 345                 350

Ser Val Val Met Thr Ile Pro Ser His Val Ala Ser Thr Leu Leu Arg
        355                 360                 365

Ser Ile Ser Asp Ala Ala Ala Asp Ala Leu Ser Lys Phe Tyr Tyr Pro
    370                 375                 380

Pro Val Ala Ala Val Ser Val Ser Tyr Pro Lys Glu Ala Ile Arg Ser
385                 390                 395                 400

Glu Cys Leu Ile Asp Gly Glu Leu Lys Gly Phe Gly Gln Leu His Pro
                405                 410                 415

Arg Thr Gln Gly Val Glu Thr Leu Gly Thr Ile Tyr Ser Ser Ser Leu
```

```
            420                 425                 430

Phe Pro Asn Arg Ala Pro Asp Gly Arg Val Leu Leu Leu Asn Tyr Ile
        435                 440                 445

Gly Gly Ala Thr Asn Pro Gly Ile Leu Ser Lys Thr Asp Ser Glu Leu
    450                 455                 460

Val Glu Ala Val Asp Arg Asp Leu Arg Lys Met Leu Ile Asn Pro Asn
465                 470                 475                 480

Ala Gly Asp Pro Phe Ala Leu Gly Val Arg Val Trp Pro Gln Ala Ile
                485                 490                 495

Pro Gln Phe Leu Val Gly His Leu Asp Leu Leu Asp Ile Ala Lys Ser
            500                 505                 510

Ser Leu Lys Asn Thr Gly Phe Glu Gly Leu Phe Leu Gly Gly Asn Tyr
        515                 520                 525

Val Ser Gly Val Ala Leu Gly Arg Cys Val Glu Gly Ala Tyr Glu Ile
    530                 535                 540

Ala Ala Glu Val Asp Asp Phe Leu Ala Gln Lys Val Tyr Lys
545                 550                 555


<210> SEQ ID NO 6
<211> LENGTH: 552
<212> TYPE: PRT
<213> ORGANISM: Artificial sequence
<220> FEATURE:
<223> OTHER INFORMATION: Amino-acid sequence of PPO1 from wild-type
      peanut (AhPPO1-B)

<400> SEQUENCE: 6

Met Ser Ala Met Leu Thr Leu Pro Asn Asp Thr Val Phe Leu Gln Asn
1               5                   10                  15

Thr Met His Ser Pro Thr Ser Ser Phe Ser Pro His Ser Pro Leu Ile
            20                  25                  30

Ile Pro Phe Pro Ser Pro Cys Arg His Pro Ser Thr Thr Lys Phe Pro
        35                  40                  45

Leu Ile Arg Cys Ser Leu Ala Gly Glu Ser Ser Thr Ala Ser Leu Pro
    50                  55                  60

Arg Ser Ala Val Gly Ala Ser Val Asp Cys Val Val Val Gly Gly Gly
65                  70                  75                  80

Ile Ser Gly Leu Cys Ile Ala Gln Ala Leu Ser Thr Lys His Ala Lys
                85                  90                  95

Ala Ala Ala Asn Val Val Val Thr Glu Ala Arg Asp Arg Val Gly Gly
            100                 105                 110

Asn Ile Thr Thr Val Glu Arg Asp Gly Tyr Leu Trp Glu Glu Gly Pro
        115                 120                 125

Asn Ser Phe Gln Pro Ser Asp Pro Met Leu Thr Met Val Val Asp Ser
    130                 135                 140

Gly Leu Lys Asp Glu Leu Val Leu Gly Asp Pro Asn Ala Pro Arg Phe
145                 150                 155                 160

Val Leu Trp Asn Gly Arg Leu Arg Pro Val Pro Gly Lys Pro Thr Asp
                165                 170                 175

Leu Pro Phe Phe Asp Leu Met Ser Phe Gly Gly Lys Leu Arg Ala Gly
            180                 185                 190

Phe Gly Ala Leu Gly Ile Arg Pro Pro Pro Pro Gly His Glu Glu Ser
        195                 200                 205

Val Glu Glu Phe Val Arg Arg Asn Leu Gly Asp Glu Val Phe Glu Arg
    210                 215                 220
```

-continued

```
Leu Ile Glu Pro Phe Cys Ser Gly Val Tyr Ala Gly Asp Pro Ser Lys
225                 230                 235                 240

Leu Ser Met Lys Ala Ala Phe Gly Lys Val Trp Arg Leu Glu Gln Asn
                245                 250                 255

Gly Gly Ser Ile Ile Gly Gly Thr Phe Lys Ala Ile Gln Glu Arg Lys
            260                 265                 270

Ser Thr Ser Lys Pro Pro Arg Asp Pro Arg Leu Pro Thr Pro Lys Gly
        275                 280                 285

Gln Thr Val Gly Ser Phe Arg Lys Gly Leu Ile Met Leu Pro Glu Ala
    290                 295                 300

Ile Ser Ala Lys Leu Gly Asn Lys Val Lys Leu Ser Trp Lys Leu Leu
305                 310                 315                 320

Gly Ile Ser Lys Leu Asp Ser Gly Glu Tyr Ser Leu Thr Tyr Asp Thr
                325                 330                 335

Pro Glu Gly Val Val Ser Leu Gln Thr Lys Ser Val Val Met Thr Ile
            340                 345                 350

Pro Ser His Val Ala Ser Thr Leu Leu Arg Ser Ile Ser Glu Thr Ala
        355                 360                 365

Ala Asp Ala Leu Ser Lys Phe Tyr Tyr Pro Pro Val Ala Ala Val Ser
    370                 375                 380

Val Ser Tyr Pro Lys Glu Ala Ile Arg Ser Glu Cys Leu Ile Asp Gly
385                 390                 395                 400

Glu Leu Lys Gly Phe Gly Gln Leu His Pro Arg Thr Gln Gly Val Glu
                405                 410                 415

Thr Leu Gly Thr Ile Tyr Ser Ser Ser Leu Phe Pro Asn Arg Ala Pro
            420                 425                 430

Asp Gly Arg Val Leu Leu Leu Asn Tyr Ile Gly Gly Ala Thr Asn Pro
        435                 440                 445

Gly Ile Leu Ser Lys Thr Asp Ser Glu Leu Val Glu Ala Val Asp Arg
    450                 455                 460

Asp Leu Arg Lys Met Leu Ile Asn Pro Asn Ala Gly Asp Pro Phe Ala
465                 470                 475                 480

Leu Gly Val Arg Val Trp Pro Gln Ala Ile Pro Gln Phe Leu Val Gly
                485                 490                 495

His Leu Asp Leu Leu Asp Ile Ala Lys Ser Ser Leu Lys Asn Thr Gly
            500                 505                 510

Phe Glu Gly Leu Phe Leu Gly Gly Asn Tyr Val Ser Gly Val Ala Leu
        515                 520                 525

Gly Arg Cys Val Glu Gly Ala Tyr Glu Ile Ala Ala Glu Val Asp Asp
    530                 535                 540

Phe Leu Ala Gln Lys Val Tyr Lys
545                 550
```

<210> SEQ ID NO 7
<211> LENGTH: 543
<212> TYPE: PRT
<213> ORGANISM: Artificial sequence
<220> FEATURE:
<223> OTHER INFORMATION: Amino-acid sequence of PPO1 from wild-type soybean (GmPPO1)

<400> SEQUENCE: 7

```
Met Val Ser Val Phe Asn Glu Ile Leu Phe Pro Pro Asn Gln Thr Leu
1               5                   10                  15

Leu Arg Pro Ser Leu His Ser Pro Thr Ser Phe Phe Thr Ser Pro Thr
            20                  25                  30
```

```
Arg Lys Phe Pro Arg Ser Arg Pro Asn Pro Ile Leu Arg Cys Ser Ile
        35                  40                  45

Ala Glu Glu Ser Thr Ala Ser Pro Pro Lys Thr Arg Asp Ser Ala Pro
    50                  55                  60

Val Asp Cys Val Val Val Gly Gly Gly Val Ser Gly Leu Cys Ile Ala
65                  70                  75                  80

Gln Ala Leu Ala Thr Lys His Ala Asn Ala Asn Val Val Val Thr Glu
                85                  90                  95

Ala Arg Asp Arg Val Gly Gly Asn Ile Thr Thr Met Glu Arg Asp Gly
            100                 105                 110

Tyr Leu Trp Glu Glu Gly Pro Asn Ser Phe Gln Pro Ser Asp Pro Met
        115                 120                 125

Leu Thr Met Val Val Asp Ser Gly Leu Lys Asp Glu Leu Val Leu Gly
    130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
                165                 170                 175

Gly Gly Lys Ile Arg Ala Gly Phe Gly Ala Leu Gly Ile Arg Pro Pro
            180                 185                 190

Pro Pro Gly His Glu Glu Ser Val Glu Glu Phe Val Arg Arg Asn Leu
        195                 200                 205

Gly Asp Glu Val Phe Glu Arg Leu Ile Glu Pro Phe Cys Ser Gly Val
    210                 215                 220

Tyr Ala Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
                245                 250                 255

Lys Ala Ile Gln Glu Arg Asn Gly Ala Ser Lys Pro Pro Arg Asp Pro
            260                 265                 270

Arg Leu Pro Lys Pro Lys Gly Gln Thr Val Gly Ser Phe Arg Lys Gly
        275                 280                 285

Leu Thr Met Leu Pro Asp Ala Ile Ser Ala Arg Leu Gly Asn Lys Val
    290                 295                 300

Lys Leu Ser Trp Lys Leu Ser Ser Ile Ser Lys Leu Asp Ser Gly Glu
305                 310                 315                 320

Tyr Ser Leu Thr Tyr Glu Thr Pro Glu Gly Val Val Ser Leu Gln Cys
                325                 330                 335

Lys Thr Val Val Leu Thr Ile Pro Ser Tyr Val Ala Ser Thr Leu Leu
            340                 345                 350

Arg Pro Leu Ser Ala Ala Ala Ala Asp Ala Leu Ser Lys Phe Tyr Tyr
        355                 360                 365

Pro Pro Val Ala Ala Val Ser Ile Ser Tyr Pro Lys Glu Ala Ile Arg
    370                 375                 380

Ser Glu Cys Leu Ile Asp Gly Glu Leu Lys Gly Phe Gly Gln Leu His
385                 390                 395                 400

Pro Arg Ser Gln Gly Val Glu Thr Leu Gly Thr Ile Tyr Ser Ser Ser
                405                 410                 415

Leu Phe Pro Asn Arg Ala Pro Pro Gly Arg Val Leu Leu Leu Asn Tyr
            420                 425                 430

Ile Gly Gly Ala Thr Asn Thr Gly Ile Leu Ser Lys Thr Asp Ser Glu
        435                 440                 445
```

```
Leu Val Glu Thr Val Asp Arg Asp Leu Arg Lys Ile Leu Ile Asn Pro
    450                 455                 460

Asn Ala Gln Asp Pro Phe Val Val Gly Val Arg Leu Trp Pro Gln Ala
465                 470                 475                 480

Ile Pro Gln Phe Leu Val Gly His Leu Asp Leu Leu Asp Val Ala Lys
                485                 490                 495

Ala Ser Ile Arg Asn Thr Gly Phe Glu Gly Leu Phe Leu Gly Gly Asn
            500                 505                 510

Tyr Val Ser Gly Val Ala Leu Gly Arg Cys Val Glu Gly Ala Tyr Glu
        515                 520                 525

Val Ala Ala Glu Val Asn Asp Phe Leu Thr Asn Arg Val Tyr Lys
    530                 535                 540


<210> SEQ ID NO 8
<211> LENGTH: 536
<212> TYPE: PRT
<213> ORGANISM: Artificial sequence
<220> FEATURE:
<223> OTHER INFORMATION: Amino-acid sequence of PPO1 from wild-type
      sorghum(SbPPO1)

<400> SEQUENCE: 8

Met Val Ala Ala Ala Ala Met Ala Thr Ala Ala Ser Ala Ala Ala Pro
1               5                   10                  15

Leu Leu Asn Gly Thr Arg Arg Pro Ala Arg Leu Arg Arg Arg Gly Leu
            20                  25                  30

Arg Val Arg Cys Ala Ala Val Ala Gly Gly Ala Ala Glu Ala Pro Ala
        35                  40                  45

Ser Thr Gly Ala Arg Leu Ser Ala Asp Cys Val Val Val Gly Gly Gly
    50                  55                  60

Ile Ser Gly Leu Cys Thr Ala Gln Ala Leu Ala Thr Arg His Gly Val
65                  70                  75                  80

Gly Glu Val Leu Val Thr Glu Ala Arg Ala Arg Pro Gly Gly Asn Ile
                85                  90                  95

Thr Thr Val Glu Arg Pro Glu Glu Gly Tyr Leu Trp Glu Glu Gly Pro
            100                 105                 110

Asn Ser Phe Gln Pro Ser Asp Pro Val Leu Ser Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Ala Asp
145                 150                 155                 160

Leu Pro Phe Phe Asp Leu Met Ser Ile Pro Gly Lys Leu Arg Ala Gly
                165                 170                 175

Leu Gly Ala Leu Gly Ile Arg Pro Pro Pro Pro Gly Arg Glu Glu Ser
            180                 185                 190

Val Glu Glu Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Glu Ala
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Lys Pro Lys Gly
            260                 265                 270
```

```
Gln Thr Val Ala Ser Phe Arg Lys Gly Leu Ala Met Leu Pro Asn Ala
        275                 280                 285

Ile Thr Ser Ser Leu Gly Ser Lys Val Lys Leu Ser Trp Lys Leu Thr
    290                 295                 300

Ser Ile Thr Lys Ser Asp Gly Lys Gly Tyr Val Leu Glu Tyr Glu Thr
305                 310                 315                 320

Pro Glu Gly Val Val Leu Val Gln Ala Lys Ser Val Ile Met Thr Ile
                325                 330                 335

Pro Ser Tyr Val Ala Ser Asp Ile Leu Arg Pro Leu Ser Gly Asp Ala
            340                 345                 350

Ala Asp Ala Leu Ser Arg Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Leu Asn Tyr Ile Gly Gly Ala Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Ser Thr Ala Val Asp Pro Leu Val
    450                 455                 460

Leu Gly Val Arg Val Trp Pro Gln Ala Ile Pro Gln Phe Leu Val Gly
465                 470                 475                 480

His Leu Asp Leu Leu Glu Val Ala Lys Ser Ala Leu Asp Gln Gly Gly
                485                 490                 495

Tyr Asp Gly Leu Phe Leu Gly Gly Asn Tyr Val Ala Gly Val Ala Leu
            500                 505                 510

Gly Arg Cys Ile Glu Gly Ala Tyr Glu Ser Ala Ala Gln Ile Tyr Asp
        515                 520                 525

Phe Leu Thr Lys Tyr Ala Tyr Lys
    530                 535


<210> SEQ ID NO 9
<211> LENGTH: 531
<212> TYPE: PRT
<213> ORGANISM: Artificial sequence
<220> FEATURE:
<223> OTHER INFORMATION: Amino-acid sequence of PPO1 from wild-type
      wheat (TaPPO1-A)

<400> SEQUENCE: 9

Met Ala Gly Ala Thr Met Ala Thr Ala Thr Val Thr Ala Ala Ser Pro
1               5                   10                  15

Leu Arg Gly Arg Val Thr Gly Arg Pro Arg Arg Val Arg Thr Arg Cys
            20                  25                  30

Ala Ala Ala Ser Gly Ala Thr Glu Thr Pro Ala Ala Pro Gly Val Arg
        35                  40                  45

Leu Ser Ala Glu Cys Val Ile Val Gly Ala Gly Ile Ser Gly Leu Cys
    50                  55                  60

Thr Ala Gln Ala Leu Ala Thr Arg Tyr Gly Val Ser Asp Leu Leu Val
65                  70                  75                  80

Thr Glu Ala Arg Asp Arg Pro Gly Gly Asn Ile Thr Thr Val Glu Arg
```

-continued

```
                85                  90                  95

Pro Asp Glu Gly Tyr Leu Trp Glu Glu Gly Pro Asn Ser Phe Gln Pro
            100                 105                 110

Ser Asp Pro Val Leu Thr Met Ala Val Asp Ser Gly Leu Lys Asp Asp
        115                 120                 125

Leu Val Phe Gly Asp Pro Asn Ala Pro Arg Phe Val Leu Trp Glu Gly
    130                 135                 140

Lys Leu Arg Pro Val Pro Ser Lys Pro Gly Asp Leu Pro Phe Phe Ser
145                 150                 155                 160

Leu Met Ser Ile Pro Gly Lys Leu Arg Ala Gly Leu Gly Ala Leu Gly
                165                 170                 175

Ile Arg Pro Pro Pro Pro Gly Arg Glu Glu Ser Val Glu Glu Phe Val
            180                 185                 190

Arg Arg Asn Leu Gly Ala Glu Val Phe Glu Arg Leu Ile Glu Pro Phe
        195                 200                 205

Cys Ser Gly Val Tyr Ala Gly Asp Pro Ser Lys Leu Ser Met Lys Ala
    210                 215                 220

Ala Phe Gly Lys Val Trp Arg Leu Glu Glu Ile Gly Gly Ser Ile Ile
225                 230                 235                 240

Gly Gly Thr Ile Lys Ala Ile Gln Asp Lys Gly Lys Asn Pro Lys Pro
                245                 250                 255

Pro Arg Asp Pro Arg Leu Pro Ala Pro Lys Gly Gln Thr Val Ala Ser
            260                 265                 270

Phe Arg Lys Gly Leu Ala Met Leu Pro Asn Ala Ile Ala Ser Arg Leu
        275                 280                 285

Gly Ser Lys Val Lys Leu Ser Trp Lys Leu Thr Ser Ile Thr Lys Ala
    290                 295                 300

Asp Asn Gln Gly Tyr Val Leu Gly Tyr Glu Thr Pro Glu Gly Leu Val
305                 310                 315                 320

Ser Val Gln Ala Lys Ser Val Ile Met Thr Ile Pro Ser Tyr Val Ala
                325                 330                 335

Ser Asp Ile Leu Arg Pro Leu Ser Ile Asp Ala Ala Asp Ala Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Leu Asn Tyr Ile Gly Gly Ser Thr Asn Thr Gly Ile Val Ser Lys
            420                 425                 430

Thr Glu Ser Asp Leu Val Glu Ala Val Asp Arg Asp Leu Arg Lys Met
        435                 440                 445

Leu Ile Asn Pro Arg Ala Ala Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Ala Ala Ala Lys Ser Ala Leu Gly Arg Gly Gly Tyr Asp Gly Leu Phe
                485                 490                 495

Leu Gly Gly Asn Tyr Val Ala Gly Val Ala Leu Gly Arg Cys Ile Glu
            500                 505                 510
```

Gly Ala Tyr Glu Ser Ala Ser Gln Val Ser Asp Phe Leu Thr Lys Tyr
515 520 525

Ala Tyr Lys
530

<210> SEQ ID NO 10
<211> LENGTH: 531
<212> TYPE: PRT
<213> ORGANISM: Artificial sequence
<220> FEATURE:
<223> OTHER INFORMATION: Amino-acid sequence of PPO1 from wild-type wheat (TaPPO1-B)

<400> SEQUENCE: 10

Met Ala Gly Ala Thr Met Ala Thr Ala Thr Val Ala Ala Ala Ser Pro
1 5 10 15

Leu Arg Gly Arg Val Thr Gly Arg Pro His Arg Val Arg Pro Arg Cys
20 25 30

Ala Thr Ala Ser Ser Ala Thr Glu Thr Pro Ala Ala Pro Gly Val Arg
35 40 45

Leu Ser Ala Glu Cys Val Ile Val Gly Ala Gly Ile Ser Gly Leu Cys
50 55 60

Thr Ala Gln Ala Leu Ala Thr Arg Tyr Gly Val Ser Asp Leu Leu Val
65 70 75 80

Thr Glu Ala Arg Asp Arg Pro Gly Gly Asn Ile Thr Thr Val Glu Arg
85 90 95

Pro Asp Glu Gly Tyr Leu Trp Glu Glu Gly Pro Asn Ser Phe Gln Pro
100 105 110

Ser Asp Pro Val Leu Thr Met Ala Val Asp Ser Gly Leu Lys Asp Asp
115 120 125

Leu Val Phe Gly Asp Pro Asn Ala Pro Arg Phe Val Leu Trp Glu Gly
130 135 140

Lys Leu Arg Pro Val Pro Ser Lys Pro Gly Asp Leu Pro Phe Phe Ser
145 150 155 160

Leu Met Ser Ile Pro Gly Lys Leu Arg Ala Gly Leu Gly Ala Leu Gly
165 170 175

Ile Arg Pro Pro Pro Pro Gly Arg Glu Glu Ser Val Glu Glu Phe Val
180 185 190

Arg Arg Asn Leu Gly Ala Glu Val Phe Glu Arg Leu Ile Glu Pro Phe
195 200 205

Cys Ser Gly Val Tyr Ala Gly Asp Pro Ser Lys Leu Ser Met Lys Ala
210 215 220

Ala Phe Gly Lys Val Trp Arg Leu Glu Glu Ile Gly Gly Ser Ile Ile
225 230 235 240

Gly Gly Thr Ile Lys Ala Ile Gln Asp Lys Gly Lys Asn Pro Lys Pro
245 250 255

Pro Arg Asp Pro Arg Leu Pro Ala Pro Lys Gly Gln Thr Val Ala Ser
260 265 270

Phe Arg Lys Gly Leu Ala Met Leu Pro Asn Ala Ile Ala Ser Arg Leu
275 280 285

Gly Ser Lys Val Lys Leu Ser Trp Lys Leu Thr Ser Ile Thr Lys Ala
290 295 300

Asp Asn Gln Gly Tyr Val Leu Gly Tyr Glu Thr Pro Glu Gly Leu Val
305 310 315 320

Ser Val Gln Ala Lys Ser Val Ile Met Thr Ile Pro Ser Tyr Val Ala

```
                325                 330                 335

Ser Asp Ile Leu Arg Pro Leu Ser Ile Asp Ala Ala Asp Ala Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Leu Asn Tyr Ile Gly Gly Ser Thr Asn Thr Gly Ile Val Ser Lys
            420                 425                 430

Thr Glu Ser Asp Leu Val Gly Ala Val Asp Arg Asp Leu Arg Lys Met
        435                 440                 445

Leu Ile Asn Pro Arg Ala Ala Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Ala Ala Ala Lys Ser Ala Leu Gly Gln Gly Gly Tyr Asp Gly Leu Phe
                485                 490                 495

Leu Gly Gly Asn Tyr Val Ala Gly Val Ala Leu Gly Arg Cys Ile Glu
            500                 505                 510

Gly Ala Tyr Glu Ser Ala Ser Gln Val Ser Asp Phe Leu Thr Lys Tyr
        515                 520                 525

Ala Tyr Lys
    530


<210> SEQ ID NO 11
<211> LENGTH: 531
<212> TYPE: PRT
<213> ORGANISM: Artificial sequence
<220> FEATURE:
<223> OTHER INFORMATION: Amino-acid sequence of PPO1 from wild-type
      wheat (TaPPO1-D)

<400> SEQUENCE: 11

Met Ala Gly Ala Thr Met Ala Thr Ala Thr Val Thr Ala Ala Ser Pro
1               5                   10                  15

Leu Arg Gly Arg Val Thr Gly Arg Pro Arg Arg Val Arg Pro Arg Cys
            20                  25                  30

Ala Ala Ala Ser Gly Ala Thr Glu Thr Pro Ala Ala Pro Gly Val Arg
        35                  40                  45

Leu Ser Ala Asp Cys Val Ile Val Gly Ala Gly Ile Ser Gly Leu Cys
    50                  55                  60

Thr Ala Gln Ala Leu Ala Thr Arg Tyr Gly Val Gly Asp Leu Leu Ile
65                  70                  75                  80

Thr Glu Ala Arg Asp Arg Pro Gly Gly Asn Ile Thr Thr Val Glu Arg
                85                  90                  95

Pro Asp Glu Gly Tyr Leu Trp Glu Glu Gly Pro Asn Ser Phe Gln Pro
            100                 105                 110

Ser Asp Pro Val Leu Thr Met Ala Val Asp Ser Gly Leu Lys Asp Asp
        115                 120                 125

Leu Val Phe Gly Asp Pro Asn Ala Pro Arg Phe Val Leu Trp Glu Gly
    130                 135                 140
```

-continued

```
Lys Leu Arg Pro Val Pro Ser Lys Pro Gly Asp Leu Pro Phe Phe Ser
145                 150                 155                 160

Leu Met Ser Ile Pro Gly Lys Leu Arg Ala Gly Leu Gly Ala Leu Gly
                165                 170                 175

Ile Arg Pro Pro Pro Pro Gly Arg Glu Glu Ser Val Glu Glu Phe Val
            180                 185                 190

Arg Arg Asn Leu Gly Ala Glu Val Phe Glu Arg Leu Ile Glu Pro Phe
        195                 200                 205

Cys Ser Gly Val Tyr Ala Gly Asp Pro Ser Lys Leu Ser Met Lys Ala
    210                 215                 220

Ala Phe Gly Lys Val Trp Arg Leu Glu Glu Ile Gly Gly Ser Ile Ile
225                 230                 235                 240

Gly Gly Thr Ile Lys Ala Ile Gln Asp Lys Gly Lys Asn Pro Lys Pro
                245                 250                 255

Pro Arg Asp Pro Arg Leu Pro Ala Pro Lys Gly Gln Thr Val Ala Ser
            260                 265                 270

Phe Arg Lys Gly Leu Ala Met Leu Pro Asn Ala Ile Ala Ser Arg Leu
        275                 280                 285

Gly Ser Lys Val Lys Leu Ser Trp Lys Leu Thr Ser Ile Thr Lys Ala
    290                 295                 300

Asp Asn Gln Gly Tyr Val Leu Gly Tyr Glu Thr Pro Glu Gly Leu Val
305                 310                 315                 320

Ser Val Gln Ala Lys Ser Val Ile Met Thr Ile Pro Ser Tyr Val Ala
                325                 330                 335

Ser Asp Ile Leu Arg Pro Leu Ser Ile Asp Ala Ala Asp Ala Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Leu Asn Tyr Ile Gly Gly Ser Thr Asn Thr Gly Ile Val Ser Lys
            420                 425                 430

Thr Glu Ser Asp Leu Val Glu Ala Val Asp Ser Asp Leu Arg Lys Met
        435                 440                 445

Leu Ile Asn Pro Arg Ala Ala Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Ala Ala Ala Lys Ser Ala Leu Gly Arg Gly Gly Tyr Asp Gly Leu Phe
                485                 490                 495

Leu Gly Gly Asn Tyr Val Ala Gly Val Ala Leu Gly Arg Cys Ile Glu
            500                 505                 510

Gly Ala Tyr Glu Ser Ala Ser Gln Val Ser Asp Phe Leu Thr Lys Tyr
        515                 520                 525

Ala Tyr Lys
    530
```

<210> SEQ ID NO 12
<211> LENGTH: 558
<212> TYPE: PRT

```
<213> ORGANISM: Artificial sequence
<220> FEATURE:
<223> OTHER INFORMATION: Amino-acid sequence of PPO1 form wild-type
      tomato (SlPPO1)

<400> SEQUENCE: 12

Met Thr Thr Thr Ala Val Val Asn His Pro Ser Ile Phe Thr His Arg
1               5                   10                  15

Ser Pro Leu Pro Ser Pro Ser Ser Ser Ser Ser Ser Ser Pro Ser Phe
            20                  25                  30

Leu Phe Leu Asn Arg Thr Asn Phe Ile Pro Tyr Phe Ser Thr Ser Lys
        35                  40                  45

Arg Ser Ser Val Asn Cys Asn Gly Trp Arg Thr Arg Cys Ser Val Ala
    50                  55                  60

Lys Asn Tyr Thr Val Pro Pro Ser Glu Val Asp Gly Asn Gln Leu Pro
65                  70                  75                  80

Glu Leu Asp Cys Val Val Val Gly Ala Gly Ile Ser Gly Leu Cys Ile
                85                  90                  95

Ala Lys Val Ile Ser Ala Asn Tyr Pro Asn Leu Met Val Thr Glu Ala
            100                 105                 110

Arg Asp Arg Ala Gly Gly Asn Ile Thr Thr Val Glu Arg Asp Gly Tyr
        115                 120                 125

Leu Trp Glu Glu Gly Pro Asn Ser Phe Gln Pro Ser Asp Pro Met Leu
    130                 135                 140

Thr Met Ala Val Asp Cys Gly Leu Lys Asp Asp Leu Val Leu Gly Asp
145                 150                 155                 160

Pro Asp Ala Pro Arg Phe Val Leu Trp Lys Asp Lys Leu Arg Pro Val
                165                 170                 175

Pro Gly Lys Leu Thr Asp Leu Pro Phe Phe Asp Leu Met Ser Ile Pro
            180                 185                 190

Gly Lys Leu Arg Ala Gly Phe Gly Ala Ile Gly Leu Arg Pro Ser Pro
        195                 200                 205

Pro Gly Tyr Glu Glu Ser Val Glu Gln Phe Val Arg Arg Asn Leu Gly
    210                 215                 220

Ala Glu Val Phe Glu Arg Leu Ile Glu Ser Phe Cys Ser Gly Val Tyr
225                 230                 235                 240

Ala Gly Asp Pro Ser Lys Leu Ser Met Lys Ala Ala Phe Gly Lys Val
                245                 250                 255

Trp Lys Leu Glu Gln Thr Gly Gly Ser Ile Ile Gly Gly Thr Phe Lys
            260                 265                 270

Ala Ile Lys Glu Arg Ser Ser Asn Pro Lys Pro Pro Arg Asp Pro Arg
        275                 280                 285

Leu Pro Thr Pro Lys Gly Gln Thr Val Gly Ser Phe Arg Lys Gly Leu
    290                 295                 300

Arg Met Leu Pro Asp Ala Ile Cys Glu Arg Leu Gly Ser Lys Val Lys
305                 310                 315                 320

Leu Ser Trp Lys Leu Ser Ser Ile Thr Lys Ser Asp Lys Gly Gly Tyr
                325                 330                 335

Leu Leu Thr Tyr Glu Thr Pro Glu Gly Val Val Ser Leu Arg Ser Arg
            340                 345                 350

Ser Ile Val Met Thr Val Pro Ser Tyr Val Ala Ser Asn Ile Leu Arg
        355                 360                 365

Pro Leu Ser Val Ala Ala Ala Asp Ala Leu Ser Ser Phe Tyr Tyr Pro
    370                 375                 380
```

```
Pro Val Ala Ala Val Thr Ile Ser Tyr Pro Gln Glu Ala Ile Arg Asp
385                 390                 395                 400

Glu Arg Leu Val Asp Gly Glu Leu Lys Gly Phe Gly Gln Leu His Pro
                405                 410                 415

Arg Ser Gln Gly Val Glu Thr Leu Gly Thr Ile Tyr Ser Ser Ser Leu
            420                 425                 430

Phe Pro Asn Arg Ala Pro Asn Gly Arg Val Leu Leu Leu Asn Tyr Ile
        435                 440                 445

Gly Gly Ala Thr Asn Thr Glu Ile Val Ser Lys Thr Glu Ser Gln Leu
    450                 455                 460

Val Glu Ala Val Asp Arg Asp Leu Arg Lys Met Leu Ile Lys Pro Lys
465                 470                 475                 480

Ala Gln Asp Pro Phe Val Thr Gly Val Arg Val Trp Pro Gln Ala Ile
                485                 490                 495

Pro Gln Phe Leu Val Gly His Leu Asp Thr Leu Gly Thr Ala Lys Ala
            500                 505                 510

Ala Leu Ser Asp Asn Gly Leu Asp Gly Leu Phe Leu Gly Gly Asn Tyr
        515                 520                 525

Val Ser Gly Val Ala Leu Gly Arg Cys Val Glu Gly Ala Tyr Glu Ile
    530                 535                 540

Ala Ser Glu Val Thr Gly Phe Leu Ser Gln Tyr Ala Tyr Lys
545                 550                 555


<210> SEQ ID NO 13
<211> LENGTH: 557
<212> TYPE: PRT
<213> ORGANISM: Artificial sequence
<220> FEATURE:
<223> OTHER INFORMATION: Amino-acid sequence of PPO1 from wild-type
      potato (StPPO1)

<400> SEQUENCE: 13

Met Thr Thr Thr Ala Val Ala Asn His Pro Ser Ile Phe Thr His Arg
1               5                   10                  15

Ser Pro Leu Leu Ser Pro Ser Ser Ser Ser Ser Ser Pro Ser Phe Leu
            20                  25                  30

Phe Leu Asn Arg Thr Asn Phe Ile Pro Tyr Phe Ser Thr Ser Lys Arg
        35                  40                  45

Asn Ser Val Asn Cys Asn Gly Trp Arg Thr Arg Cys Ser Val Ala Lys
    50                  55                  60

Asp Tyr Thr Val Pro Pro Ser Glu Val Asp Gly Asn Gln Phe Pro Glu
65                  70                  75                  80

Leu Asp Cys Val Val Val Gly Ala Gly Ile Ser Gly Leu Cys Ile Thr
                85                  90                  95

Lys Val Ile Ser Asp Asn Tyr Pro Asn Leu Met Val Thr Glu Ala Arg
            100                 105                 110

Asp Arg Ala Gly Gly Asn Ile Thr Thr Val Glu Arg Asp Gly Tyr Leu
        115                 120                 125

Trp Glu Glu Gly Pro Asn Ser Phe Gln Pro Ser Asp Pro Met Leu Thr
    130                 135                 140

Met Ala Val Asp Cys Gly Leu Lys Asp Asp Leu Val Leu Gly Asp Pro
145                 150                 155                 160

Asp Ala Pro Arg Phe Val Leu Trp Lys Asp Lys Leu Arg Pro Val Pro
                165                 170                 175

Gly Lys Leu Thr Asp Leu Pro Phe Phe Asp Leu Met Ser Ile Pro Gly
            180                 185                 190
```

-continued

Lys Leu Arg Ala Gly Phe Gly Ala Ile Gly Leu Arg Pro Ser Pro Pro
195 200 205

Gly Tyr Glu Glu Ser Val Glu Gln Phe Val Arg Arg Asn Leu Gly Ala
210 215 220

Glu Val Phe Glu Arg Leu Ile Glu Pro Phe Cys Ser Gly Val Tyr Ala
225 230 235 240

Gly Asp Pro Ser Lys Leu Ser Met Lys Ala Ala Phe Gly Lys Val Trp
245 250 255

Lys Leu Glu Gln Thr Gly Gly Ser Ile Ile Gly Gly Thr Phe Lys Ala
260 265 270

Ile Lys Glu Arg Ser Ser Asn Pro Lys Pro Pro Arg Asp Pro Arg Leu
275 280 285

Pro Thr Pro Lys Gly Gln Thr Val Gly Ser Phe Arg Lys Gly Leu Arg
290 295 300

Met Leu Pro Asp Ala Ile Cys Glu Arg Leu Gly Ser Lys Val Lys Leu
305 310 315 320

Ser Trp Lys Leu Ser Ser Ile Thr Lys Ser Glu Lys Gly Gly Tyr Leu
325 330 335

Leu Thr Tyr Glu Thr Pro Glu Gly Val Val Ser Leu Arg Ser Arg Ser
340 345 350

Ile Val Met Thr Val Pro Ser Tyr Val Ala Ser Asn Ile Leu Arg Pro
355 360 365

Leu Ser Val Ala Ala Ala Asp Ala Leu Ser Ser Phe Tyr Tyr Pro Pro
370 375 380

Val Ala Ala Val Thr Ile Ser Tyr Pro Gln Glu Ala Ile Arg Asp Glu
385 390 395 400

Arg Leu Val Asp Gly Glu Leu Lys Gly Phe Gly Gln Leu His Pro Arg
405 410 415

Ser Gln Gly Val Glu Thr Leu Gly Thr Ile Tyr Ser Ser Ser Leu Phe
420 425 430

Pro Asn Arg Ala Pro Asn Gly Arg Val Leu Leu Leu Asn Tyr Ile Gly
435 440 445

Gly Ala Thr Asn Thr Glu Ile Val Ser Lys Thr Glu Ser Gln Leu Val
450 455 460

Glu Ala Val Asp Arg Asp Leu Arg Lys Met Leu Ile Lys Pro Lys Ala
465 470 475 480

Gln Asp Pro Phe Val Thr Gly Val Arg Val Trp Pro Gln Ala Ile Pro
485 490 495

Gln Phe Leu Val Gly His Leu Asp Thr Leu Gly Thr Ala Lys Thr Ala
500 505 510

Leu Ser Asp Asn Gly His Asp Gly Leu Phe Leu Gly Gly Asn Tyr Val
515 520 525

Ser Gly Val Ala Leu Gly Arg Cys Val Glu Gly Ala Tyr Glu Ile Ala
530 535 540

Ser Glu Val Thr Gly Phe Leu Ser Gln Tyr Ala Tyr Lys
545 550 555

<210> SEQ ID NO 14
<211> LENGTH: 553
<212> TYPE: PRT
<213> ORGANISM: Artificial sequence
<220> FEATURE:
<223> OTHER INFORMATION: Amino-acid sequence of PPO1 form wild-type
tobacco (NtPPO1)

-continued

<400> SEQUENCE: 14

```
Met Thr Thr Thr Pro Ile Ala Asn His Pro Asn Val Phe Thr His Arg
1               5                   10                  15

Ser Pro Pro Ser Ser Ser Ser Ser Ser Pro Ser Ala Phe Leu Thr Arg
            20                  25                  30

Thr Ser Phe Leu Pro Phe Ser Ser Ile Cys Lys Arg Asn Ser Val Asn
        35                  40                  45

Cys Thr Gly Trp Arg Thr Arg Cys Ser Val Ala Lys Asp Tyr Thr Val
    50                  55                  60

Pro Ser Ser Ala Val Asp Gly Gly Pro Ala Ala Glu Leu Asp Cys Val
65                  70                  75                  80

Ile Val Gly Ala Gly Ile Ser Gly Leu Cys Ile Ala Gln Val Met Ser
                85                  90                  95

Ala Asn Tyr Pro Asn Leu Met Val Thr Glu Ala Arg Asp Arg Ala Gly
            100                 105                 110

Gly Asn Ile Thr Thr Val Glu Arg Asp Gly Tyr Leu Trp Glu Glu Gly
        115                 120                 125

Pro Asn Ser Phe Gln Pro Ser Asp Pro Met Leu Thr Met Ala Val Asp
    130                 135                 140

Cys Gly Leu Lys Asp Asp Leu Val Leu Gly Asp Pro Asn Ala Pro Arg
145                 150                 155                 160

Phe Val Leu Trp Lys Gly Lys Leu Arg Pro Val Pro Ser Lys Leu Thr
                165                 170                 175

Asp Leu Pro Phe Phe Asp Leu Met Ser Ile Pro Gly Lys Leu Arg Ala
            180                 185                 190

Gly Phe Gly Ala Ile Gly Leu Arg Pro Ser Pro Pro Gly His Glu Glu
        195                 200                 205

Ser Val Glu Gln Phe Val Arg Arg Asn Leu Gly Gly Glu Val Phe Glu
    210                 215                 220

Arg Leu Ile Glu Pro Phe Cys Ser Gly Val Tyr Ala Gly Asp Pro Ser
225                 230                 235                 240

Lys Leu Ser Met Lys Ala Ala Phe Gly Lys Val Trp Lys Leu Glu Glu
                245                 250                 255

Thr Gly Gly Ser Ile Ile Gly Gly Thr Phe Lys Ala Ile Lys Glu Arg
            260                 265                 270

Ser Ser Thr Pro Lys Ala Pro Arg Asp Pro Arg Leu Pro Lys Pro Lys
        275                 280                 285

Gly Gln Thr Val Gly Ser Phe Arg Lys Gly Leu Arg Met Leu Pro Asp
    290                 295                 300

Ala Ile Ser Ala Arg Leu Gly Ser Lys Leu Lys Leu Ser Trp Lys Leu
305                 310                 315                 320

Ser Ser Ile Thr Lys Ser Glu Lys Gly Gly Tyr Arg Leu Thr Tyr Glu
                325                 330                 335

Thr Pro Glu Gly Val Val Ser Leu Gln Ser Arg Ser Ile Val Met Thr
            340                 345                 350

Val Pro Ser Tyr Val Ala Ser Asn Ile Leu Arg Pro Leu Ser Val Ala
        355                 360                 365

Ala Ala Asp Ala Leu Ser Asn Phe Tyr Tyr Pro Pro Val Gly Ala Val
    370                 375                 380

Thr Ile Ser Tyr Pro Gln Glu Ala Ile Arg Asp Glu Arg Leu Val Asp
385                 390                 395                 400

Gly Glu Leu Lys Gly Phe Gly Gln Leu His Pro Arg Thr Gln Gly Val
                405                 410                 415
```

```
Glu Thr Leu Gly Thr Ile Tyr Ser Ser Ser Leu Phe Pro Asn Arg Ala
            420                 425                 430

Pro Lys Gly Arg Val Leu Leu Leu Asn Tyr Ile Gly Gly Ala Lys Asn
        435                 440                 445

Pro Glu Ile Leu Ser Lys Thr Glu Ser Gln Leu Val Glu Val Val Asp
    450                 455                 460

Arg Asp Leu Arg Lys Met Leu Ile Lys Pro Lys Ala Gln Asp Pro Leu
465                 470                 475                 480

Val Val Gly Val Arg Val Trp Pro Gln Ala Ile Pro Gln Phe Leu Val
                485                 490                 495

Gly His Leu Asp Thr Leu Ser Thr Ala Lys Ala Ala Met Ser Asp Asn
            500                 505                 510

Gly Leu Glu Gly Leu Phe Leu Gly Gly Asn Tyr Val Ser Gly Val Ala
        515                 520                 525

Leu Gly Arg Cys Val Glu Gly Ala Tyr Glu Val Ala Ser Glu Val Thr
    530                 535                 540

Gly Phe Leu Pro Arg Tyr Ala Tyr Lys
545                 550


<210> SEQ ID NO 15
<211> LENGTH: 537
<212> TYPE: PRT
<213> ORGANISM: Artificial sequence
<220> FEATURE:
<223> OTHER INFORMATION: Amino-acid sequence of PPO1 from wild-type
      Arabidopsis thaliana (AtPPO1)

<400> SEQUENCE: 15

Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
```

```
    210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285

Ala Ile Ser Ala Arg Leu Gly Ser Lys Val Lys Leu Ser Trp Lys Leu
    290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
            340                 345                 350

Ala Ala Asn Ala Leu Ser Lys Leu Tyr Tyr Pro Pro Val Ala Ala Val
        355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Leu Asn Tyr Ile Gly Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
        515                 520                 525

Asn Phe Met Ser Arg Tyr Ala Tyr Lys
    530                 535
```

<210> SEQ ID NO 16
<211> LENGTH: 539
<212> TYPE: PRT
<213> ORGANISM: Artificial sequence
<220> FEATURE:
<223> OTHER INFORMATION: Amino-acid sequence of PPO1 from wild-type upland cotton (GhPPO1)

<400> SEQUENCE: 16

```
Met Thr Ala Leu Ile Asp Leu Ser Leu Leu Arg Ser Ser Pro Ser Val
1               5                   10                  15

Ser Pro Phe Ser Ile Pro His His Gln His Pro Pro Arg Phe Arg Lys
            20                  25                  30
```

```
Pro Phe Lys Leu Arg Cys Ser Leu Ala Glu Gly Pro Thr Ile Ser Ser
        35                  40                  45

Ser Lys Ile Asp Gly Gly Glu Ser Ser Ile Ala Asp Cys Val Ile Val
    50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
            100                 105                 110

Glu Gly Pro Asn Ser Phe Gln Pro Ser Asp Pro Ile Leu Thr Met Ala
        115                 120                 125

Val Asp Ser Gly Leu Lys Asp Asp Leu Val Leu Gly Asp Pro Asn Ala
    130                 135                 140

Pro Arg Phe Val Leu Trp Glu Gly Lys Leu Arg Pro Val Pro Ser Lys
145                 150                 155                 160

Pro Thr Asp Leu Pro Phe Phe Asp Leu Met Ser Ile Ala Gly Lys Leu
                165                 170                 175

Arg Ala Gly Phe Gly Ala Ile Gly Ile Arg Pro Pro Pro Pro Gly Tyr
            180                 185                 190

Glu Glu Ser Val Glu Glu Phe Val Arg Arg Asn Leu Gly Ala Glu Val
        195                 200                 205

Phe Glu Arg Phe Ile Glu Pro Phe Cys Ser Gly Val Tyr Ala Gly Asp
    210                 215                 220

Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
                245                 250                 255

Glu Arg Asn Lys Thr Pro Lys Pro Pro Arg Asp Pro Arg Leu Pro Lys
            260                 265                 270

Pro Lys Gly Gln Thr Val Gly Ser Phe Arg Lys Gly Leu Thr Met Leu
        275                 280                 285

Pro Glu Ala Ile Ala Asn Ser Leu Gly Ser Asn Val Lys Leu Ser Trp
    290                 295                 300

Lys Leu Ser Ser Ile Thr Lys Leu Gly Asn Gly Gly Tyr Asn Leu Thr
305                 310                 315                 320

Phe Glu Thr Pro Glu Gly Met Val Ser Leu Gln Ser Arg Ser Val Val
                325                 330                 335

Met Thr Ile Pro Ser His Val Ala Ser Asn Leu Leu His Pro Leu Ser
            340                 345                 350

Ala Ala Ala Ala Asp Ala Leu Ser Gln Phe Tyr Tyr Pro Pro Val Ala
        355                 360                 365

Ser Val Thr Val Ser Tyr Pro Lys Glu Ala Ile Arg Lys Glu Cys Leu
    370                 375                 380

Ile Asp Gly Glu Leu Lys Gly Phe Gly Gln Leu His Pro Arg Ser Gln
385                 390                 395                 400

Gly Ile Glu Thr Leu Gly Thr Ile Tyr Ser Ser Ser Leu Phe Pro Asn
                405                 410                 415

Arg Ala Pro Ser Gly Arg Val Leu Leu Leu Asn Tyr Ile Gly Gly Ala
            420                 425                 430

Thr Asn Thr Gly Ile Leu Ser Lys Thr Glu Gly Glu Leu Val Glu Ala
        435                 440                 445

Val Asp Arg Asp Leu Arg Lys Met Leu Ile Asn Pro Asn Ala Lys Asp
```

-continued

```
    450                 455                 460

Pro Leu Val Leu Gly Val Arg Val Trp Pro Lys Ala Ile Pro Gln Phe
465                 470                 475                 480

Leu Val Gly His Leu Asp Leu Leu Asp Ser Ala Lys Met Ala Leu Arg
                485                 490                 495

Asp Ser Gly Phe His Gly Leu Phe Leu Gly Gly Asn Tyr Val Ser Gly
            500                 505                 510

Val Ala Leu Gly Arg Cys Val Glu Gly Ala Tyr Glu Val Ala Ala Glu
        515                 520                 525

Val Lys Glu Phe Leu Ser Gln Tyr Ala Tyr Lys
    530                 535


<210> SEQ ID NO 17
<211> LENGTH: 538
<212> TYPE: PRT
<213> ORGANISM: Artificial sequence
<220> FEATURE:
<223> OTHER INFORMATION: Amino-acid sequence of PPO1 from wild-type
      radish (RsPPO1)

<400> SEQUENCE: 17

Met Asp Leu Ser Leu Leu Arg Pro Gln Pro Phe Leu Ser Pro Phe Ser
1               5                   10                  15

Asn Pro Phe Pro Arg Ser Arg Pro Tyr Tyr Lys Pro Leu Asn Leu His
            20                  25                  30

Cys Ser Val Ser Gly Gly Ser Val Val Gly Ser Ser Thr Ile Glu Gly
        35                  40                  45

Gly Gly Gly Gly Gly Lys Thr Val Ala Ala Asp Cys Val Ile Val Gly
    50                  55                  60

Gly Gly Ile Ser Gly Leu Cys Ile Ala Gln Ala Leu Val Thr Lys His
65                  70                  75                  80

Pro Asp Ala Ala Lys Asn Val Ile Val Thr Glu Ala Lys Asp Arg Val
                85                  90                  95

Gly Gly Asn Ile Ile Thr Arg Glu Glu Gln Gly Phe Leu Trp Glu Glu
            100                 105                 110

Gly Pro Asn Ser Phe Gln Pro Ser Asp Pro Met Leu Thr Met Val Val
        115                 120                 125

Asp Ser Gly Leu Lys Asp Asp Leu Val Leu Gly Asp Pro Thr Ala Pro
    130                 135                 140

Arg Phe Val Leu Trp Asn Gly Lys Leu Arg Pro Val Pro Ser Lys Leu
145                 150                 155                 160

Thr Asp Leu Pro Phe Phe Asp Leu Met Ser Ile Arg Gly Lys Ile Arg
                165                 170                 175

Ala Gly Phe Gly Ala Ile Gly Ile Arg Pro Ser Pro Pro Gly Arg Glu
            180                 185                 190

Glu Ser Val Glu Glu Phe Val Arg Arg Asn Leu Gly Asp Glu Val Phe
        195                 200                 205

Glu Arg Leu Ile Glu Pro Phe Cys Ser Gly Val Tyr Ala Gly Asp Pro
    210                 215                 220

Ala Lys Leu Ser Met Lys Ala Ala Phe Gly Lys Val Trp Lys Leu Glu
225                 230                 235                 240

Glu Asn Gly Gly Ser Ile Ile Gly Gly Ala Phe Lys Ala Ile Gln Ala
                245                 250                 255

Arg Asn Lys Ala Pro Lys Thr Thr Arg Asp Pro Arg Leu Pro Lys Pro
            260                 265                 270
```

-continued

```
Lys Gly Gln Thr Val Gly Ser Phe Arg Lys Gly Leu Thr Met Leu Pro
        275                 280                 285

Glu Ala Ile Ser Ala Arg Leu Gly Asn Lys Val Lys Val Ser Trp Lys
    290                 295                 300

Leu Ser Ser Ile Thr Lys Leu Ala Asn Gly Glu Tyr Ser Leu Thr Tyr
305                 310                 315                 320

Glu Thr Pro Glu Gly Ile Val Thr Val Gln Ser Lys Ser Val Val Met
                325                 330                 335

Thr Val Pro Ser His Val Ala Ser Ser Leu Leu Arg Pro Leu Ser Asp
            340                 345                 350

Ser Ala Ala Glu Ala Leu Ser Lys Leu Tyr Tyr Pro Pro Val Ala Ala
        355                 360                 365

Val Ser Ile Ser Tyr Pro Lys Glu Ala Ile Arg Ser Glu Cys Leu Ile
    370                 375                 380

Asp Gly Glu Leu Lys Gly Phe Gly Gln Leu His Pro Arg Thr Gln Lys
385                 390                 395                 400

Val Glu Thr Leu Gly Thr Ile Tyr Ser Ser Ser Leu Phe Pro Asn Arg
                405                 410                 415

Ala Pro Pro Gly Arg Val Leu Leu Leu Asn Tyr Ile Gly Gly Thr Thr
            420                 425                 430

Asn Thr Gly Ile Leu Ser Lys Ser Glu Gly Glu Leu Val Glu Ala Val
        435                 440                 445

Asp Arg Asp Leu Arg Lys Met Leu Ile Lys Pro Ser Ser Thr Asp Pro
    450                 455                 460

Leu Val Leu Gly Val Arg Val Trp Pro Gln Ala Ile Pro Gln Phe Leu
465                 470                 475                 480

Ile Gly His Ile Asp Leu Val Asp Ala Ala Lys Ala Ser Leu Ser Ser
                485                 490                 495

Ser Gly His Glu Gly Ile Phe Leu Gly Gly Asn Tyr Val Ala Gly Val
            500                 505                 510

Ala Leu Gly Arg Cys Val Glu Cys Ala Tyr Glu Thr Ala Thr Gln Val
        515                 520                 525

Asn Asp Phe Met Ser Arg Tyr Thr Tyr Lys
    530                 535


<210> SEQ ID NO 18
<211> LENGTH: 535
<212> TYPE: PRT
<213> ORGANISM: Artificial sequence
<220> FEATURE:
<223> OTHER INFORMATION: Amino-acid sequence of PPO1 from wild-type
      foxtail millet (SiPPO1)

<400> SEQUENCE: 18

Met Val Ala Ala Ala Met Ala Thr Ala Pro Ser Ala Gly Val Pro Pro
1               5                   10                  15

Leu Arg Gly Thr Arg Gly Pro Ala Arg Phe Arg Ile Arg Gly Val Ser
            20                  25                  30

Val Arg Cys Ala Ala Val Ala Gly Gly Ala Ala Glu Ala Pro Ala Ser
        35                  40                  45

Ala Gly Ala Arg Val Ser Ala Asp Cys Val Val Val Gly Gly Gly Ile
    50                  55                  60

Ser Gly Leu Cys Thr Ala Gln Ala Leu Ala Thr Lys His Gly Val Gly
65                  70                  75                  80

Asp Val Leu Val Thr Glu Ala Arg Ala Arg Pro Gly Gly Asn Ile Thr
                85                  90                  95
```

-continued

```
Thr Val Glu Arg Pro Asp Glu Gly Tyr Leu Trp Glu Glu Gly Pro Asn
            100                 105                 110

Ser Phe Gln Pro Ser Asp Pro Val Leu Thr Met Ala Val Asp Ser Gly
        115                 120                 125

Leu Lys Asp Asp Leu Val Phe Gly Asp Pro Asn Ala Pro Arg Phe Val
    130                 135                 140

Leu Trp Glu Gly Lys Leu Arg Pro Val Pro Ser Lys Pro Ala Asp Leu
145                 150                 155                 160

Pro Phe Phe Asp Leu Met Ser Ile Pro Gly Lys Leu Arg Ala Gly Phe
                165                 170                 175

Gly Ala Leu Gly Ile Arg Pro Pro Pro Pro Gly Arg Glu Glu Ser Val
            180                 185                 190

Glu Glu Phe Val Arg Arg Asn Leu Gly Ala Glu Val Phe Glu Arg Leu
        195                 200                 205

Ile Glu Pro Phe Cys Ser Gly Val Tyr Ala Gly Asp Pro Ser Lys Leu
    210                 215                 220

Ser Met Lys Ala Ala Phe Gly Lys Val Trp Arg Leu Glu Glu Ala Gly
225                 230                 235                 240

Gly Ser Ile Ile Gly Gly Thr Ile Lys Thr Ile Gln Glu Arg Gly Lys
                245                 250                 255

Asn Pro Lys Pro Pro Arg Asp Pro Arg Leu Pro Thr Pro Lys Gly Gln
            260                 265                 270

Thr Val Ala Ser Phe Arg Lys Gly Leu Ala Met Leu Pro Asn Ala Ile
        275                 280                 285

Thr Ser Ser Leu Gly Ser Lys Val Lys Leu Ser Trp Lys Leu Thr Ser
    290                 295                 300

Ile Thr Lys Ser Asp Gly Met Gly Tyr Val Leu Val Tyr Glu Thr Pro
305                 310                 315                 320

Glu Gly Val Val Ser Val Gln Ala Lys Ser Val Ile Met Thr Ile Pro
                325                 330                 335

Ser Tyr Val Ala Ser Asp Ile Leu Arg Pro Leu Ser Ser Asp Ala Ala
            340                 345                 350

Asp Ala Leu Ser Arg Phe Tyr Tyr Pro Pro Val Ala Ala Val Thr Ile
        355                 360                 365

Ser Tyr Pro Lys Glu Ala Ile Arg Lys Glu Cys Leu Ile Asp Gly Glu
    370                 375                 380

Leu Gln Gly Phe Gly Gln Leu His Pro Arg Ser Gln Gly Val Glu Thr
385                 390                 395                 400

Leu Gly Thr Ile Tyr Ser Ser Ser Leu Phe Pro Asn Arg Ala Pro Ala
                405                 410                 415

Gly Arg Val Leu Leu Leu Asn Tyr Ile Gly Gly Ala Thr Asn Thr Gly
            420                 425                 430

Ile Val Ser Lys Ser Ala Ser Glu Leu Val Glu Ala Val Asp Arg Asp
        435                 440                 445

Leu Arg Lys Met Leu Ile Asn Pro Ser Ala Val Asp Pro Leu Val Leu
    450                 455                 460

Gly Val Arg Val Trp Pro Gln Ala Ile Pro Gln Phe Leu Val Gly His
465                 470                 475                 480

Leu Asp Leu Leu Glu Ala Ala Lys Ser Ser Leu Asp Arg Gly Gly Tyr
                485                 490                 495

Asp Gly Leu Phe Leu Gly Gly Asn Tyr Val Ala Gly Val Ala Leu Gly
            500                 505                 510
```

```
Arg Cys Val Glu Gly Ala Tyr Glu Ser Ala Ser Gln Ile Ser Asp Phe
        515                 520                 525

Leu Thr Lys Tyr Ala Tyr Lys
    530                 535


<210> SEQ ID NO 19
<211> LENGTH: 537
<212> TYPE: PRT
<213> ORGANISM: Artificial sequence
<220> FEATURE:
<223> OTHER INFORMATION: Amino-acid sequence of PPO1 form wild-type
      cabbage (BoPPO1)

<400> SEQUENCE: 19

Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Pro Asn Leu Arg Cys
            20                  25                  30

Ser Val Ser Gly Gly Ser Val Val Gly Gly Ser Ser Thr Ile Glu Gly
        35                  40                  45

Gly Gly Gly Gly Lys Thr Val Ala Ala Asp Cys Val Ile Val Gly Gly
    50                  55                  60

Gly Ile Ser Gly Leu Cys Ile Ala Gln Ala Leu Val Thr Lys His Pro
65                  70                  75                  80

Asp Ala Ala Lys Ser Val Met Val Thr Glu Ala Lys Asp Arg Val Gly
                85                  90                  95

Gly Asn Ile Ile Thr Arg Glu Glu Gln Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Ile Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ala
    210                 215                 220

Lys Leu Ser Met Lys Ala Ala Phe Gly Lys Val Trp Lys Leu Glu Glu
225                 230                 235                 240

Asn Gly Gly Ser Ile Ile Gly Gly Ala Phe Lys Ala Ile Gln Ala Arg
                245                 250                 255

Asn Lys Ala Pro Lys Thr Thr Arg Asp Pro Arg Leu Pro Lys Pro Lys
            260                 265                 270

Gly Gln Thr Val Gly Ser Phe Arg Lys Gly Leu Thr Met Leu Pro Glu
        275                 280                 285

Ala Ile Ser Ala Arg Leu Gly Asp Lys Val Lys Val Ser Trp Lys Leu
    290                 295                 300

Ser Ser Ile Ser Lys Leu Pro Ser Gly Gly Tyr Ser Leu Thr Tyr Glu
305                 310                 315                 320

Thr Pro Glu Gly Ile Val Thr Val Gln Ser Lys Ser Val Val Met Thr
                325                 330                 335
```

Val Pro Ser His Val Ala Ser Ser Leu Leu Arg Pro Leu Ser Asp Ser
340 345 350

Ala Ala Glu Ala Leu Ser Lys Leu Tyr Tyr Pro Pro Val Ala Ala Val
355 360 365

Ser Ile Ser Tyr Leu Lys Glu Ala Ile Arg Ser Glu Cys Leu Ile Asp
370 375 380

Gly Glu Leu Lys Gly Phe Gly Gln Leu His Pro Arg Thr Gln Lys Val
385 390 395 400

Glu Thr Leu Gly Thr Ile Tyr Ser Ser Ser Leu Phe Pro Asn Arg Ala
405 410 415

Pro Pro Gly Arg Val Leu Leu Leu Asn Tyr Ile Gly Gly Ala Thr Asn
420 425 430

Thr Gly Ile Leu Ser Lys Ser Glu Gly Glu Leu Val Glu Ala Val Asp
435 440 445

Arg Asp Leu Arg Lys Met Leu Ile Met Pro Ser Ser Thr Asp Pro Leu
450 455 460

Val Leu Gly Val Lys Val Trp Pro Gln Ala Ile Pro Gln Phe Leu Ile
465 470 475 480

Gly His Ile Asp Leu Val Asp Ala Ala Lys Ala Ser Leu Ser Ser Ser
485 490 495

Gly His Glu Gly Leu Phe Leu Gly Gly Asn Tyr Val Ala Gly Val Ala
500 505 510

Leu Gly Arg Cys Val Glu Gly Ala Tyr Glu Thr Ala Thr Gln Val Asn
515 520 525

Asp Phe Met Ser Arg Tyr Ala Tyr Lys
530 535

<210> SEQ ID NO 20
<211> LENGTH: 536
<212> TYPE: PRT
<213> ORGANISM: Artificial sequence
<220> FEATURE:
<223> OTHER INFORMATION: Amino-acid sequence of PPO1 from rice mutant (OsPPO1 L423S)

<400> SEQUENCE: 20

Met Ala Ala Ala Ala Ala Ala Met Ala Thr Ala Thr Ser Ala Thr Ala
1 5 10 15

Ala Pro Pro Leu Arg Ile Arg Asp Ala Ala Arg Arg Thr Arg Arg Arg
20 25 30

Gly His Val Arg Cys Ala Val Ala Ser Gly Ala Ala Glu Ala Pro Ala
35 40 45

Ala Pro Gly Ala Arg Val Ser Ala Asp Cys Val Val Val Gly Gly Gly
50 55 60

Ile Ser Gly Leu Cys Thr Ala Gln Ala Leu Ala Thr Lys His Gly Val
65 70 75 80

Gly Asp Val Leu Val Thr Glu Ala Arg Ala Arg Pro Gly Gly Asn Ile
85 90 95

Thr Thr Ala Glu Arg Ala Gly Glu Gly Tyr Leu Trp Glu Glu Gly Pro
100 105 110

Asn Ser Phe Gln Pro Ser Asp Pro Val Leu Thr Met Ala Val Asp Ser
115 120 125

Gly Leu Lys Asp Asp Leu Val Phe Gly Asp Pro Asn Ala Pro Arg Phe
130 135 140

Val Leu Trp Glu Gly Lys Leu Arg Pro Val Pro Ser Lys Pro Gly Asp

-continued

```
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Ser Asn Tyr Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535
```

<210> SEQ ID NO 21
<211> LENGTH: 536
<212> TYPE: PRT
<213> ORGANISM: Artificial sequence
<220> FEATURE:
<223> OTHER INFORMATION: Amino-acid sequence of PPO1 from rice mutant (OsPPO1 L423I)

<400> SEQUENCE: 21

```
Met Ala Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg Arg
            20                  25                  30

Gly His Val Arg Cys Ala Val Ala Ser Gly Ala Ala Glu Ala Pro Ala
        35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
```

-continued

```
385                 390                 395                 400

Thr Leu Gly Thr Ile Tyr Ser Ser Ser Leu Phe Pro Asn Arg Ala Pro
                405                 410                 415

Ala Gly Arg Val Leu Leu Ile Asn Tyr Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535


<210> SEQ ID NO 22
<211> LENGTH: 536
<212> TYPE: PRT
<213> ORGANISM: Artificial sequence
<220> FEATURE:
<223> OTHER INFORMATION: Amino-acid sequence of PPO1 from rice mutant
      (OsPPO1 L423G)

<400> SEQUENCE: 22

Met Ala Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg Arg
            20                  25                  30

Gly His Val Arg Cys Ala Val Ala Ser Gly Ala Ala Glu Ala Pro Ala
        35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205
```

-continued

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Gly Asn Tyr Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535

<210> SEQ ID NO 23
<211> LENGTH: 536
<212> TYPE: PRT
<213> ORGANISM: Artificial sequence
<220> FEATURE:
<223> OTHER INFORMATION: Amino-acid sequence of PPO1 from rice mutant
      (OsPPO1 Y425M)

<400> SEQUENCE: 23

Met Ala Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg Arg
            20                  25                  30

```
Gly His Val Arg Cys Ala Val Ala Ser Gly Ala Ala Glu Ala Pro Ala
        35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Leu Asn Met Ile Gly Gly Ser Thr Asn Thr
            420                 425                 430

Gly Ile Val Ser Lys Thr Glu Ser Glu Leu Val Glu Ala Val Asp Arg
        435                 440                 445
```

```
Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535


<210> SEQ ID NO 24
<211> LENGTH: 536
<212> TYPE: PRT
<213> ORGANISM: Artificial sequence
<220> FEATURE:
<223> OTHER INFORMATION: Amino-acid sequence of PPO1 from rice mutant
      (OsPPO1 Y425I)

<400> SEQUENCE: 24

Met Ala Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg Arg
            20                  25                  30

Gly His Val Arg Cys Ala Val Ala Ser Gly Ala Ala Glu Ala Pro Ala
        35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270
```

```
Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Leu Asn Ile Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535


<210> SEQ ID NO 25
<211> LENGTH: 536
<212> TYPE: PRT
<213> ORGANISM: Artificial sequence
<220> FEATURE:
<223> OTHER INFORMATION: Amino-acid sequence of PPO1 from rice mutant
      (OsPPO1 Y425V)

<400> SEQUENCE: 25

Met Ala Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg Arg
            20                  25                  30

Gly His Val Arg Cys Ala Val Ala Ser Gly Ala Ala Glu Ala Pro Ala
        35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
```

-continued

```
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Leu Asn Val Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510
```

```
Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535


<210> SEQ ID NO 26
<211> LENGTH: 536
<212> TYPE: PRT
<213> ORGANISM: Artificial sequence
<220> FEATURE:
<223> OTHER INFORMATION: Amino-acid sequence of PPO1 from rice mutant
      (OsPPO1 L423S/Y425I)

<400> SEQUENCE: 26

Met Ala Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg Arg
            20                  25                  30

Gly His Val Arg Cys Ala Val Ala Ser Gly Ala Ala Glu Ala Pro Ala
        35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
```

-continued

```
                325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Val Leu Leu Ser Asn Ile Ile Gly Gly Ser Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Pro Lys Ala Val Asp Pro Leu Val
    450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Gly Asn Tyr Val Ala Gly Val Ala Leu
            500                 505                 510

Gly Arg Cys Val Glu Gly Ala Tyr Glu Ser Ala Ser Gln Ile Ser Asp
        515                 520                 525

Tyr Leu Thr Lys Tyr Ala Tyr Lys
    530                 535


<210> SEQ ID NO 27
<211> LENGTH: 537
<212> TYPE: PRT
<213> ORGANISM: Artificial sequence
<220> FEATURE:
<223> OTHER INFORMATION: Amino-acid sequence of PPO1 from corn mutant
      (ZmPPO1 L424T/Y426V)

<400> SEQUENCE: 27

Met Val Ala Ala Thr Ala Thr Ala Thr Ala Met Ala Thr Ala Ala Ser
1               5                   10                  15

Pro Leu Leu Asn Gly Thr Arg Ile Pro Ala Arg Leu Arg His Arg Gly
            20                  25                  30

Leu Ser Val Arg Cys Ala Ala Val Ala Gly Gly Ala Ala Glu Ala Pro
        35                  40                  45

Ala Ser Thr Gly Ala Arg Leu Ser Ala Asp Cys Val Val Val Gly Gly
    50                  55                  60

Gly Ile Ser Gly Leu Cys Thr Ala Gln Ala Leu Ala Thr Arg His Gly
65                  70                  75                  80

Val Gly Asp Val Leu Val Thr Glu Ala Arg Ala Arg Pro Gly Gly Asn
                85                  90                  95

Ile Thr Thr Val Glu Arg Pro Glu Glu Gly Tyr Leu Trp Glu Glu Gly
            100                 105                 110

Pro Asn Ser Phe Gln Pro Ser Asp Pro Val Leu Thr Met Ala Val Asp
        115                 120                 125

Ser Gly Leu Lys Asp Asp Leu Val Phe Gly Asp Pro Asn Ala Pro Arg
    130                 135                 140
```

-continued

```
Phe Val Leu Trp Glu Gly Lys Leu Arg Pro Val Pro Ser Lys Pro Ala
145                 150                 155                 160

Asp Leu Pro Phe Phe Asp Leu Met Ser Ile Pro Gly Lys Leu Arg Ala
                165                 170                 175

Gly Leu Gly Ala Leu Gly Ile Arg Pro Pro Pro Pro Gly Arg Glu Glu
            180                 185                 190

Ser Val Glu Glu Phe Val Arg Arg Asn Leu Gly Ala Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Arg Leu Glu Glu
225                 230                 235                 240

Thr Gly Gly Ser Ile Ile Gly Gly Thr Ile Lys Thr Ile Gln Glu Arg
                245                 250                 255

Ser Lys Asn Pro Lys Pro Pro Arg Asp Ala Arg Leu Pro Lys Pro Lys
            260                 265                 270

Gly Gln Thr Val Ala Ser Phe Arg Lys Gly Leu Ala Met Leu Pro Asn
        275                 280                 285

Ala Ile Thr Ser Ser Leu Gly Ser Lys Val Lys Leu Leu Trp Lys Leu
    290                 295                 300

Thr Ser Ile Thr Lys Ser Asp Asp Lys Gly Tyr Val Leu Glu Tyr Glu
305                 310                 315                 320

Thr Pro Glu Gly Val Val Ser Val Gln Ala Lys Ser Val Ile Met Thr
                325                 330                 335

Ile Pro Ser Tyr Val Ala Ser Asn Ile Leu Arg Pro Leu Ser Ser Asp
            340                 345                 350

Ala Ala Asp Ala Leu Ser Arg Phe Tyr Tyr Pro Pro Val Ala Ala Val
        355                 360                 365

Thr Val Ser Tyr Pro Lys Glu Ala Ile Arg Lys Glu Cys Leu Ile Asp
    370                 375                 380

Gly Glu Leu Gln Gly Phe Gly Gln Leu His Pro Arg Ser Gln Gly Val
385                 390                 395                 400

Glu Thr Leu Gly Thr Ile Tyr Ser Ser Ser Leu Phe Pro Asn Arg Ala
                405                 410                 415

Pro Asp Gly Arg Val Leu Leu Thr Asn Val Ile Gly Gly Ala Thr Asn
            420                 425                 430

Thr Gly Ile Val Ser Lys Thr Glu Ser Glu Leu Val Glu Ala Val Asp
        435                 440                 445

Arg Asp Leu Arg Lys Met Leu Ile Asn Ser Thr Ala Val Asp Pro Leu
    450                 455                 460

Val Leu Gly Val Arg Val Trp Pro Gln Ala Ile Pro Gln Phe Leu Val
465                 470                 475                 480

Gly His Leu Asp Leu Leu Glu Ala Ala Lys Ala Ala Leu Asp Arg Gly
                485                 490                 495

Gly Tyr Asp Gly Leu Phe Leu Gly Gly Asn Tyr Val Ala Gly Val Ala
            500                 505                 510

Leu Gly Arg Cys Val Glu Gly Ala Tyr Glu Ser Ala Ser Gln Ile Ser
        515                 520                 525

Asp Phe Leu Thr Lys Tyr Ala Tyr Lys
    530                 535
```

<210> SEQ ID NO 28
<211> LENGTH: 537
<212> TYPE: PRT

-continued

```
<213> ORGANISM: Artificial sequence
<220> FEATURE:
<223> OTHER INFORMATION: Amino-acid sequence of PPO1 form corn mutant
      (ZmPPO1 L424S/Y426V)

<400> SEQUENCE: 28

Met Val Ala Ala Thr Ala Thr Ala Thr Ala Met Ala Thr Ala Ala Ser
1               5                   10                  15

Pro Leu Leu Asn Gly Thr Arg Ile Pro Ala Arg Leu Arg His Arg Gly
            20                  25                  30

Leu Ser Val Arg Cys Ala Ala Val Ala Gly Gly Ala Ala Glu Ala Pro
        35                  40                  45

Ala Ser Thr Gly Ala Arg Leu Ser Ala Asp Cys Val Val Gly Gly
    50                  55                  60

Gly Ile Ser Gly Leu Cys Thr Ala Gln Ala Leu Ala Thr Arg His Gly
65                  70                  75                  80

Val Gly Asp Val Leu Val Thr Glu Ala Arg Ala Arg Pro Gly Gly Asn
                85                  90                  95

Ile Thr Thr Val Glu Arg Pro Glu Glu Gly Tyr Leu Trp Glu Glu Gly
            100                 105                 110

Pro Asn Ser Phe Gln Pro Ser Asp Pro Val Leu Thr Met Ala Val Asp
        115                 120                 125

Ser Gly Leu Lys Asp Asp Leu Val Phe Gly Asp Pro Asn Ala Pro Arg
    130                 135                 140

Phe Val Leu Trp Glu Gly Lys Leu Arg Pro Val Pro Ser Lys Pro Ala
145                 150                 155                 160

Asp Leu Pro Phe Phe Asp Leu Met Ser Ile Pro Gly Lys Leu Arg Ala
                165                 170                 175

Gly Leu Gly Ala Leu Gly Ile Arg Pro Pro Pro Pro Gly Arg Glu Glu
            180                 185                 190

Ser Val Glu Glu Phe Val Arg Arg Asn Leu Gly Ala Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Arg Leu Glu Glu
225                 230                 235                 240

Thr Gly Gly Ser Ile Ile Gly Gly Thr Ile Lys Thr Ile Gln Glu Arg
                245                 250                 255

Ser Lys Asn Pro Lys Pro Pro Arg Asp Ala Arg Leu Pro Lys Pro Lys
            260                 265                 270

Gly Gln Thr Val Ala Ser Phe Arg Lys Gly Leu Ala Met Leu Pro Asn
        275                 280                 285

Ala Ile Thr Ser Ser Leu Gly Ser Lys Val Lys Leu Leu Trp Lys Leu
    290                 295                 300

Thr Ser Ile Thr Lys Ser Asp Asp Lys Gly Tyr Val Leu Glu Tyr Glu
305                 310                 315                 320

Thr Pro Glu Gly Val Val Ser Val Gln Ala Lys Ser Val Ile Met Thr
                325                 330                 335

Ile Pro Ser Tyr Val Ala Ser Asn Ile Leu Arg Pro Leu Ser Ser Asp
            340                 345                 350

Ala Ala Asp Ala Leu Ser Arg Phe Tyr Tyr Pro Pro Val Ala Ala Val
        355                 360                 365

Thr Val Ser Tyr Pro Lys Glu Ala Ile Arg Lys Glu Cys Leu Ile Asp
    370                 375                 380
```

```
Gly Glu Leu Gln Gly Phe Gly Gln Leu His Pro Arg Ser Gln Gly Val
385                 390                 395                 400

Glu Thr Leu Gly Thr Ile Tyr Ser Ser Ser Leu Phe Pro Asn Arg Ala
                405                 410                 415

Pro Asp Gly Arg Val Leu Leu Ser Asn Val Ile Gly Gly Ala Thr Asn
            420                 425                 430

Thr Gly Ile Val Ser Lys Thr Glu Ser Glu Leu Val Glu Ala Val Asp
        435                 440                 445

Arg Asp Leu Arg Lys Met Leu Ile Asn Ser Thr Ala Val Asp Pro Leu
    450                 455                 460

Val Leu Gly Val Arg Val Trp Pro Gln Ala Ile Pro Gln Phe Leu Val
465                 470                 475                 480

Gly His Leu Asp Leu Leu Glu Ala Ala Lys Ala Ala Leu Asp Arg Gly
                485                 490                 495

Gly Tyr Asp Gly Leu Phe Leu Gly Gly Asn Tyr Val Ala Gly Val Ala
            500                 505                 510

Leu Gly Arg Cys Val Glu Gly Ala Tyr Glu Ser Ala Ser Gln Ile Ser
        515                 520                 525

Asp Phe Leu Thr Lys Tyr Ala Tyr Lys
    530                 535
```

<210> SEQ ID NO 29
<211> LENGTH: 537
<212> TYPE: PRT
<213> ORGANISM: Artificial sequence
<220> FEATURE:
<223> OTHER INFORMATION: Amino-acid sequence of PPO1 from corn mutant (ZmPPO1 L424V/Y426L)

<400> SEQUENCE: 29

```
Met Val Ala Ala Thr Ala Thr Ala Thr Ala Met Ala Thr Ala Ala Ser
1               5                   10                  15

Pro Leu Leu Asn Gly Thr Arg Ile Pro Ala Arg Leu Arg His Arg Gly
            20                  25                  30

Leu Ser Val Arg Cys Ala Ala Val Ala Gly Gly Ala Ala Glu Ala Pro
        35                  40                  45

Ala Ser Thr Gly Ala Arg Leu Ser Ala Asp Cys Val Val Val Gly Gly
    50                  55                  60

Gly Ile Ser Gly Leu Cys Thr Ala Gln Ala Leu Ala Thr Arg His Gly
65                  70                  75                  80

Val Gly Asp Val Leu Val Thr Glu Ala Arg Ala Arg Pro Gly Gly Asn
                85                  90                  95

Ile Thr Thr Val Glu Arg Pro Glu Glu Gly Tyr Leu Trp Glu Glu Gly
            100                 105                 110

Pro Asn Ser Phe Gln Pro Ser Asp Pro Val Leu Thr Met Ala Val Asp
        115                 120                 125

Ser Gly Leu Lys Asp Asp Leu Val Phe Gly Asp Pro Asn Ala Pro Arg
    130                 135                 140

Phe Val Leu Trp Glu Gly Lys Leu Arg Pro Val Pro Ser Lys Pro Ala
145                 150                 155                 160

Asp Leu Pro Phe Phe Asp Leu Met Ser Ile Pro Gly Lys Leu Arg Ala
                165                 170                 175

Gly Leu Gly Ala Leu Gly Ile Arg Pro Pro Pro Pro Gly Arg Glu Glu
            180                 185                 190

Ser Val Glu Glu Phe Val Arg Arg Asn Leu Gly Ala Glu Val Phe Glu
        195                 200                 205
```

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Arg Leu Glu Glu
225                 230                 235                 240

Thr Gly Gly Ser Ile Ile Gly Gly Thr Ile Lys Thr Ile Gln Glu Arg
                245                 250                 255

Ser Lys Asn Pro Lys Pro Pro Arg Asp Ala Arg Leu Pro Lys Pro Lys
            260                 265                 270

Gly Gln Thr Val Ala Ser Phe Arg Lys Gly Leu Ala Met Leu Pro Asn
        275                 280                 285

Ala Ile Thr Ser Ser Leu Gly Ser Lys Val Lys Leu Leu Trp Lys Leu
    290                 295                 300

Thr Ser Ile Thr Lys Ser Asp Asp Lys Gly Tyr Val Leu Glu Tyr Glu
305                 310                 315                 320

Thr Pro Glu Gly Val Val Ser Val Gln Ala Lys Ser Val Ile Met Thr
                325                 330                 335

Ile Pro Ser Tyr Val Ala Ser Asn Ile Leu Arg Pro Leu Ser Ser Asp
            340                 345                 350

Ala Ala Asp Ala Leu Ser Arg Phe Tyr Tyr Pro Pro Val Ala Ala Val
        355                 360                 365

Thr Val Ser Tyr Pro Lys Glu Ala Ile Arg Lys Glu Cys Leu Ile Asp
    370                 375                 380

Gly Glu Leu Gln Gly Phe Gly Gln Leu His Pro Arg Ser Gln Gly Val
385                 390                 395                 400

Glu Thr Leu Gly Thr Ile Tyr Ser Ser Ser Leu Phe Pro Asn Arg Ala
                405                 410                 415

Pro Asp Gly Arg Val Leu Leu Val Asn Leu Ile Gly Gly Ala Thr Asn
            420                 425                 430

Thr Gly Ile Val Ser Lys Thr Glu Ser Glu Leu Val Glu Ala Val Asp
        435                 440                 445

Arg Asp Leu Arg Lys Met Leu Ile Asn Ser Thr Ala Val Asp Pro Leu
    450                 455                 460

Val Leu Gly Val Arg Val Trp Pro Gln Ala Ile Pro Gln Phe Leu Val
465                 470                 475                 480

Gly His Leu Asp Leu Leu Glu Ala Ala Lys Ala Ala Leu Asp Arg Gly
                485                 490                 495

Gly Tyr Asp Gly Leu Phe Leu Gly Gly Asn Tyr Val Ala Gly Val Ala
            500                 505                 510

Leu Gly Arg Cys Val Glu Gly Ala Tyr Glu Ser Ala Ser Gln Ile Ser
        515                 520                 525

Asp Phe Leu Thr Lys Tyr Ala Tyr Lys
    530                 535

<210> SEQ ID NO 30
<211> LENGTH: 537
<212> TYPE: PRT
<213> ORGANISM: Artificial sequence
<220> FEATURE:
<223> OTHER INFORMATION: Amino-acid sequence of PPO1 from corn mutant
      (ZmPPO1 L424W/Y426L)

<400> SEQUENCE: 30

Met Val Ala Ala Thr Ala Thr Ala Thr Ala Met Ala Thr Ala Ala Ser
1               5                   10                  15

Pro Leu Leu Asn Gly Thr Arg Ile Pro Ala Arg Leu Arg His Arg Gly

-continued

```
            20                  25                  30

Leu Ser Val Arg Cys Ala Ala Val Ala Gly Gly Ala Ala Glu Ala Pro
        35                  40                  45

Ala Ser Thr Gly Ala Arg Leu Ser Ala Asp Cys Val Val Val Gly Gly
    50                  55                  60

Gly Ile Ser Gly Leu Cys Thr Ala Gln Ala Leu Ala Thr Arg His Gly
65                  70                  75                  80

Val Gly Asp Val Leu Val Thr Glu Ala Arg Ala Arg Pro Gly Gly Asn
                85                  90                  95

Ile Thr Thr Val Glu Arg Pro Glu Glu Gly Tyr Leu Trp Glu Glu Gly
            100                 105                 110

Pro Asn Ser Phe Gln Pro Ser Asp Pro Val Leu Thr Met Ala Val Asp
        115                 120                 125

Ser Gly Leu Lys Asp Asp Leu Val Phe Gly Asp Pro Asn Ala Pro Arg
    130                 135                 140

Phe Val Leu Trp Glu Gly Lys Leu Arg Pro Val Pro Ser Lys Pro Ala
145                 150                 155                 160

Asp Leu Pro Phe Phe Asp Leu Met Ser Ile Pro Gly Lys Leu Arg Ala
                165                 170                 175

Gly Leu Gly Ala Leu Gly Ile Arg Pro Pro Pro Pro Gly Arg Glu Glu
            180                 185                 190

Ser Val Glu Glu Phe Val Arg Arg Asn Leu Gly Ala Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Arg Leu Glu Glu
225                 230                 235                 240

Thr Gly Gly Ser Ile Ile Gly Gly Thr Ile Lys Thr Ile Gln Glu Arg
                245                 250                 255

Ser Lys Asn Pro Lys Pro Pro Arg Asp Ala Arg Leu Pro Lys Pro Lys
            260                 265                 270

Gly Gln Thr Val Ala Ser Phe Arg Lys Gly Leu Ala Met Leu Pro Asn
        275                 280                 285

Ala Ile Thr Ser Ser Leu Gly Ser Lys Val Lys Leu Leu Trp Lys Leu
    290                 295                 300

Thr Ser Ile Thr Lys Ser Asp Asp Lys Gly Tyr Val Leu Glu Tyr Glu
305                 310                 315                 320

Thr Pro Glu Gly Val Val Ser Val Gln Ala Lys Ser Val Ile Met Thr
                325                 330                 335

Ile Pro Ser Tyr Val Ala Ser Asn Ile Leu Arg Pro Leu Ser Ser Asp
            340                 345                 350

Ala Ala Asp Ala Leu Ser Arg Phe Tyr Tyr Pro Pro Val Ala Ala Val
        355                 360                 365

Thr Val Ser Tyr Pro Lys Glu Ala Ile Arg Lys Glu Cys Leu Ile Asp
    370                 375                 380

Gly Glu Leu Gln Gly Phe Gly Gln Leu His Pro Arg Ser Gln Gly Val
385                 390                 395                 400

Glu Thr Leu Gly Thr Ile Tyr Ser Ser Ser Leu Phe Pro Asn Arg Ala
                405                 410                 415

Pro Asp Gly Arg Val Leu Leu Trp Asn Leu Ile Gly Gly Ala Thr Asn
            420                 425                 430

Thr Gly Ile Val Ser Lys Thr Glu Ser Glu Leu Val Glu Ala Val Asp
        435                 440                 445
```

```
Arg Asp Leu Arg Lys Met Leu Ile Asn Ser Thr Ala Val Asp Pro Leu
    450                 455                 460

Val Leu Gly Val Arg Val Trp Pro Gln Ala Ile Pro Gln Phe Leu Val
465                 470                 475                 480

Gly His Leu Asp Leu Leu Glu Ala Ala Lys Ala Ala Leu Asp Arg Gly
                485                 490                 495

Gly Tyr Asp Gly Leu Phe Leu Gly Gly Asn Tyr Val Ala Gly Val Ala
            500                 505                 510

Leu Gly Arg Cys Val Glu Gly Ala Tyr Glu Ser Ala Ser Gln Ile Ser
        515                 520                 525

Asp Phe Leu Thr Lys Tyr Ala Tyr Lys
    530                 535


<210> SEQ ID NO 31
<211> LENGTH: 537
<212> TYPE: PRT
<213> ORGANISM: Artificial sequence
<220> FEATURE:
<223> OTHER INFORMATION: Amino-acid sequence of PPO1 form corn mutant
      (ZmPPO1 L424S/Y426I)

<400> SEQUENCE: 31

Met Val Ala Ala Thr Ala Thr Ala Thr Ala Met Ala Thr Ala Ala Ser
1               5                   10                  15

Pro Leu Leu Asn Gly Thr Arg Ile Pro Ala Arg Leu Arg His Arg Gly
            20                  25                  30

Leu Ser Val Arg Cys Ala Ala Val Ala Gly Gly Ala Ala Glu Ala Pro
        35                  40                  45

Ala Ser Thr Gly Ala Arg Leu Ser Ala Asp Cys Val Val Val Gly Gly
    50                  55                  60

Gly Ile Ser Gly Leu Cys Thr Ala Gln Ala Leu Ala Thr Arg His Gly
65                  70                  75                  80

Val Gly Asp Val Leu Val Thr Glu Ala Arg Ala Arg Pro Gly Gly Asn
                85                  90                  95

Ile Thr Thr Val Glu Arg Pro Glu Glu Gly Tyr Leu Trp Glu Glu Gly
            100                 105                 110

Pro Asn Ser Phe Gln Pro Ser Asp Pro Val Leu Thr Met Ala Val Asp
        115                 120                 125

Ser Gly Leu Lys Asp Asp Leu Val Phe Gly Asp Pro Asn Ala Pro Arg
    130                 135                 140

Phe Val Leu Trp Glu Gly Lys Leu Arg Pro Val Pro Ser Lys Pro Ala
145                 150                 155                 160

Asp Leu Pro Phe Phe Asp Leu Met Ser Ile Pro Gly Lys Leu Arg Ala
                165                 170                 175

Gly Leu Gly Ala Leu Gly Ile Arg Pro Pro Pro Pro Gly Arg Glu Glu
            180                 185                 190

Ser Val Glu Glu Phe Val Arg Arg Asn Leu Gly Ala Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Arg Leu Glu Glu
225                 230                 235                 240

Thr Gly Gly Ser Ile Ile Gly Gly Thr Ile Lys Thr Ile Gln Glu Arg
                245                 250                 255

Ser Lys Asn Pro Lys Pro Pro Arg Asp Ala Arg Leu Pro Lys Pro Lys
```

```
            260                 265                 270

Gly Gln Thr Val Ala Ser Phe Arg Lys Gly Leu Ala Met Leu Pro Asn
        275                 280                 285

Ala Ile Thr Ser Ser Leu Gly Ser Lys Val Lys Leu Leu Trp Lys Leu
    290                 295                 300

Thr Ser Ile Thr Lys Ser Asp Asp Lys Gly Tyr Val Leu Glu Tyr Glu
305                 310                 315                 320

Thr Pro Glu Gly Val Val Ser Val Gln Ala Lys Ser Val Ile Met Thr
                325                 330                 335

Ile Pro Ser Tyr Val Ala Ser Asn Ile Leu Arg Pro Leu Ser Ser Asp
            340                 345                 350

Ala Ala Asp Ala Leu Ser Arg Phe Tyr Tyr Pro Pro Val Ala Ala Val
        355                 360                 365

Thr Val Ser Tyr Pro Lys Glu Ala Ile Arg Lys Glu Cys Leu Ile Asp
    370                 375                 380

Gly Glu Leu Gln Gly Phe Gly Gln Leu His Pro Arg Ser Gln Gly Val
385                 390                 395                 400

Glu Thr Leu Gly Thr Ile Tyr Ser Ser Ser Leu Phe Pro Asn Arg Ala
                405                 410                 415

Pro Asp Gly Arg Val Leu Leu Ser Asn Ile Ile Gly Gly Ala Thr Asn
            420                 425                 430

Thr Gly Ile Val Ser Lys Thr Glu Ser Glu Leu Val Glu Ala Val Asp
        435                 440                 445

Arg Asp Leu Arg Lys Met Leu Ile Asn Ser Thr Ala Val Asp Pro Leu
    450                 455                 460

Val Leu Gly Val Arg Val Trp Pro Gln Ala Ile Pro Gln Phe Leu Val
465                 470                 475                 480

Gly His Leu Asp Leu Leu Glu Ala Ala Lys Ala Ala Leu Asp Arg Gly
                485                 490                 495

Gly Tyr Asp Gly Leu Phe Leu Gly Gly Asn Tyr Val Ala Gly Val Ala
            500                 505                 510

Leu Gly Arg Cys Val Glu Gly Ala Tyr Glu Ser Ala Ser Gln Ile Ser
        515                 520                 525

Asp Phe Leu Thr Lys Tyr Ala Tyr Lys
    530                 535


<210> SEQ ID NO 32
<211> LENGTH: 537
<212> TYPE: PRT
<213> ORGANISM: Artificial sequence
<220> FEATURE:
<223> OTHER INFORMATION: Amino-acid sequence of PPO1 from oilseed rape
      mutant (BnPPO1-C5 L424S/Y426I)

<400> SEQUENCE: 32

Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Pro Asn Leu Arg Cys
            20                  25                  30

Ser Val Ser Gly Gly Ser Val Val Gly Gly Ser Ser Thr Ile Glu Gly
        35                  40                  45

Gly Arg Gly Gly Lys Thr Val Ala Ala Asp Cys Val Ile Val Gly Gly
    50                  55                  60

Gly Ile Ser Gly Leu Cys Ile Ala Gln Ala Leu Val Thr Lys His Pro
65                  70                  75                  80
```

-continued

```
Asp Ala Ala Lys Ser Val Met Val Thr Glu Ala Lys Asp Arg Val Gly
                85                  90                  95

Gly Asn Ile Ile Thr Arg Glu Glu Gln Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Ile Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ala
    210                 215                 220

Lys Leu Ser Met Lys Ala Ala Phe Gly Lys Val Trp Lys Leu Glu Glu
225                 230                 235                 240

Asn Gly Gly Ser Ile Ile Gly Gly Ala Phe Lys Ala Ile Gln Ala Arg
                245                 250                 255

Asn Lys Ala Pro Lys Thr Thr Arg Asp Pro Arg Leu Pro Lys Pro Lys
            260                 265                 270

Gly Gln Thr Val Gly Ser Phe Arg Lys Gly Leu Thr Met Leu Pro Asp
        275                 280                 285

Ala Ile Ser Ala Arg Leu Gly Asp Lys Val Lys Val Ser Trp Lys Leu
    290                 295                 300

Ser Ser Ile Ser Lys Leu Pro Ser Gly Gly Tyr Ser Leu Thr Tyr Glu
305                 310                 315                 320

Thr Pro Glu Gly Ile Val Thr Val Gln Ser Lys Ser Val Val Met Thr
                325                 330                 335

Val Pro Ser His Val Ala Ser Ser Leu Leu Arg Pro Leu Ser Asp Ser
            340                 345                 350

Ala Ala Glu Ala Leu Ser Lys Leu Tyr Tyr Pro Pro Val Ala Ala Val
        355                 360                 365

Ser Ile Ser Tyr Pro Lys Glu Ala Ile Arg Ser Glu Cys Leu Ile Asp
    370                 375                 380

Gly Glu Leu Lys Gly Phe Gly Gln Leu His Pro Arg Thr Gln Lys Val
385                 390                 395                 400

Glu Thr Leu Gly Thr Ile Tyr Ser Ser Ser Leu Phe Pro Asn Arg Ala
                405                 410                 415

Pro Pro Gly Arg Val Leu Leu Ser Asn Ile Ile Gly Gly Ala Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Ser Ser Thr Asp Pro Leu
    450                 455                 460

Val Leu Gly Val Lys Val Trp Pro Gln Ala Ile Pro Gln Phe Leu Ile
465                 470                 475                 480

Gly His Ile Asp Leu Val Asp Ala Ala Lys Ala Ser Leu Ser Ser Ser
                485                 490                 495

Gly His Glu Gly Leu Phe Leu Gly Gly Asn Tyr Val Ala Gly Val Ala
```

```
            500                 505                 510

Leu Gly Arg Cys Val Glu Gly Ala Tyr Glu Thr Ala Thr Gln Val Asn
        515                 520                 525

Asp Phe Met Ser Arg Tyr Ala Tyr Lys
    530                 535
```

<210> SEQ ID NO 33
<211> LENGTH: 536
<212> TYPE: PRT
<213> ORGANISM: Artificial sequence
<220> FEATURE:
<223> OTHER INFORMATION: Amino-acid sequence of PPO1 from oilseed rape mutant (BnPPO1-A10 L423S/Y425I)

<400> SEQUENCE: 33

```
Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Leu Asn Leu Arg Cys
            20                  25                  30

Ser Val Ser Gly Gly Ser Val Val Gly Ser Ser Thr Ile Glu Gly Gly
        35                  40                  45

Gly Gly Gly Lys Thr Val Thr Ala Asp Cys Val Ile Val Gly Gly Gly
    50                  55                  60

Ile Ser Gly Leu Cys Ile Ala Gln Ala Leu Val Thr Lys His Pro Asp
65                  70                  75                  80

Ala Ala Lys Asn Val Met Val Thr Glu Ala Lys Asp Arg Val Gly Gly
                85                  90                  95

Asn Ile Ile Thr Arg Glu Glu Gln Gly Phe Leu Trp Glu Glu Gly Pro
            100                 105                 110

Asn Ser Phe Gln Pro Ser Asp Pro Met Leu Thr Met Val Val Asp Ser
        115                 120                 125

Gly Leu Lys Asp Asp Leu Val Leu Gly Asp Pro Thr Ala Pro Arg Phe
    130                 135                 140

Val Leu Trp Asn Gly Lys Leu Arg Pro Val Pro Ser Lys Leu Thr Asp
145                 150                 155                 160

Leu Pro Phe Phe Asp Leu Met Ser Ile Gly Gly Lys Ile Arg Ala Gly
                165                 170                 175

Phe Gly Ala Ile Gly Ile Arg Pro Ser Pro Pro Gly Arg Glu Glu Ser
            180                 185                 190

Val Glu Glu Phe Val Arg Arg Asn Leu Gly Asp Glu Val Phe Glu Arg
        195                 200                 205

Leu Ile Glu Pro Phe Cys Ser Gly Val Tyr Ala Gly Asp Pro Ala Lys
    210                 215                 220

Leu Ser Met Lys Ala Ala Phe Gly Lys Val Trp Lys Leu Glu Glu Asn
225                 230                 235                 240

Gly Gly Ser Ile Ile Gly Gly Ala Phe Lys Ala Ile Gln Ala Lys Asn
                245                 250                 255

Lys Ala Pro Lys Thr Thr Arg Asp Pro Arg Leu Pro Lys Pro Lys Gly
            260                 265                 270

Gln Thr Val Gly Ser Phe Arg Lys Gly Leu Thr Met Leu Pro Glu Ala
        275                 280                 285

Ile Ser Ala Arg Leu Gly Asp Lys Val Lys Val Ser Trp Lys Leu Ser
    290                 295                 300

Ser Ile Thr Lys Leu Ala Ser Gly Glu Tyr Ser Leu Thr Tyr Glu Thr
305                 310                 315                 320
```

-continued

```
Pro Glu Gly Ile Val Thr Val Gln Ser Lys Ser Val Val Met Thr Val
                325                 330                 335

Pro Ser His Val Ala Ser Ser Leu Leu Arg Pro Leu Ser Asp Ser Ala
            340                 345                 350

Ala Glu Ala Leu Ser Lys Leu Tyr Tyr Pro Pro Val Ala Ala Val Ser
        355                 360                 365

Ile Ser Tyr Ala Lys Glu Ala Ile Arg Ser Glu Cys Leu Ile Asp Gly
    370                 375                 380

Glu Leu Lys Gly Phe Gly Gln Leu His Pro Arg Thr Gln Lys Val Glu
385                 390                 395                 400

Thr Leu Gly Thr Ile Tyr Ser Ser Ser Leu Phe Pro Asn Arg Ala Pro
                405                 410                 415

Pro Gly Arg Val Leu Leu Ser Asn Ile Ile Gly Gly Ala Thr Asn Thr
            420                 425                 430

Gly Ile Leu Ser Lys Ser Glu Gly Glu Leu Val Glu Ala Val Asp Arg
        435                 440                 445

Asp Leu Arg Lys Met Leu Ile Lys Pro Ser Ser Thr Asp Pro Leu Val
    450                 455                 460

Leu Gly Val Lys Leu Trp Pro Gln Ala Ile Pro Gln Phe Leu Ile Gly
465                 470                 475                 480

His Ile Asp Leu Val Asp Ala Ala Lys Ala Ser Leu Ser Ser Ser Gly
                485                 490                 495

His Glu Gly Leu Phe Leu Gly Gly Asn Tyr Val Ala Gly Val Ala Leu
            500                 505                 510

Gly Arg Cys Val Glu Gly Ala Tyr Glu Thr Ala Thr Gln Val Asn Asp
        515                 520                 525

Phe Met Ser Arg Tyr Ala Tyr Lys
    530                 535


<210> SEQ ID NO 34
<211> LENGTH: 558
<212> TYPE: PRT
<213> ORGANISM: Artificial sequence
<220> FEATURE:
<223> OTHER INFORMATION: Amino-acid sequence of PPO1 from peanut mutant
      (AhPPO1-A L445S/Y447I)

<400> SEQUENCE: 34

Met Pro Ala Met Leu Thr Leu Pro Asn Asp Thr Val Phe Leu Gln Asn
1               5                   10                  15

Thr Met His Ser Pro Thr Ser Ser Phe Ser Pro His Ser Pro Leu Ile
            20                  25                  30

Ile Pro Phe Pro Ser Pro Cys Arg His Pro Ser Thr Thr Lys Phe Pro
        35                  40                  45

Leu Ile Arg Cys Ser Leu Ala Gly Glu Ser Ser Thr Ala Ser Pro Ala
    50                  55                  60

Lys Pro Ala Ala Leu Pro Arg Ser Ala Val Gly Ala Ser Val Asp Cys
65                  70                  75                  80

Val Val Val Gly Gly Gly Ile Ser Gly Leu Cys Ile Ala Gln Ala Leu
                85                  90                  95

Ser Thr Lys His Ala Lys Ala Ala Ala Asn Val Val Val Thr Glu Ala
            100                 105                 110

Arg Asp Arg Val Gly Gly Asn Ile Thr Thr Ile Glu Arg Asp Gly Tyr
        115                 120                 125

Leu Trp Glu Glu Gly Pro Asn Ser Phe Gln Pro Ser Asp Pro Met Leu
    130                 135                 140
```

```
Thr Met Val Val Asp Ser Gly Leu Lys Asp Glu Leu Val Leu Gly Asp
145                 150                 155                 160

Pro Asn Ala Pro Arg Phe Val Leu Trp Asn Gly Glu Leu Arg Pro Val
                165                 170                 175

Pro Gly Lys Pro Thr Asp Leu Pro Phe Phe Asp Leu Met Ser Phe Gly
            180                 185                 190

Gly Lys Leu Arg Ala Gly Phe Gly Ala Leu Gly Ile Arg Pro Pro Pro
        195                 200                 205

Pro Gly His Glu Glu Ser Val Glu Glu Phe Val Arg Arg Asn Leu Gly
    210                 215                 220

Asp Glu Val Phe Glu Arg Leu Ile Glu Pro Phe Cys Ser Gly Val Tyr
225                 230                 235                 240

Ala Gly Asp Pro Ser Lys Leu Ser Met Lys Ala Ala Phe Gly Lys Val
                245                 250                 255

Trp Arg Leu Glu Gln Asn Gly Gly Ser Ile Ile Gly Gly Thr Phe Lys
            260                 265                 270

Ala Ile Gln Glu Arg Lys Ser Thr Ser Lys Pro Pro Arg Asp Pro Arg
        275                 280                 285

Leu Pro Thr Pro Lys Gly Gln Thr Val Gly Ser Phe Arg Lys Gly Leu
    290                 295                 300

Thr Met Leu Pro Glu Ala Ile Ser Ala Lys Leu Gly Asn Lys Val Lys
305                 310                 315                 320

Leu Ser Trp Lys Leu Leu Gly Ile Ser Lys Leu Asp Ser Gly Glu Tyr
                325                 330                 335

Ser Leu Thr Tyr Asp Thr Pro Glu Gly Val Val Ser Leu Gln Thr Lys
            340                 345                 350

Ser Val Val Met Thr Ile Pro Ser His Val Ala Ser Thr Leu Leu Arg
        355                 360                 365

Ser Ile Ser Asp Ala Ala Ala Asp Ala Leu Ser Lys Phe Tyr Tyr Pro
    370                 375                 380

Pro Val Ala Ala Val Ser Val Ser Tyr Pro Lys Glu Ala Ile Arg Ser
385                 390                 395                 400

Glu Cys Leu Ile Asp Gly Glu Leu Lys Gly Phe Gly Gln Leu His Pro
                405                 410                 415

Arg Thr Gln Gly Val Glu Thr Leu Gly Thr Ile Tyr Ser Ser Ser Leu
            420                 425                 430

Phe Pro Asn Arg Ala Pro Asp Gly Arg Val Leu Leu Ser Asn Ile Ile
        435                 440                 445

Gly Gly Ala Thr Asn Pro Gly Ile Leu Ser Lys Thr Asp Ser Glu Leu
    450                 455                 460

Val Glu Ala Val Asp Arg Asp Leu Arg Lys Met Leu Ile Asn Pro Asn
465                 470                 475                 480

Ala Gly Asp Pro Phe Ala Leu Gly Val Arg Val Trp Pro Gln Ala Ile
                485                 490                 495

Pro Gln Phe Leu Val Gly His Leu Asp Leu Leu Asp Ile Ala Lys Ser
            500                 505                 510

Ser Leu Lys Asn Thr Gly Phe Glu Gly Leu Phe Leu Gly Gly Asn Tyr
        515                 520                 525

Val Ser Gly Val Ala Leu Gly Arg Cys Val Glu Gly Ala Tyr Glu Ile
    530                 535                 540

Ala Ala Glu Val Asp Asp Phe Leu Ala Gln Lys Val Tyr Lys
545                 550                 555
```

-continued

<210> SEQ ID NO 35
<211> LENGTH: 552
<212> TYPE: PRT
<213> ORGANISM: Artificial sequence
<220> FEATURE:
<223> OTHER INFORMATION: Amino-acid sequence of PPO1 from peanut mutant
(AhPPO1-B L439S/Y441I)

<400> SEQUENCE: 35

```
Met Ser Ala Met Leu Thr Leu Pro Asn Asp Thr Val Phe Leu Gln Asn
1               5                   10                  15

Thr Met His Ser Pro Thr Ser Ser Phe Ser Pro His Ser Pro Leu Ile
            20                  25                  30

Ile Pro Phe Pro Ser Pro Cys Arg His Pro Ser Thr Thr Lys Phe Pro
        35                  40                  45

Leu Ile Arg Cys Ser Leu Ala Gly Glu Ser Ser Thr Ala Ser Leu Pro
    50                  55                  60

Arg Ser Ala Val Gly Ala Ser Val Asp Cys Val Val Val Gly Gly Gly
65                  70                  75                  80

Ile Ser Gly Leu Cys Ile Ala Gln Ala Leu Ser Thr Lys His Ala Lys
                85                  90                  95

Ala Ala Ala Asn Val Val Val Thr Glu Ala Arg Asp Arg Val Gly Gly
            100                 105                 110

Asn Ile Thr Thr Val Glu Arg Asp Gly Tyr Leu Trp Glu Glu Gly Pro
        115                 120                 125

Asn Ser Phe Gln Pro Ser Asp Pro Met Leu Thr Met Val Val Asp Ser
    130                 135                 140

Gly Leu Lys Asp Glu Leu Val Leu Gly Asp Pro Asn Ala Pro Arg Phe
145                 150                 155                 160

Val Leu Trp Asn Gly Arg Leu Arg Pro Val Pro Gly Lys Pro Thr Asp
                165                 170                 175

Leu Pro Phe Phe Asp Leu Met Ser Phe Gly Gly Lys Leu Arg Ala Gly
            180                 185                 190

Phe Gly Ala Leu Gly Ile Arg Pro Pro Pro Pro Gly His Glu Glu Ser
        195                 200                 205

Val Glu Glu Phe Val Arg Arg Asn Leu Gly Asp Glu Val Phe Glu Arg
    210                 215                 220

Leu Ile Glu Pro Phe Cys Ser Gly Val Tyr Ala Gly Asp Pro Ser Lys
225                 230                 235                 240

Leu Ser Met Lys Ala Ala Phe Gly Lys Val Trp Arg Leu Glu Gln Asn
                245                 250                 255

Gly Gly Ser Ile Ile Gly Gly Thr Phe Lys Ala Ile Gln Glu Arg Lys
            260                 265                 270

Ser Thr Ser Lys Pro Pro Arg Asp Pro Arg Leu Pro Thr Pro Lys Gly
        275                 280                 285

Gln Thr Val Gly Ser Phe Arg Lys Gly Leu Ile Met Leu Pro Glu Ala
    290                 295                 300

Ile Ser Ala Lys Leu Gly Asn Lys Val Lys Leu Ser Trp Lys Leu Leu
305                 310                 315                 320

Gly Ile Ser Lys Leu Asp Ser Gly Glu Tyr Ser Leu Thr Tyr Asp Thr
                325                 330                 335

Pro Glu Gly Val Val Ser Leu Gln Thr Lys Ser Val Val Met Thr Ile
            340                 345                 350

Pro Ser His Val Ala Ser Thr Leu Leu Arg Ser Ile Ser Glu Thr Ala
        355                 360                 365
```

```
Ala Asp Ala Leu Ser Lys Phe Tyr Tyr Pro Pro Val Ala Ala Val Ser
    370                 375                 380

Val Ser Tyr Pro Lys Glu Ala Ile Arg Ser Glu Cys Leu Ile Asp Gly
385                 390                 395                 400

Glu Leu Lys Gly Phe Gly Gln Leu His Pro Arg Thr Gln Gly Val Glu
                405                 410                 415

Thr Leu Gly Thr Ile Tyr Ser Ser Ser Leu Phe Pro Asn Arg Ala Pro
            420                 425                 430

Asp Gly Arg Val Leu Leu Ser Asn Ile Ile Gly Gly Ala Thr Asn Pro
        435                 440                 445

Gly Ile Leu Ser Lys Thr Asp Ser Glu Leu Val Glu Ala Val Asp Arg
    450                 455                 460

Asp Leu Arg Lys Met Leu Ile Asn Pro Asn Ala Gly Asp Pro Phe Ala
465                 470                 475                 480

Leu Gly Val Arg Val Trp Pro Gln Ala Ile Pro Gln Phe Leu Val Gly
                485                 490                 495

His Leu Asp Leu Leu Asp Ile Ala Lys Ser Ser Leu Lys Asn Thr Gly
            500                 505                 510

Phe Glu Gly Leu Phe Leu Gly Gly Asn Tyr Val Ser Gly Val Ala Leu
        515                 520                 525

Gly Arg Cys Val Glu Gly Ala Tyr Glu Ile Ala Ala Glu Val Asp Asp
    530                 535                 540

Phe Leu Ala Gln Lys Val Tyr Lys
545                 550
```

<210> SEQ ID NO 36
<211> LENGTH: 543
<212> TYPE: PRT
<213> ORGANISM: Artificial sequence
<220> FEATURE:
<223> OTHER INFORMATION: Amino-acid sequence of PPO1 from soybean mutant (GmPPO1 L430S/Y432I)

<400> SEQUENCE: 36

```
Met Val Ser Val Phe Asn Glu Ile Leu Phe Pro Pro Asn Gln Thr Leu
1               5                   10                  15

Leu Arg Pro Ser Leu His Ser Pro Thr Ser Phe Phe Thr Ser Pro Thr
            20                  25                  30

Arg Lys Phe Pro Arg Ser Arg Pro Asn Pro Ile Leu Arg Cys Ser Ile
        35                  40                  45

Ala Glu Glu Ser Thr Ala Ser Pro Pro Lys Thr Arg Asp Ser Ala Pro
    50                  55                  60

Val Asp Cys Val Val Val Gly Gly Gly Val Ser Gly Leu Cys Ile Ala
65                  70                  75                  80

Gln Ala Leu Ala Thr Lys His Ala Asn Ala Asn Val Val Val Thr Glu
                85                  90                  95

Ala Arg Asp Arg Val Gly Gly Asn Ile Thr Thr Met Glu Arg Asp Gly
            100                 105                 110

Tyr Leu Trp Glu Glu Gly Pro Asn Ser Phe Gln Pro Ser Asp Pro Met
        115                 120                 125

Leu Thr Met Val Val Asp Ser Gly Leu Lys Asp Glu Leu Val Leu Gly
    130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
```

-continued

```
                165                 170                 175

Gly Gly Lys Ile Arg Ala Gly Phe Gly Ala Leu Gly Ile Arg Pro Pro
            180                 185                 190

Pro Pro Gly His Glu Glu Ser Val Glu Glu Phe Val Arg Arg Asn Leu
        195                 200                 205

Gly Asp Glu Val Phe Glu Arg Leu Ile Glu Pro Phe Cys Ser Gly Val
    210                 215                 220

Tyr Ala Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
                245                 250                 255

Lys Ala Ile Gln Glu Arg Asn Gly Ala Ser Lys Pro Pro Arg Asp Pro
            260                 265                 270

Arg Leu Pro Lys Pro Lys Gly Gln Thr Val Gly Ser Phe Arg Lys Gly
        275                 280                 285

Leu Thr Met Leu Pro Asp Ala Ile Ser Ala Arg Leu Gly Asn Lys Val
    290                 295                 300

Lys Leu Ser Trp Lys Leu Ser Ser Ile Ser Lys Leu Asp Ser Gly Glu
305                 310                 315                 320

Tyr Ser Leu Thr Tyr Glu Thr Pro Glu Gly Val Val Ser Leu Gln Cys
                325                 330                 335

Lys Thr Val Val Leu Thr Ile Pro Ser Tyr Val Ala Ser Thr Leu Leu
            340                 345                 350

Arg Pro Leu Ser Ala Ala Ala Ala Asp Ala Leu Ser Lys Phe Tyr Tyr
        355                 360                 365

Pro Pro Val Ala Ala Val Ser Ile Ser Tyr Pro Lys Glu Ala Ile Arg
    370                 375                 380

Ser Glu Cys Leu Ile Asp Gly Glu Leu Lys Gly Phe Gly Gln Leu His
385                 390                 395                 400

Pro Arg Ser Gln Gly Val Glu Thr Leu Gly Thr Ile Tyr Ser Ser Ser
                405                 410                 415

Leu Phe Pro Asn Arg Ala Pro Pro Gly Arg Val Leu Leu Ser Asn Ile
            420                 425                 430

Ile Gly Gly Ala Thr Asn Thr Gly Ile Leu Ser Lys Thr Asp Ser Glu
        435                 440                 445

Leu Val Glu Thr Val Asp Arg Asp Leu Arg Lys Ile Leu Ile Asn Pro
    450                 455                 460

Asn Ala Gln Asp Pro Phe Val Val Gly Val Arg Leu Trp Pro Gln Ala
465                 470                 475                 480

Ile Pro Gln Phe Leu Val Gly His Leu Asp Leu Leu Asp Val Ala Lys
                485                 490                 495

Ala Ser Ile Arg Asn Thr Gly Phe Glu Gly Leu Phe Leu Gly Gly Asn
            500                 505                 510

Tyr Val Ser Gly Val Ala Leu Gly Arg Cys Val Glu Gly Ala Tyr Glu
        515                 520                 525

Val Ala Ala Glu Val Asn Asp Phe Leu Thr Asn Arg Val Tyr Lys
    530                 535                 540
```

<210> SEQ ID NO 37
<211> LENGTH: 536
<212> TYPE: PRT
<213> ORGANISM: Artificial sequence
<220> FEATURE:
<223> OTHER INFORMATION: Amino-acid sequence of PPO1 from sorghum mutant
(SbPPO1 L423S/Y425I)

<400> SEQUENCE: 37

```
Met Val Ala Ala Ala Ala Met Ala Thr Ala Ala Ser Ala Ala Ala Pro
1               5                   10                  15

Leu Leu Asn Gly Thr Arg Arg Pro Ala Arg Leu Arg Arg Arg Gly Leu
            20                  25                  30

Arg Val Arg Cys Ala Ala Val Ala Gly Gly Ala Ala Glu Ala Pro Ala
        35                  40                  45

Ser Thr Gly Ala Arg Leu Ser Ala Asp Cys Val Val Val Gly Gly Gly
    50                  55                  60

Ile Ser Gly Leu Cys Thr Ala Gln Ala Leu Ala Thr Arg His Gly Val
65                  70                  75                  80

Gly Glu Val Leu Val Thr Glu Ala Arg Ala Arg Pro Gly Gly Asn Ile
                85                  90                  95

Thr Thr Val Glu Arg Pro Glu Glu Gly Tyr Leu Trp Glu Glu Gly Pro
            100                 105                 110

Asn Ser Phe Gln Pro Ser Asp Pro Val Leu Ser Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Ala Asp
145                 150                 155                 160

Leu Pro Phe Phe Asp Leu Met Ser Ile Pro Gly Lys Leu Arg Ala Gly
                165                 170                 175

Leu Gly Ala Leu Gly Ile Arg Pro Pro Pro Pro Gly Arg Glu Glu Ser
            180                 185                 190

Val Glu Glu Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
    210                 215                 220

Leu Ser Met Lys Ala Ala Phe Gly Lys Val Trp Arg Leu Glu Glu Ala
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Lys Pro Lys Gly
            260                 265                 270

Gln Thr Val Ala Ser Phe Arg Lys Gly Leu Ala Met Leu Pro Asn Ala
        275                 280                 285

Ile Thr Ser Ser Leu Gly Ser Lys Val Lys Leu Ser Trp Lys Leu Thr
    290                 295                 300

Ser Ile Thr Lys Ser Asp Gly Lys Gly Tyr Val Leu Glu Tyr Glu Thr
305                 310                 315                 320

Pro Glu Gly Val Val Leu Val Gln Ala Lys Ser Val Ile Met Thr Ile
                325                 330                 335

Pro Ser Tyr Val Ala Ser Asp Ile Leu Arg Pro Leu Ser Gly Asp Ala
            340                 345                 350

Ala Asp Ala Leu Ser Arg Phe Tyr Tyr Pro Pro Val Ala Ala Val Thr
        355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
```

-continued

```
                405                 410                 415

Ala Gly Arg Val Leu Leu Ser Asn Ile Ile Gly Gly Ala Thr Asn Thr
            420                 425                 430

Gly Ile Val Ser Lys Thr Glu Ser Glu Leu Val Glu Ala Val Asp Arg
        435                 440                 445

Asp Leu Arg Lys Met Leu Ile Asn Ser Thr Ala Val Asp Pro Leu Val
    450                 455                 460

Leu Gly Val Arg Val Trp Pro Gln Ala Ile Pro Gln Phe Leu Val Gly
465                 470                 475                 480

His Leu Asp Leu Leu Glu Val Ala Lys Ser Ala Leu Asp Gln Gly Gly
                485                 490                 495

Tyr Asp Gly Leu Phe Leu Gly Gly Asn Tyr Val Ala Gly Val Ala Leu
            500                 505                 510

Gly Arg Cys Ile Glu Gly Ala Tyr Glu Ser Ala Ala Gln Ile Tyr Asp
        515                 520                 525

Phe Leu Thr Lys Tyr Ala Tyr Lys
    530                 535


<210> SEQ ID NO 38
<211> LENGTH: 531
<212> TYPE: PRT
<213> ORGANISM: Artificial sequence
<220> FEATURE:
<223> OTHER INFORMATION: Amino-acid sequence of PPO1 form wheat mutant
      (TaPPO1-A L418S/Y420I)

<400> SEQUENCE: 38

Met Ala Gly Ala Thr Met Ala Thr Ala Thr Val Thr Ala Ala Ser Pro
1               5                   10                  15

Leu Arg Gly Arg Val Thr Gly Arg Pro Arg Arg Val Arg Thr Arg Cys
            20                  25                  30

Ala Ala Ala Ser Gly Ala Thr Glu Thr Pro Ala Ala Pro Gly Val Arg
        35                  40                  45

Leu Ser Ala Glu Cys Val Ile Val Gly Ala Gly Ile Ser Gly Leu Cys
    50                  55                  60

Thr Ala Gln Ala Leu Ala Thr Arg Tyr Gly Val Ser Asp Leu Leu Val
65                  70                  75                  80

Thr Glu Ala Arg Asp Arg Pro Gly Gly Asn Ile Thr Thr Val Glu Arg
                85                  90                  95

Pro Asp Glu Gly Tyr Leu Trp Glu Glu Gly Pro Asn Ser Phe Gln Pro
            100                 105                 110

Ser Asp Pro Val Leu Thr Met Ala Val Asp Ser Gly Leu Lys Asp Asp
        115                 120                 125

Leu Val Phe Gly Asp Pro Asn Ala Pro Arg Phe Val Leu Trp Glu Gly
    130                 135                 140

Lys Leu Arg Pro Val Pro Ser Lys Pro Gly Asp Leu Pro Phe Phe Ser
145                 150                 155                 160

Leu Met Ser Ile Pro Gly Lys Leu Arg Ala Gly Leu Gly Ala Leu Gly
                165                 170                 175

Ile Arg Pro Pro Pro Pro Gly Arg Glu Glu Ser Val Glu Glu Phe Val
            180                 185                 190

Arg Arg Asn Leu Gly Ala Glu Val Phe Glu Arg Leu Ile Glu Pro Phe
        195                 200                 205

Cys Ser Gly Val Tyr Ala Gly Asp Pro Ser Lys Leu Ser Met Lys Ala
    210                 215                 220
```

-continued

```
Ala Phe Gly Lys Val Trp Arg Leu Glu Glu Ile Gly Gly Ser Ile Ile
225                 230                 235                 240

Gly Gly Thr Ile Lys Ala Ile Gln Asp Lys Gly Lys Asn Pro Lys Pro
                245                 250                 255

Pro Arg Asp Pro Arg Leu Pro Ala Pro Lys Gly Gln Thr Val Ala Ser
            260                 265                 270

Phe Arg Lys Gly Leu Ala Met Leu Pro Asn Ala Ile Ala Ser Arg Leu
        275                 280                 285

Gly Ser Lys Val Lys Leu Ser Trp Lys Leu Thr Ser Ile Thr Lys Ala
    290                 295                 300

Asp Asn Gln Gly Tyr Val Leu Gly Tyr Glu Thr Pro Glu Gly Leu Val
305                 310                 315                 320

Ser Val Gln Ala Lys Ser Val Ile Met Thr Ile Pro Ser Tyr Val Ala
                325                 330                 335

Ser Asp Ile Leu Arg Pro Leu Ser Ile Asp Ala Ala Asp Ala Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Ser Asn Ile Ile Gly Gly Ser Thr Asn Thr Gly Ile Val Ser Lys
            420                 425                 430

Thr Glu Ser Asp Leu Val Glu Ala Val Asp Arg Asp Leu Arg Lys Met
        435                 440                 445

Leu Ile Asn Pro Arg Ala Ala Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Ala Ala Ala Lys Ser Ala Leu Gly Arg Gly Gly Tyr Asp Gly Leu Phe
                485                 490                 495

Leu Gly Gly Asn Tyr Val Ala Gly Val Ala Leu Gly Arg Cys Ile Glu
            500                 505                 510

Gly Ala Tyr Glu Ser Ala Ser Gln Val Ser Asp Phe Leu Thr Lys Tyr
        515                 520                 525

Ala Tyr Lys
    530
```

<210> SEQ ID NO 39
<211> LENGTH: 531
<212> TYPE: PRT
<213> ORGANISM: Artificial sequence
<220> FEATURE:
<223> OTHER INFORMATION: Amino-acid sequence of PPO1 from wheat mutant (TaPPO1-B L418S/Y420I)

<400> SEQUENCE: 39

```
Met Ala Gly Ala Thr Met Ala Thr Ala Thr Val Ala Ala Ala Ser Pro
1               5                   10                  15

Leu Arg Gly Arg Val Thr Gly Arg Pro His Arg Val Arg Pro Arg Cys
            20                  25                  30

Ala Thr Ala Ser Ser Ala Thr Glu Thr Pro Ala Ala Pro Gly Val Arg
        35                  40                  45
```

-continued

```
Leu Ser Ala Glu Cys Val Ile Val Gly Ala Gly Ile Ser Gly Leu Cys
    50                  55                  60

Thr Ala Gln Ala Leu Ala Thr Arg Tyr Gly Val Ser Asp Leu Leu Val
65                  70                  75                  80

Thr Glu Ala Arg Asp Arg Pro Gly Gly Asn Ile Thr Thr Val Glu Arg
                85                  90                  95

Pro Asp Glu Gly Tyr Leu Trp Glu Glu Gly Pro Asn Ser Phe Gln Pro
            100                 105                 110

Ser Asp Pro Val Leu Thr Met Ala Val Asp Ser Gly Leu Lys Asp Asp
        115                 120                 125

Leu Val Phe Gly Asp Pro Asn Ala Pro Arg Phe Val Leu Trp Glu Gly
    130                 135                 140

Lys Leu Arg Pro Val Pro Ser Lys Pro Gly Asp Leu Pro Phe Phe Ser
145                 150                 155                 160

Leu Met Ser Ile Pro Gly Lys Leu Arg Ala Gly Leu Gly Ala Leu Gly
                165                 170                 175

Ile Arg Pro Pro Pro Pro Gly Arg Glu Glu Ser Val Glu Glu Phe Val
            180                 185                 190

Arg Arg Asn Leu Gly Ala Glu Val Phe Glu Arg Leu Ile Glu Pro Phe
        195                 200                 205

Cys Ser Gly Val Tyr Ala Gly Asp Pro Ser Lys Leu Ser Met Lys Ala
    210                 215                 220

Ala Phe Gly Lys Val Trp Arg Leu Glu Glu Ile Gly Gly Ser Ile Ile
225                 230                 235                 240

Gly Gly Thr Ile Lys Ala Ile Gln Asp Lys Gly Lys Asn Pro Lys Pro
                245                 250                 255

Pro Arg Asp Pro Arg Leu Pro Ala Pro Lys Gly Gln Thr Val Ala Ser
            260                 265                 270

Phe Arg Lys Gly Leu Ala Met Leu Pro Asn Ala Ile Ala Ser Arg Leu
        275                 280                 285

Gly Ser Lys Val Lys Leu Ser Trp Lys Leu Thr Ser Ile Thr Lys Ala
    290                 295                 300

Asp Asn Gln Gly Tyr Val Leu Gly Tyr Glu Thr Pro Glu Gly Leu Val
305                 310                 315                 320

Ser Val Gln Ala Lys Ser Val Ile Met Thr Ile Pro Ser Tyr Val Ala
                325                 330                 335

Ser Asp Ile Leu Arg Pro Leu Ser Ile Asp Ala Ala Asp Ala Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Ser Asn Ile Ile Gly Gly Ser Thr Asn Thr Gly Ile Val Ser Lys
            420                 425                 430

Thr Glu Ser Asp Leu Val Gly Ala Val Asp Arg Asp Leu Arg Lys Met
        435                 440                 445

Leu Ile Asn Pro Arg Ala Ala Asp Pro Leu Ala Leu Gly Val Arg Val
    450                 455                 460
```

-continued

```
Trp Pro Gln Ala Ile Pro Gln Phe Leu Ile Gly His Leu Asp Arg Leu
465                 470                 475                 480

Ala Ala Ala Lys Ser Ala Leu Gly Gln Gly Gly Tyr Asp Gly Leu Phe
                485                 490                 495

Leu Gly Gly Asn Tyr Val Ala Gly Val Ala Leu Gly Arg Cys Ile Glu
            500                 505                 510

Gly Ala Tyr Glu Ser Ala Ser Gln Val Ser Asp Phe Leu Thr Lys Tyr
        515                 520                 525

Ala Tyr Lys
    530


<210> SEQ ID NO 40
<211> LENGTH: 531
<212> TYPE: PRT
<213> ORGANISM: Artificial sequence
<220> FEATURE:
<223> OTHER INFORMATION: Amino-acid sequence of PPO1 form wheat mutant
      (TaPPO1-D L418S/Y420I)

<400> SEQUENCE: 40

Met Ala Gly Ala Thr Met Ala Thr Ala Thr Val Thr Ala Ala Ser Pro
1               5                   10                  15

Leu Arg Gly Arg Val Thr Gly Arg Pro Arg Arg Val Arg Pro Arg Cys
            20                  25                  30

Ala Ala Ala Ser Gly Ala Thr Glu Thr Pro Ala Ala Pro Gly Val Arg
        35                  40                  45

Leu Ser Ala Asp Cys Val Ile Val Gly Ala Gly Ile Ser Gly Leu Cys
    50                  55                  60

Thr Ala Gln Ala Leu Ala Thr Arg Tyr Gly Val Gly Asp Leu Leu Ile
65                  70                  75                  80

Thr Glu Ala Arg Asp Arg Pro Gly Gly Asn Ile Thr Thr Val Glu Arg
                85                  90                  95

Pro Asp Glu Gly Tyr Leu Trp Glu Glu Gly Pro Asn Ser Phe Gln Pro
            100                 105                 110

Ser Asp Pro Val Leu Thr Met Ala Val Asp Ser Gly Leu Lys Asp Asp
        115                 120                 125

Leu Val Phe Gly Asp Pro Asn Ala Pro Arg Phe Val Leu Trp Glu Gly
    130                 135                 140

Lys Leu Arg Pro Val Pro Ser Lys Pro Gly Asp Leu Pro Phe Phe Ser
145                 150                 155                 160

Leu Met Ser Ile Pro Gly Lys Leu Arg Ala Gly Leu Gly Ala Leu Gly
                165                 170                 175

Ile Arg Pro Pro Pro Pro Gly Arg Glu Glu Ser Val Glu Glu Phe Val
            180                 185                 190

Arg Arg Asn Leu Gly Ala Glu Val Phe Glu Arg Leu Ile Glu Pro Phe
        195                 200                 205

Cys Ser Gly Val Tyr Ala Gly Asp Pro Ser Lys Leu Ser Met Lys Ala
    210                 215                 220

Ala Phe Gly Lys Val Trp Arg Leu Glu Glu Ile Gly Gly Ser Ile Ile
225                 230                 235                 240

Gly Gly Thr Ile Lys Ala Ile Gln Asp Lys Gly Lys Asn Pro Lys Pro
                245                 250                 255

Pro Arg Asp Pro Arg Leu Pro Ala Pro Lys Gly Gln Thr Val Ala Ser
            260                 265                 270

Phe Arg Lys Gly Leu Ala Met Leu Pro Asn Ala Ile Ala Ser Arg Leu
        275                 280                 285
```

```
Gly Ser Lys Val Lys Leu Ser Trp Lys Leu Thr Ser Ile Thr Lys Ala
    290                 295                 300

Asp Asn Gln Gly Tyr Val Leu Gly Tyr Glu Thr Pro Glu Gly Leu Val
305                 310                 315                 320

Ser Val Gln Ala Lys Ser Val Ile Met Thr Ile Pro Ser Tyr Val Ala
                325                 330                 335

Ser Asp Ile Leu Arg Pro Leu Ser Ile Asp Ala Ala Asp Ala Leu Ser
            340                 345                 350

Lys Phe Tyr Tyr Pro Pro Val Ala Ala Val Thr Val Ser Tyr Pro Lys
        355                 360                 365

Glu Ala Ile Arg Lys Glu Cys Leu Ile Asp Gly Glu Leu Gln Gly Phe
    370                 375                 380

Gly Gln Leu His Pro Arg Ser Gln Gly Val Glu Thr Leu Gly Thr Ile
385                 390                 395                 400

Tyr Ser Ser Ser Leu Phe Pro Asn Arg Ala Pro Ala Gly Arg Val Leu
                405                 410                 415

Leu Ser Asn Ile Ile Gly Gly Ser Thr Asn Thr Gly Ile Val Ser Lys
            420                 425                 430

Thr Glu Ser Asp Leu Val Glu Ala Val Asp Ser Asp Leu Arg Lys Met
        435                 440                 445

Leu Ile Asn Pro Arg Ala Ala Asp Pro Leu Ala Leu Gly Val Arg Val
    450                 455                 460

Trp Pro Gln Ala Ile Pro Gln Phe Leu Ile Gly His Leu Asp Arg Leu
465                 470                 475                 480

Ala Ala Ala Lys Ser Ala Leu Gly Arg Gly Gly Tyr Asp Gly Leu Phe
                485                 490                 495

Leu Gly Gly Asn Tyr Val Ala Gly Val Ala Leu Gly Arg Cys Ile Glu
            500                 505                 510

Gly Ala Tyr Glu Ser Ala Ser Gln Val Ser Asp Phe Leu Thr Lys Tyr
        515                 520                 525

Ala Tyr Lys
    530
```

<210> SEQ ID NO 41
<211> LENGTH: 558
<212> TYPE: PRT
<213> ORGANISM: Artificial sequence
<220> FEATURE:
<223> OTHER INFORMATION: Amino-acid sequence of PPO1 form tomato mutant (SlPPO1 L445S/Y447I)

<400> SEQUENCE: 41

```
Met Thr Thr Thr Ala Val Val Asn His Pro Ser Ile Phe Thr His Arg
1               5                   10                  15

Ser Pro Leu Pro Ser Pro Ser Ser Ser Ser Ser Ser Ser Pro Ser Phe
            20                  25                  30

Leu Phe Leu Asn Arg Thr Asn Phe Ile Pro Tyr Phe Ser Thr Ser Lys
        35                  40                  45

Arg Ser Ser Val Asn Cys Asn Gly Trp Arg Thr Arg Cys Ser Val Ala
    50                  55                  60

Lys Asn Tyr Thr Val Pro Pro Ser Glu Val Asp Gly Asn Gln Leu Pro
65                  70                  75                  80

Glu Leu Asp Cys Val Val Val Gly Ala Gly Ile Ser Gly Leu Cys Ile
                85                  90                  95

Ala Lys Val Ile Ser Ala Asn Tyr Pro Asn Leu Met Val Thr Glu Ala
```

-continued

```
            100                 105                 110

Arg Asp Arg Ala Gly Gly Asn Ile Thr Thr Val Glu Arg Asp Gly Tyr
        115                 120                 125

Leu Trp Glu Glu Gly Pro Asn Ser Phe Gln Pro Ser Asp Pro Met Leu
    130                 135                 140

Thr Met Ala Val Asp Cys Gly Leu Lys Asp Asp Leu Val Leu Gly Asp
145                 150                 155                 160

Pro Asp Ala Pro Arg Phe Val Leu Trp Lys Asp Lys Leu Arg Pro Val
                165                 170                 175

Pro Gly Lys Leu Thr Asp Leu Pro Phe Phe Asp Leu Met Ser Ile Pro
            180                 185                 190

Gly Lys Leu Arg Ala Gly Phe Gly Ala Ile Gly Leu Arg Pro Ser Pro
        195                 200                 205

Pro Gly Tyr Glu Glu Ser Val Glu Gln Phe Val Arg Arg Asn Leu Gly
    210                 215                 220

Ala Glu Val Phe Glu Arg Leu Ile Glu Ser Phe Cys Ser Gly Val Tyr
225                 230                 235                 240

Ala Gly Asp Pro Ser Lys Leu Ser Met Lys Ala Ala Phe Gly Lys Val
                245                 250                 255

Trp Lys Leu Glu Gln Thr Gly Gly Ser Ile Ile Gly Gly Thr Phe Lys
            260                 265                 270

Ala Ile Lys Glu Arg Ser Ser Asn Pro Lys Pro Pro Arg Asp Pro Arg
        275                 280                 285

Leu Pro Thr Pro Lys Gly Gln Thr Val Gly Ser Phe Arg Lys Gly Leu
    290                 295                 300

Arg Met Leu Pro Asp Ala Ile Cys Glu Arg Leu Gly Ser Lys Val Lys
305                 310                 315                 320

Leu Ser Trp Lys Leu Ser Ser Ile Thr Lys Ser Asp Lys Gly Gly Tyr
                325                 330                 335

Leu Leu Thr Tyr Glu Thr Pro Glu Gly Val Val Ser Leu Arg Ser Arg
            340                 345                 350

Ser Ile Val Met Thr Val Pro Ser Tyr Val Ala Ser Asn Ile Leu Arg
        355                 360                 365

Pro Leu Ser Val Ala Ala Ala Asp Ala Leu Ser Ser Phe Tyr Tyr Pro
    370                 375                 380

Pro Val Ala Ala Val Thr Ile Ser Tyr Pro Gln Glu Ala Ile Arg Asp
385                 390                 395                 400

Glu Arg Leu Val Asp Gly Glu Leu Lys Gly Phe Gly Gln Leu His Pro
                405                 410                 415

Arg Ser Gln Gly Val Glu Thr Leu Gly Thr Ile Tyr Ser Ser Ser Leu
            420                 425                 430

Phe Pro Asn Arg Ala Pro Asn Gly Arg Val Leu Leu Ser Asn Ile Ile
        435                 440                 445

Gly Gly Ala Thr Asn Thr Glu Ile Val Ser Lys Thr Glu Ser Gln Leu
    450                 455                 460

Val Glu Ala Val Asp Arg Asp Leu Arg Lys Met Leu Ile Lys Pro Lys
465                 470                 475                 480

Ala Gln Asp Pro Phe Val Thr Gly Val Arg Val Trp Pro Gln Ala Ile
                485                 490                 495

Pro Gln Phe Leu Val Gly His Leu Asp Thr Leu Gly Thr Ala Lys Ala
            500                 505                 510

Ala Leu Ser Asp Asn Gly Leu Asp Gly Leu Phe Leu Gly Gly Asn Tyr
        515                 520                 525
```

```
Val Ser Gly Val Ala Leu Gly Arg Cys Val Glu Gly Ala Tyr Glu Ile
    530                 535                 540

Ala Ser Glu Val Thr Gly Phe Leu Ser Gln Tyr Ala Tyr Lys
545                 550                 555


<210> SEQ ID NO 42
<211> LENGTH: 557
<212> TYPE: PRT
<213> ORGANISM: Artificial sequence
<220> FEATURE:
<223> OTHER INFORMATION: Amino-acid sequence of PPO1 form potato mutant
      (StPPO1 L444S/Y446I)

<400> SEQUENCE: 42

Met Thr Thr Thr Ala Val Ala Asn His Pro Ser Ile Phe Thr His Arg
1               5                   10                  15

Ser Pro Leu Leu Ser Pro Ser Ser Ser Ser Ser Ser Pro Ser Phe Leu
            20                  25                  30

Phe Leu Asn Arg Thr Asn Phe Ile Pro Tyr Phe Ser Thr Ser Lys Arg
        35                  40                  45

Asn Ser Val Asn Cys Asn Gly Trp Arg Thr Arg Cys Ser Val Ala Lys
    50                  55                  60

Asp Tyr Thr Val Pro Pro Ser Glu Val Asp Gly Asn Gln Phe Pro Glu
65                  70                  75                  80

Leu Asp Cys Val Val Val Gly Ala Gly Ile Ser Gly Leu Cys Ile Thr
                85                  90                  95

Lys Val Ile Ser Asp Asn Tyr Pro Asn Leu Met Val Thr Glu Ala Arg
            100                 105                 110

Asp Arg Ala Gly Gly Asn Ile Thr Thr Val Glu Arg Asp Gly Tyr Leu
        115                 120                 125

Trp Glu Glu Gly Pro Asn Ser Phe Gln Pro Ser Asp Pro Met Leu Thr
    130                 135                 140

Met Ala Val Asp Cys Gly Leu Lys Asp Asp Leu Val Leu Gly Asp Pro
145                 150                 155                 160

Asp Ala Pro Arg Phe Val Leu Trp Lys Asp Lys Leu Arg Pro Val Pro
                165                 170                 175

Gly Lys Leu Thr Asp Leu Pro Phe Phe Asp Leu Met Ser Ile Pro Gly
            180                 185                 190

Lys Leu Arg Ala Gly Phe Gly Ala Ile Gly Leu Arg Pro Ser Pro Pro
        195                 200                 205

Gly Tyr Glu Glu Ser Val Glu Gln Phe Val Arg Arg Asn Leu Gly Ala
    210                 215                 220

Glu Val Phe Glu Arg Leu Ile Glu Pro Phe Cys Ser Gly Val Tyr Ala
225                 230                 235                 240

Gly Asp Pro Ser Lys Leu Ser Met Lys Ala Ala Phe Gly Lys Val Trp
                245                 250                 255

Lys Leu Glu Gln Thr Gly Gly Ser Ile Ile Gly Gly Thr Phe Lys Ala
            260                 265                 270

Ile Lys Glu Arg Ser Ser Asn Pro Lys Pro Pro Arg Asp Pro Arg Leu
        275                 280                 285

Pro Thr Pro Lys Gly Gln Thr Val Gly Ser Phe Arg Lys Gly Leu Arg
    290                 295                 300

Met Leu Pro Asp Ala Ile Cys Glu Arg Leu Gly Ser Lys Val Lys Leu
305                 310                 315                 320

Ser Trp Lys Leu Ser Ser Ile Thr Lys Ser Glu Lys Gly Gly Tyr Leu
```

325 330 335

Leu Thr Tyr Glu Thr Pro Glu Gly Val Val Ser Leu Arg Ser Arg Ser
340 345 350

Ile Val Met Thr Val Pro Ser Tyr Val Ala Ser Asn Ile Leu Arg Pro
355 360 365

Leu Ser Val Ala Ala Ala Asp Ala Leu Ser Ser Phe Tyr Tyr Pro Pro
370 375 380

Val Ala Ala Val Thr Ile Ser Tyr Pro Gln Glu Ala Ile Arg Asp Glu
385 390 395 400

Arg Leu Val Asp Gly Glu Leu Lys Gly Phe Gly Gln Leu His Pro Arg
405 410 415

Ser Gln Gly Val Glu Thr Leu Gly Thr Ile Tyr Ser Ser Ser Leu Phe
420 425 430

Pro Asn Arg Ala Pro Asn Gly Arg Val Leu Leu Ser Asn Ile Ile Gly
435 440 445

Gly Ala Thr Asn Thr Glu Ile Val Ser Lys Thr Glu Ser Gln Leu Val
450 455 460

Glu Ala Val Asp Arg Asp Leu Arg Lys Met Leu Ile Lys Pro Lys Ala
465 470 475 480

Gln Asp Pro Phe Val Thr Gly Val Arg Val Trp Pro Gln Ala Ile Pro
485 490 495

Gln Phe Leu Val Gly His Leu Asp Thr Leu Gly Thr Ala Lys Thr Ala
500 505 510

Leu Ser Asp Asn Gly His Asp Gly Leu Phe Leu Gly Gly Asn Tyr Val
515 520 525

Ser Gly Val Ala Leu Gly Arg Cys Val Glu Gly Ala Tyr Glu Ile Ala
530 535 540

Ser Glu Val Thr Gly Phe Leu Ser Gln Tyr Ala Tyr Lys
545 550 555

<210> SEQ ID NO 43
<211> LENGTH: 553
<212> TYPE: PRT
<213> ORGANISM: Artificial sequence
<220> FEATURE:
<223> OTHER INFORMATION: Amino-acid sequence of PPO1 from tobacco mutant (NtPPO1 L440S/Y442I)

<400> SEQUENCE: 43

Met Thr Thr Thr Pro Ile Ala Asn His Pro Asn Val Phe Thr His Arg
1 5 10 15

Ser Pro Pro Ser Ser Ser Ser Ser Ser Pro Ser Ala Phe Leu Thr Arg
20 25 30

Thr Ser Phe Leu Pro Phe Ser Ser Ile Cys Lys Arg Asn Ser Val Asn
35 40 45

Cys Thr Gly Trp Arg Thr Arg Cys Ser Val Ala Lys Asp Tyr Thr Val
50 55 60

Pro Ser Ser Ala Val Asp Gly Gly Pro Ala Ala Glu Leu Asp Cys Val
65 70 75 80

Ile Val Gly Ala Gly Ile Ser Gly Leu Cys Ile Ala Gln Val Met Ser
85 90 95

Ala Asn Tyr Pro Asn Leu Met Val Thr Glu Ala Arg Asp Arg Ala Gly
100 105 110

Gly Asn Ile Thr Thr Val Glu Arg Asp Gly Tyr Leu Trp Glu Glu Gly
115 120 125

-continued

```
Pro Asn Ser Phe Gln Pro Ser Asp Pro Met Leu Thr Met Ala Val Asp
    130                 135                 140

Cys Gly Leu Lys Asp Asp Leu Val Leu Gly Asp Pro Asn Ala Pro Arg
145                 150                 155                 160

Phe Val Leu Trp Lys Gly Lys Leu Arg Pro Val Pro Ser Lys Leu Thr
                165                 170                 175

Asp Leu Pro Phe Phe Asp Leu Met Ser Ile Pro Gly Lys Leu Arg Ala
            180                 185                 190

Gly Phe Gly Ala Ile Gly Leu Arg Pro Ser Pro Pro Gly His Glu Glu
        195                 200                 205

Ser Val Glu Gln Phe Val Arg Arg Asn Leu Gly Gly Glu Val Phe Glu
    210                 215                 220

Arg Leu Ile Glu Pro Phe Cys Ser Gly Val Tyr Ala Gly Asp Pro Ser
225                 230                 235                 240

Lys Leu Ser Met Lys Ala Ala Phe Gly Lys Val Trp Lys Leu Glu Glu
                245                 250                 255

Thr Gly Gly Ser Ile Ile Gly Gly Thr Phe Lys Ala Ile Lys Glu Arg
            260                 265                 270

Ser Ser Thr Pro Lys Ala Pro Arg Asp Pro Arg Leu Pro Lys Pro Lys
        275                 280                 285

Gly Gln Thr Val Gly Ser Phe Arg Lys Gly Leu Arg Met Leu Pro Asp
    290                 295                 300

Ala Ile Ser Ala Arg Leu Gly Ser Lys Leu Lys Leu Ser Trp Lys Leu
305                 310                 315                 320

Ser Ser Ile Thr Lys Ser Glu Lys Gly Gly Tyr Arg Leu Thr Tyr Glu
                325                 330                 335

Thr Pro Glu Gly Val Val Ser Leu Gln Ser Arg Ser Ile Val Met Thr
            340                 345                 350

Val Pro Ser Tyr Val Ala Ser Asn Ile Leu Arg Pro Leu Ser Val Ala
        355                 360                 365

Ala Ala Asp Ala Leu Ser Asn Phe Tyr Tyr Pro Pro Val Gly Ala Val
    370                 375                 380

Thr Ile Ser Tyr Pro Gln Glu Ala Ile Arg Asp Glu Arg Leu Val Asp
385                 390                 395                 400

Gly Glu Leu Lys Gly Phe Gly Gln Leu His Pro Arg Thr Gln Gly Val
                405                 410                 415

Glu Thr Leu Gly Thr Ile Tyr Ser Ser Ser Leu Phe Pro Asn Arg Ala
            420                 425                 430

Pro Lys Gly Arg Val Leu Leu Ser Asn Ile Ile Gly Gly Ala Lys Asn
        435                 440                 445

Pro Glu Ile Leu Ser Lys Thr Glu Ser Gln Leu Val Glu Val Val Asp
    450                 455                 460

Arg Asp Leu Arg Lys Met Leu Ile Lys Pro Lys Ala Gln Asp Pro Leu
465                 470                 475                 480

Val Val Gly Val Arg Val Trp Pro Gln Ala Ile Pro Gln Phe Leu Val
                485                 490                 495

Gly His Leu Asp Thr Leu Ser Thr Ala Lys Ala Ala Met Ser Asp Asn
            500                 505                 510

Gly Leu Glu Gly Leu Phe Leu Gly Gly Asn Tyr Val Ser Gly Val Ala
        515                 520                 525

Leu Gly Arg Cys Val Glu Gly Ala Tyr Glu Val Ala Ser Glu Val Thr
    530                 535                 540

Gly Phe Leu Pro Arg Tyr Ala Tyr Lys
```

545 550

<210> SEQ ID NO 44
<211> LENGTH: 536
<212> TYPE: PRT
<213> ORGANISM: Artificial sequence
<220> FEATURE:
<223> OTHER INFORMATION: Amino-acid sequence of PPO1 form Arabidopsis thaliana mutant (AtPPO1 L424S/Y426I)

<400> SEQUENCE: 44

Met Glu Leu Ser Leu Leu Arg Pro Thr Thr Gln Ser Leu Leu Pro Ser
1 5 10 15

Phe Ser Lys Pro Asn Leu Arg Leu Asn Val Tyr Lys Pro Leu Arg Leu
20 25 30

Arg Cys Ser Val Ala Gly Gly Pro Thr Val Gly Ser Ser Lys Ile Glu
35 40 45

Gly Gly Gly Gly Thr Thr Ile Thr Thr Asp Cys Val Ile Val Gly Gly
50 55 60

Gly Ile Ser Gly Leu Cys Ile Ala Gln Ala Leu Ala Thr Lys His Pro
65 70 75 80

Asp Ala Ala Pro Asn Leu Ile Val Thr Glu Ala Lys Asp Arg Val Gly
85 90 95

Gly Asn Ile Ile Thr Arg Glu Glu Asn Gly Phe Leu Trp Glu Glu Gly
100 105 110

Pro Asn Ser Phe Gln Pro Ser Asp Pro Met Leu Thr Met Val Val Asp
115 120 125

Ser Gly Leu Lys Asp Asp Leu Val Leu Gly Asp Pro Thr Ala Pro Arg
130 135 140

Phe Val Leu Trp Asn Gly Lys Leu Arg Pro Val Pro Ser Lys Leu Thr
145 150 155 160

Asp Leu Pro Phe Phe Asp Leu Met Ser Ile Gly Gly Lys Ile Arg Ala
165 170 175

Gly Phe Gly Ala Leu Gly Ile Arg Pro Ser Pro Pro Gly Arg Glu Glu
180 185 190

Ser Val Glu Glu Phe Val Arg Arg Asn Leu Gly Asp Glu Val Phe Glu
195 200 205

Arg Leu Ile Glu Pro Phe Cys Ser Gly Val Tyr Ala Gly Asp Pro Ser
210 215 220

Lys Leu Ser Met Lys Ala Ala Phe Gly Lys Val Trp Lys Leu Glu Gln
225 230 235 240

Asn Gly Gly Ser Ile Ile Gly Gly Thr Phe Lys Ala Ile Gln Glu Arg
245 250 255

Lys Asn Ala Pro Lys Ala Glu Arg Asp Pro Arg Leu Pro Lys Pro Gln
260 265 270

Gly Gln Thr Val Gly Ser Phe Arg Lys Gly Leu Arg Met Leu Pro Glu
275 280 285

Ala Ile Ser Ala Arg Leu Gly Ser Lys Val Lys Leu Ser Trp Lys Leu
290 295 300

Ser Gly Ile Thr Leu Glu Ser Gly Gly Tyr Asn Leu Thr Tyr Glu Thr
305 310 315 320

Pro Asp Gly Leu Val Ser Val Gln Ser Lys Ser Val Val Met Thr Val
325 330 335

Pro Ser His Val Ala Ser Gly Leu Leu Arg Pro Leu Ser Glu Ser Ala
340 345 350

```
Ala Asn Ala Leu Ser Lys Leu Tyr Tyr Pro Pro Val Ala Ala Val Ser
        355                 360                 365

Ile Ser Tyr Pro Lys Glu Ala Ile Arg Thr Glu Cys Leu Ile Asp Gly
    370                 375                 380

Glu Leu Lys Gly Phe Gly Gln Leu His Pro Arg Thr Gln Gly Val Glu
385                 390                 395                 400

Thr Leu Gly Thr Ile Tyr Ser Ser Ser Leu Phe Pro Asn Arg Ala Pro
                405                 410                 415

Pro Gly Arg Ile Leu Leu Ser Asn Ile Ile Gly Gly Ser Thr Asn Thr
            420                 425                 430

Gly Ile Leu Ser Lys Ser Glu Gly Glu Leu Val Glu Ala Val Asp Arg
        435                 440                 445

Asp Leu Arg Lys Met Leu Ile Lys Pro Asn Ser Thr Asp Pro Leu Lys
    450                 455                 460

Leu Gly Val Arg Val Trp Pro Gln Ala Ile Pro Gln Phe Leu Val Gly
465                 470                 475                 480

His Phe Asp Ile Leu Asp Thr Ala Lys Ser Ser Leu Thr Ser Ser Gly
                485                 490                 495

Tyr Glu Gly Leu Phe Leu Gly Gly Asn Tyr Val Ala Gly Val Ala Leu
            500                 505                 510

Gly Arg Cys Val Glu Gly Ala Tyr Glu Thr Ala Ile Glu Val Asn Asn
        515                 520                 525

Phe Met Ser Arg Tyr Ala Tyr Lys
    530                 535


<210> SEQ ID NO 45
<211> LENGTH: 539
<212> TYPE: PRT
<213> ORGANISM: Artificial sequence
<220> FEATURE:
<223> OTHER INFORMATION: Amino-acid sequence of PPO1 from upland cotton
      mutant (GhPPO1 L426S/Y428I)

<400> SEQUENCE: 45

Met Thr Ala Leu Ile Asp Leu Ser Leu Leu Arg Ser Ser Pro Ser Val
1               5                   10                  15

Ser Pro Phe Ser Ile Pro His His Gln His Pro Pro Arg Phe Arg Lys
            20                  25                  30

Pro Phe Lys Leu Arg Cys Ser Leu Ala Glu Gly Pro Thr Ile Ser Ser
        35                  40                  45

Ser Lys Ile Asp Gly Gly Glu Ser Ser Ile Ala Asp Cys Val Ile Val
    50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
            100                 105                 110

Glu Gly Pro Asn Ser Phe Gln Pro Ser Asp Pro Ile Leu Thr Met Ala
        115                 120                 125

Val Asp Ser Gly Leu Lys Asp Asp Leu Val Leu Gly Asp Pro Asn Ala
    130                 135                 140

Pro Arg Phe Val Leu Trp Glu Gly Lys Leu Arg Pro Val Pro Ser Lys
145                 150                 155                 160

Pro Thr Asp Leu Pro Phe Phe Asp Leu Met Ser Ile Ala Gly Lys Leu
                165                 170                 175
```

```
Arg Ala Gly Phe Gly Ala Ile Gly Ile Arg Pro Pro Pro Pro Gly Tyr
            180                 185                 190

Glu Glu Ser Val Glu Glu Phe Val Arg Arg Asn Leu Gly Ala Glu Val
        195                 200                 205

Phe Glu Arg Phe Ile Glu Pro Phe Cys Ser Gly Val Tyr Ala Gly Asp
    210                 215                 220

Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
                245                 250                 255

Glu Arg Asn Lys Thr Pro Lys Pro Pro Arg Asp Pro Arg Leu Pro Lys
            260                 265                 270

Pro Lys Gly Gln Thr Val Gly Ser Phe Arg Lys Gly Leu Thr Met Leu
        275                 280                 285

Pro Glu Ala Ile Ala Asn Ser Leu Gly Ser Asn Val Lys Leu Ser Trp
    290                 295                 300

Lys Leu Ser Ser Ile Thr Lys Leu Gly Asn Gly Gly Tyr Asn Leu Thr
305                 310                 315                 320

Phe Glu Thr Pro Glu Gly Met Val Ser Leu Gln Ser Arg Ser Val Val
                325                 330                 335

Met Thr Ile Pro Ser His Val Ala Ser Asn Leu Leu His Pro Leu Ser
            340                 345                 350

Ala Ala Ala Ala Asp Ala Leu Ser Gln Phe Tyr Tyr Pro Pro Val Ala
        355                 360                 365

Ser Val Thr Val Ser Tyr Pro Lys Glu Ala Ile Arg Lys Glu Cys Leu
    370                 375                 380

Ile Asp Gly Glu Leu Lys Gly Phe Gly Gln Leu His Pro Arg Ser Gln
385                 390                 395                 400

Gly Ile Glu Thr Leu Gly Thr Ile Tyr Ser Ser Ser Leu Phe Pro Asn
                405                 410                 415

Arg Ala Pro Ser Gly Arg Val Leu Leu Ser Asn Ile Ile Gly Gly Ala
            420                 425                 430

Thr Asn Thr Gly Ile Leu Ser Lys Thr Glu Gly Glu Leu Val Glu Ala
        435                 440                 445

Val Asp Arg Asp Leu Arg Lys Met Leu Ile Asn Pro Asn Ala Lys Asp
    450                 455                 460

Pro Leu Val Leu Gly Val Arg Val Trp Pro Lys Ala Ile Pro Gln Phe
465                 470                 475                 480

Leu Val Gly His Leu Asp Leu Leu Asp Ser Ala Lys Met Ala Leu Arg
                485                 490                 495

Asp Ser Gly Phe His Gly Leu Phe Leu Gly Gly Asn Tyr Val Ser Gly
            500                 505                 510

Val Ala Leu Gly Arg Cys Val Glu Gly Ala Tyr Glu Val Ala Ala Glu
        515                 520                 525

Val Lys Glu Phe Leu Ser Gln Tyr Ala Tyr Lys
    530                 535
```

<210> SEQ ID NO 46
<211> LENGTH: 538
<212> TYPE: PRT
<213> ORGANISM: Artificial sequence
<220> FEATURE:
<223> OTHER INFORMATION: Amino-acid sequence of PPO1 from radish mutant (RsPPO1 L425S/Y427I)

<400> SEQUENCE: 46

```
Met Asp Leu Ser Leu Leu Arg Pro Gln Pro Phe Leu Ser Pro Phe Ser
1               5                   10                  15

Asn Pro Phe Pro Arg Ser Arg Pro Tyr Tyr Lys Pro Leu Asn Leu His
            20                  25                  30

Cys Ser Val Ser Gly Gly Ser Val Val Gly Ser Ser Thr Ile Glu Gly
        35                  40                  45

Gly Gly Gly Gly Gly Lys Thr Val Ala Ala Asp Cys Val Ile Val Gly
    50                  55                  60

Gly Gly Ile Ser Gly Leu Cys Ile Ala Gln Ala Leu Val Thr Lys His
65                  70                  75                  80

Pro Asp Ala Ala Lys Asn Val Ile Val Thr Glu Ala Lys Asp Arg Val
                85                  90                  95

Gly Gly Asn Ile Ile Thr Arg Glu Glu Gln Gly Phe Leu Trp Glu Glu
            100                 105                 110

Gly Pro Asn Ser Phe Gln Pro Ser Asp Pro Met Leu Thr Met Val Val
        115                 120                 125

Asp Ser Gly Leu Lys Asp Asp Leu Val Leu Gly Asp Pro Thr Ala Pro
    130                 135                 140

Arg Phe Val Leu Trp Asn Gly Lys Leu Arg Pro Val Pro Ser Lys Leu
145                 150                 155                 160

Thr Asp Leu Pro Phe Phe Asp Leu Met Ser Ile Arg Gly Lys Ile Arg
                165                 170                 175

Ala Gly Phe Gly Ala Ile Gly Ile Arg Pro Ser Pro Pro Gly Arg Glu
            180                 185                 190

Glu Ser Val Glu Glu Phe Val Arg Arg Asn Leu Gly Asp Glu Val Phe
        195                 200                 205

Glu Arg Leu Ile Glu Pro Phe Cys Ser Gly Val Tyr Ala Gly Asp Pro
    210                 215                 220

Ala Lys Leu Ser Met Lys Ala Ala Phe Gly Lys Val Trp Lys Leu Glu
225                 230                 235                 240

Glu Asn Gly Gly Ser Ile Ile Gly Gly Ala Phe Lys Ala Ile Gln Ala
                245                 250                 255

Arg Asn Lys Ala Pro Lys Thr Thr Arg Asp Pro Arg Leu Pro Lys Pro
            260                 265                 270

Lys Gly Gln Thr Val Gly Ser Phe Arg Lys Gly Leu Thr Met Leu Pro
        275                 280                 285

Glu Ala Ile Ser Ala Arg Leu Gly Asn Lys Val Lys Val Ser Trp Lys
    290                 295                 300

Leu Ser Ser Ile Thr Lys Leu Ala Asn Gly Glu Tyr Ser Leu Thr Tyr
305                 310                 315                 320

Glu Thr Pro Glu Gly Ile Val Thr Val Gln Ser Lys Ser Val Val Met
                325                 330                 335

Thr Val Pro Ser His Val Ala Ser Ser Leu Leu Arg Pro Leu Ser Asp
            340                 345                 350

Ser Ala Ala Glu Ala Leu Ser Lys Leu Tyr Tyr Pro Pro Val Ala Ala
        355                 360                 365

Val Ser Ile Ser Tyr Pro Lys Glu Ala Ile Arg Ser Glu Cys Leu Ile
    370                 375                 380

Asp Gly Glu Leu Lys Gly Phe Gly Gln Leu His Pro Arg Thr Gln Lys
385                 390                 395                 400

Val Glu Thr Leu Gly Thr Ile Tyr Ser Ser Ser Leu Phe Pro Asn Arg
                405                 410                 415
```

Ala Pro Pro Gly Arg Val Leu Leu Ser Asn Ile Ile Gly Gly Thr Thr
420 425 430

Asn Thr Gly Ile Leu Ser Lys Ser Glu Gly Glu Leu Val Glu Ala Val
435 440 445

Asp Arg Asp Leu Arg Lys Met Leu Ile Lys Pro Ser Ser Thr Asp Pro
450 455 460

Leu Val Leu Gly Val Arg Val Trp Pro Gln Ala Ile Pro Gln Phe Leu
465 470 475 480

Ile Gly His Ile Asp Leu Val Asp Ala Ala Lys Ala Ser Leu Ser Ser
485 490 495

Ser Gly His Glu Gly Ile Phe Leu Gly Gly Asn Tyr Val Ala Gly Val
500 505 510

Ala Leu Gly Arg Cys Val Glu Cys Ala Tyr Glu Thr Ala Thr Gln Val
515 520 525

Asn Asp Phe Met Ser Arg Tyr Thr Tyr Lys
530 535

<210> SEQ ID NO 47
<211> LENGTH: 535
<212> TYPE: PRT
<213> ORGANISM: Artificial sequence
<220> FEATURE:
<223> OTHER INFORMATION: Amino-acid sequence of PPO1 from foxtail millet mutant (SiPPO1 L422S/Y424I)

<400> SEQUENCE: 47

Met Val Ala Ala Ala Met Ala Thr Ala Pro Ser Ala Gly Val Pro Pro
1 5 10 15

Leu Arg Gly Thr Arg Gly Pro Ala Arg Phe Arg Ile Arg Gly Val Ser
20 25 30

Val Arg Cys Ala Ala Val Ala Gly Gly Ala Ala Glu Ala Pro Ala Ser
35 40 45

Ala Gly Ala Arg Val Ser Ala Asp Cys Val Val Val Gly Gly Gly Ile
50 55 60

Ser Gly Leu Cys Thr Ala Gln Ala Leu Ala Thr Lys His Gly Val Gly
65 70 75 80

Asp Val Leu Val Thr Glu Ala Arg Ala Arg Pro Gly Gly Asn Ile Thr
85 90 95

Thr Val Glu Arg Pro Asp Glu Gly Tyr Leu Trp Glu Glu Gly Pro Asn
100 105 110

Ser Phe Gln Pro Ser Asp Pro Val Leu Thr Met Ala Val Asp Ser Gly
115 120 125

Leu Lys Asp Asp Leu Val Phe Gly Asp Pro Asn Ala Pro Arg Phe Val
130 135 140

Leu Trp Glu Gly Lys Leu Arg Pro Val Pro Ser Lys Pro Ala Asp Leu
145 150 155 160

Pro Phe Phe Asp Leu Met Ser Ile Pro Gly Lys Leu Arg Ala Gly Phe
165 170 175

Gly Ala Leu Gly Ile Arg Pro Pro Pro Pro Gly Arg Glu Glu Ser Val
180 185 190

Glu Glu Phe Val Arg Arg Asn Leu Gly Ala Glu Val Phe Glu Arg Leu
195 200 205

Ile Glu Pro Phe Cys Ser Gly Val Tyr Ala Gly Asp Pro Ser Lys Leu
210 215 220

Ser Met Lys Ala Ala Phe Gly Lys Val Trp Arg Leu Glu Glu Ala Gly

-continued 225 230 235 240

Gly Ser Ile Ile Gly Gly Thr Ile Lys Thr Ile Gln Glu Arg Gly Lys
245 250 255

Asn Pro Lys Pro Pro Arg Asp Pro Arg Leu Pro Thr Pro Lys Gly Gln
260 265 270

Thr Val Ala Ser Phe Arg Lys Gly Leu Ala Met Leu Pro Asn Ala Ile
275 280 285

Thr Ser Ser Leu Gly Ser Lys Val Lys Leu Ser Trp Lys Leu Thr Ser
290 295 300

Ile Thr Lys Ser Asp Gly Met Gly Tyr Val Leu Val Tyr Glu Thr Pro
305 310 315 320

Glu Gly Val Val Ser Val Gln Ala Lys Ser Val Ile Met Thr Ile Pro
325 330 335

Ser Tyr Val Ala Ser Asp Ile Leu Arg Pro Leu Ser Ser Asp Ala Ala
340 345 350

Asp Ala Leu Ser Arg Phe Tyr Tyr Pro Pro Val Ala Ala Val Thr Ile
355 360 365

Ser Tyr Pro Lys Glu Ala Ile Arg Lys Glu Cys Leu Ile Asp Gly Glu
370 375 380

Leu Gln Gly Phe Gly Gln Leu His Pro Arg Ser Gln Gly Val Glu Thr
385 390 395 400

Leu Gly Thr Ile Tyr Ser Ser Ser Leu Phe Pro Asn Arg Ala Pro Ala
405 410 415

Gly Arg Val Leu Leu Ser Asn Ile Ile Gly Gly Ala Thr Asn Thr Gly
420 425 430

Ile Val Ser Lys Ser Ala Ser Glu Leu Val Glu Ala Val Asp Arg Asp
435 440 445

Leu Arg Lys Met Leu Ile Asn Pro Ser Ala Val Asp Pro Leu Val Leu
450 455 460

Gly Val Arg Val Trp Pro Gln Ala Ile Pro Gln Phe Leu Val Gly His
465 470 475 480

Leu Asp Leu Leu Glu Ala Ala Lys Ser Ser Leu Asp Arg Gly Gly Tyr
485 490 495

Asp Gly Leu Phe Leu Gly Gly Asn Tyr Val Ala Gly Val Ala Leu Gly
500 505 510

Arg Cys Val Glu Gly Ala Tyr Glu Ser Ala Ser Gln Ile Ser Asp Phe
515 520 525

Leu Thr Lys Tyr Ala Tyr Lys
530 535

<210> SEQ ID NO 48
<211> LENGTH: 537
<212> TYPE: PRT
<213> ORGANISM: Artificial sequence
<220> FEATURE:
<223> OTHER INFORMATION: Amino-acid sequence of PPO1 from cabbage mutant
(BoPPO1 L424S/Y426I)

<400> SEQUENCE: 48

Met Asp Leu Ser Leu Leu Arg Pro Gln Pro Phe Leu Ser Pro Phe Ser
1 5 10 15

Asn Pro Phe Pro Arg Ser Arg Pro Tyr Lys Pro Pro Asn Leu Arg Cys
20 25 30

Ser Val Ser Gly Gly Ser Val Val Gly Gly Ser Ser Thr Ile Glu Gly
35 40 45

-continued

```
Gly Gly Gly Gly Lys Thr Val Ala Ala Asp Cys Val Ile Val Gly Gly
    50                  55                  60

Gly Ile Ser Gly Leu Cys Ile Ala Gln Ala Leu Val Thr Lys His Pro
65                  70                  75                  80

Asp Ala Ala Lys Ser Val Met Val Thr Glu Ala Lys Asp Arg Val Gly
                85                  90                  95

Gly Asn Ile Ile Thr Arg Glu Glu Gln Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Ile Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ala
    210                 215                 220

Lys Leu Ser Met Lys Ala Ala Phe Gly Lys Val Trp Lys Leu Glu Glu
225                 230                 235                 240

Asn Gly Gly Ser Ile Ile Gly Gly Ala Phe Lys Ala Ile Gln Ala Arg
                245                 250                 255

Asn Lys Ala Pro Lys Thr Thr Arg Asp Pro Arg Leu Pro Lys Pro Lys
            260                 265                 270

Gly Gln Thr Val Gly Ser Phe Arg Lys Gly Leu Thr Met Leu Pro Glu
        275                 280                 285

Ala Ile Ser Ala Arg Leu Gly Asp Lys Val Lys Val Ser Trp Lys Leu
    290                 295                 300

Ser Ser Ile Ser Lys Leu Pro Ser Gly Gly Tyr Ser Leu Thr Tyr Glu
305                 310                 315                 320

Thr Pro Glu Gly Ile Val Thr Val Gln Ser Lys Ser Val Val Met Thr
                325                 330                 335

Val Pro Ser His Val Ala Ser Ser Leu Leu Arg Pro Leu Ser Asp Ser
            340                 345                 350

Ala Ala Glu Ala Leu Ser Lys Leu Tyr Tyr Pro Pro Val Ala Ala Val
        355                 360                 365

Ser Ile Ser Tyr Leu Lys Glu Ala Ile Arg Ser Glu Cys Leu Ile Asp
    370                 375                 380

Gly Glu Leu Lys Gly Phe Gly Gln Leu His Pro Arg Thr Gln Lys Val
385                 390                 395                 400

Glu Thr Leu Gly Thr Ile Tyr Ser Ser Ser Leu Phe Pro Asn Arg Ala
                405                 410                 415

Pro Pro Gly Arg Val Leu Leu Ser Asn Ile Ile Gly Gly Ala Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Met Pro Ser Ser Thr Asp Pro Leu
    450                 455                 460

Val Leu Gly Val Lys Val Trp Pro Gln Ala Ile Pro Gln Phe Leu Ile
```

-continued

```
465                 470                 475                 480

Gly His Ile Asp Leu Val Asp Ala Ala Lys Ala Ser Leu Ser Ser Ser
                485                 490                 495

Gly His Glu Gly Leu Phe Leu Gly Gly Asn Tyr Val Ala Gly Val Ala
            500                 505                 510

Leu Gly Arg Cys Val Glu Gly Ala Tyr Glu Thr Ala Thr Gln Val Asn
        515                 520                 525

Asp Phe Met Ser Arg Tyr Ala Tyr Lys
    530                 535


<210> SEQ ID NO 49
<211> LENGTH: 1258
<212> TYPE: DNA
<213> ORGANISM: Artificial sequence
<220> FEATURE:
<223> OTHER INFORMATION: Amino-acid sequence of PPO1 from homologous
      replacement repair template of rice mutant (OsPPO1 L423S/Y425I)

<400> SEQUENCE: 49

acatgaacta gtaatgattg gggtgcttaa ccatttgttc tgcatttcct ccattttcag     60

gttgggtagc aaagtcaaac tttcatggaa gttgacaagc attacaaagt cagacaacaa    120

aggatatgca ttagtgtatg aaacaccaga aggggtggtc tcggtgcaag ctaaaactgt    180

tgtcatgacc atcccatcat atgttgctag tgatatcttg cggccacttt cagtaagtta    240

tatatattta attaactttc tgttcccaaa atacactgca gcacttcatt gcttcctgag    300

gtcctcgatt catttttcgg tagacaggaa gtagtattca tttgcacttt ttaagggatt    360

aattcaacat atccactgga aatatacata tcctacacat cctgtcaaca tacttgctaa    420

acagcatttt gtttgagttg actggcatct cagcagccaa ttactatctt taggggacaa    480

gccacattct taataaatcc tgtcggaaat cactttttga tttttataga ttagtgttgt    540

catagaattt ggcttggtga tctacttggt aaggttaact gattcacaag tcggacaatt    600

tcttcaccaa tctagcagta tgtttaagtg tgttggtact taattctaaa tgtcctgcgc    660

atggtaacat atcatatgca aaaattcctc agtaaccgaa atttatactg taagttttaa    720

ctgtctttac actgttaatt ttagacatac ttcttccttg cttgttcatt gaacttgttt    780

ccccccttcca cagagtgatg cagcagatgc tctgtcaata ttctattatc caccagttgc    840

tgctgtaact gtttcatatc caaaagaagc aattagaaaa gaatgcttaa ttgacggaga    900

gctccagggt ttcggccagc tgcatccgcg tagtcaggga gttgagactt taggtactta    960

taggaattca accttattat tcttctaaca tataaatgaa ctaatctttc ttgtctagtt   1020

tgcatttatt gtggattaag tttggttata ttgttcttac aagtttgtgg tattattttg   1080

tataggaaca atatatagct catcactctt tccaaatcgt gctccagctg gaagggtgtt   1140

actttccaac atcataggag gttctacaaa tacagggatt gtttccaagg tatcgctgtc   1200

aagttgttta ttttgcgact atatgattac agtatcctgt ttttcaactc cagctgct      1258


<210> SEQ ID NO 50
<211> LENGTH: 6
<212> TYPE: PRT
<213> ORGANISM: Artificial sequence
<220> FEATURE:
<223> OTHER INFORMATION: Motif

<400> SEQUENCE: 50

Leu Leu Leu Asn Tyr Ile
1               5
```

<210> SEQ ID NO 51
<211> LENGTH: 6
<212> TYPE: PRT
<213> ORGANISM: Artificial sequence
<220> FEATURE:
<223> OTHER INFORMATION: Mutant

<400> SEQUENCE: 51

Leu Leu Ser Asn Tyr Ile
1               5

<210> SEQ ID NO 52
<211> LENGTH: 6
<212> TYPE: PRT
<213> ORGANISM: Artificial sequence
<220> FEATURE:
<223> OTHER INFORMATION: Mutant

<400> SEQUENCE: 52

Leu Leu Ile Asn Tyr Ile
1               5

<210> SEQ ID NO 53
<211> LENGTH: 6
<212> TYPE: PRT
<213> ORGANISM: Artificial sequence
<220> FEATURE:
<223> OTHER INFORMATION: Mutant

<400> SEQUENCE: 53

Leu Leu Gly Asn Tyr Ile
1               5

<210> SEQ ID NO 54
<211> LENGTH: 6
<212> TYPE: PRT
<213> ORGANISM: Artificial sequence
<220> FEATURE:
<223> OTHER INFORMATION: Mutant

<400> SEQUENCE: 54

Leu Leu Thr Asn Tyr Ile
1               5

<210> SEQ ID NO 55
<211> LENGTH: 6
<212> TYPE: PRT
<213> ORGANISM: Artificial sequence
<220> FEATURE:
<223> OTHER INFORMATION: Mutant

<400> SEQUENCE: 55

Leu Leu Val Asn Tyr Ile
1               5

<210> SEQ ID NO 56
<211> LENGTH: 6
<212> TYPE: PRT
<213> ORGANISM: Artificial sequence
<220> FEATURE:
<223> OTHER INFORMATION: Mutant

<400> SEQUENCE: 56

Leu Leu Trp Asn Tyr Ile
1               5

-continued

<210> SEQ ID NO 57
<211> LENGTH: 6
<212> TYPE: PRT
<213> ORGANISM: Artificial sequence
<220> FEATURE:
<223> OTHER INFORMATION: Mutant

<400> SEQUENCE: 57

Leu Leu Leu Asn Met Ile
1               5

<210> SEQ ID NO 58
<211> LENGTH: 6
<212> TYPE: PRT
<213> ORGANISM: Artificial sequence
<220> FEATURE:
<223> OTHER INFORMATION: Mutant

<400> SEQUENCE: 58

Leu Leu Leu Asn Ile Ile
1               5

<210> SEQ ID NO 59
<211> LENGTH: 6
<212> TYPE: PRT
<213> ORGANISM: Artificial sequence
<220> FEATURE:
<223> OTHER INFORMATION: Mutant

<400> SEQUENCE: 59

Leu Leu Leu Asn Leu Ile
1               5

<210> SEQ ID NO 60
<211> LENGTH: 6
<212> TYPE: PRT
<213> ORGANISM: Artificial sequence
<220> FEATURE:
<223> OTHER INFORMATION: Mutant

<400> SEQUENCE: 60

Leu Leu Leu Asn Val Ile
1               5

<210> SEQ ID NO 61
<211> LENGTH: 6
<212> TYPE: PRT
<213> ORGANISM: Artificial sequence
<220> FEATURE:
<223> OTHER INFORMATION: Mutant

<400> SEQUENCE: 61

Leu Leu Ser Asn Ile Ile
1               5

<210> SEQ ID NO 62
<211> LENGTH: 6
<212> TYPE: PRT
<213> ORGANISM: Artificial sequence
<220> FEATURE:
<223> OTHER INFORMATION: Mutant

<400> SEQUENCE: 62

Leu Leu Thr Asn Ile Ile
1               5

-continued

```
<210> SEQ ID NO 63
<211> LENGTH: 6
<212> TYPE: PRT
<213> ORGANISM: Artificial sequence
<220> FEATURE:
<223> OTHER INFORMATION: Mutant

<400> SEQUENCE: 63

Leu Leu Thr Asn Val Ile
1               5


<210> SEQ ID NO 64
<211> LENGTH: 6
<212> TYPE: PRT
<213> ORGANISM: Artificial sequence
<220> FEATURE:
<223> OTHER INFORMATION: Mutant

<400> SEQUENCE: 64

Leu Leu Ser Asn Val Ile
1               5


<210> SEQ ID NO 65
<211> LENGTH: 6
<212> TYPE: PRT
<213> ORGANISM: Artificial sequence
<220> FEATURE:
<223> OTHER INFORMATION: Mutant

<400> SEQUENCE: 65

Leu Leu Val Asn Leu Ile
1               5


<210> SEQ ID NO 66
<211> LENGTH: 6
<212> TYPE: PRT
<213> ORGANISM: Artificial sequence
<220> FEATURE:
<223> OTHER INFORMATION: Mutant

<400> SEQUENCE: 66

Leu Leu Trp Asn Leu Ile
1               5
```

PPO POLYPEPTIDES TOLERANT TO PPO-INHIBITING HERBICIDES AND USE THEREOF

CROSS-REFERENCE TO RELATED APPLICATIONS

This patent application is the U.S. National Stage of International Patent Application No. PCT/CN2022/082947, filed Mar. 25, 2022, which claims priority to Chinese Patent Application No. 202210136187.2, filed Feb. 15, 2022 and Chinese Patent Application No. 202110361141.6, filed Apr. 2, 2021, each of which is hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 230,644 Byte ASCII (Text) file named "IEC220164PUS_ST25.TXT," created on Mar. 25, 2022.

TECHNICAL FIELD

The present invention relates to the field of biotechnology, and specifically relates to PPO polypeptides tolerant to PPO-inhibiting herbicides and use thereof.

BACKGROUND OF THE INVENTION

Weeds are one of the key factors affecting crop yield in agricultural production. Herbicides are the main technical means for weed control. Herbicide modes of action are classified into 28 categories by Weed Science Society of America (weedscience.org) according to the different target sites of herbicides in plants, wherein Group 14 (Group 14; HRAC GROUP E) is the Protoporphyrinogen IX oxidase (PPO) inhibitor (http://www.weedscience.org/).

Protoporphyrinogen IX oxidase (PPOX, PPX or PPO; EC 1.3.3.4) is the last common enzyme in the synthetic pathway of chlorophyll and heme. Protoporphyrinogen IX is converted into Protoporphyrin IX catalyzed by PPO in the presence of oxygen molecules.

PPO is an important herbicide target site in plants which inhibits proporphyrinogen oxidase in plants and results in the intracellular accumulation of the substrate protoporphyrinogen that catalyses the reaction. The protoporphyrinogen accumulation in chloroplast and mitochondrion in cells leads to non-enzymatic oxidation of proporphyrinogen by $O_2$. Under light conditions, nonenzymatic oxidation produces singlet oxygen. Singlet oxygen results in the lipid oxidation in the endomembrane system, then brings about the oxidative damage of these endomembrane systems, thereby killing plant cells (Future Med Chem. 2014 April; 6(6): 597-599. doi: 10.4155/fmc.14.29).

The evolutionary relationship of PPO enzymes in the organism kingdom is studied by researching their sequence similarities, and PPO enzymes are divided into three categories: HemG, HemJ, and HemY. In most cases, a single species possesses only one of the categories. Among them, HemG is generally distributed in γ-proteobacteria, HemJ is distributed in α-proteobacteria and transferred into other proteobacterias and cyanobacteria, while HemY is the only PPO enzyme in eukaryotes (Genome Biol Evol. 2014 August; 6(8):2141-55. doi: 10.1093/gbe/evu170).

PPO genes have been identified from certain organisms. For example, these genes known by us include the PPO1 gene (Genbank ID Y13465) and PPO2 gene (Genbank ID Y13466) of *Nicotiana tabacum*, the PPO gene of *Arabidopsis thaliana* (Genbank ID D83139), the HemY gene of *Bacillus subtilis* (Genbank ID M97208), the PPO gene of mice (Genbank ID D45185), the PPO gene of human beings (Genbank ID D38537), the PPO gene of *Saccharomyces cerevisiae* (Genbank ID Z71381), the hemG gene of *Escherichia coli* (Genbank ID X68660), etc.

Generally, there are at least two kinds of PPO genes in plant, named as PPO1 and PPO2, respectively, wherein PPO1 is generally located in the chloroplast of plants while PPO2 is in the mitochondrion of plant cells. However, the mRNA of the PPO2 gene in certain Amaranthaceae plants differ in translation initiation sites (TIS), thereby produces PPO2 polypeptides of different lengths. For example, the PPO2 gene in spinach (*Spinacia oleracea* L) expresses two PPO2 proteins with the molecular weight of 58 KD and 56 KD, respectively, and the two proteins have the difference of 26 polypeptides in length. Wherein, the longer one is located in chloroplasts and the shorter one in mitochondria (J Biol Chem. 2001 Jun. 8; 276(23):20474-81. doi: 10.1074/jbc.M101140200. Epub 2001 Mar. 23).

When PPO activity is inhibited by a certain compound, the production of chlorophyll and heme will also be inhibited. The substrate protoporphyrinogen IX will be separated from the normal porphyrin biosynthetic pathway, rapidly separating from chloroplast and entering into cytoplasm. The protoporphyrinogen IX is oxidized to protoporphyrin IX and accumulates on cell membrane. The accumulated protoporphyrin IX produces high active singlet oxygens ($^1O_2$) with the action of light and oxygen molecules and causes destruction of cell membrane, leading to rapid death of plant cells. Due to the use of PPO-inhibiting herbicides, cases of weeds resistant to certain PPO-inhibiting herbicides have been reported. (Pest Manag Sci. 2014 September; 70(9): 1358-66. doi: 10.1002/ps.3728. Epub 2014 Feb. 24).

For example, in tall waterhemp (*Amaranthus tuberculatus*), resistance to herbicide lactofen is conferred by the deletion of glycine (ΔG210) at position 210 of the PPO2L gene (Proc Natl Acad Sci USA. 2006 Aug. 15; 103(33): 12329-34. doi: 10.1073/pnas.0603137103. Epub 2006 Aug. 7).

In palmer amaranth (*Amaranthus palmeri*), resistance to herbicide fomesafen is conferred by the mutation of arginine to glycine or methionine at position 98 of the PPO2 gene (R98G, R98M) (Pest Manag Sci. 2017 August; 73(8):1559-1563. doi: 10.1002/ps.4581. Epub 2017 May 16).

In palmer amaranth (*Amaranthus palmeri*), resistance to fomesafen is conferred by the mutation of glycine to alanine (G399A) at position 399 of the PPO2 gene (Front Plant Sci. 2019 May 15; 10:568. doi: 10.3389/fpls.2019.00568. eCollection 2019).

In ragweed (*Ambrosia artemisiifolia*), resistance to flumioxazin is conferred by the mutation of arginine to leucine at position 98 of the PPO2 gene (R98L) (Weed Science, 60(3):335-344 (2012)).

In goosegrass (*Eleusine indica*), resistance to oxadiazon is conferred by the mutation of alanine to threonine at position 212 of the PPO1 gene (A212T) (Pest Manag Sci. 2020 May; 76(5):1786-1794. doi: 10.1002/ps.5703. Epub 2020 Jan. 23).

BRIEF SUMMARY OF THE INVENTION

The present invention relates to a PPO polypeptide or a bioactive fragment thereof tolerant to a PPO-inhibiting herbicide.

The present invention also relates to an isolated polynucleotide and the corresponding plant genome, vector construct, or host cell.

In the other aspect, the present invention provides a producing method of a plant cell or plant to gain or improve its tolerance to a PPO-inhibiting herbicide, and a plant produced by the method.

In another aspect, the present invention provides a method of enabling a plant to gain or improve tolerance to a PPO-inhibiting herbicide.

The present invention also provides a method of gaining or improving the tolerance of a plant cell, plant tissue, plant part or plant to a PPO-inhibiting herbicide.

The present invention further relates to use of the PPO polypeptide or a bioactive fragment thereof or the polynucleotide for gaining or improving tolerance of a host cell, plant cell, plant issue, plant part or plant to a PPO-inhibiting herbicide.

The present invention further relates to a method for controlling weeds in a plant cultivation site.

BRIEF DESCRIPTION OF THE SEVERAL VIEWS OF THE DRAWING(S)

FIG. 1 shows the alignment of PPO amino acid sequences from different plants, wherein the marked box indicates the conserved amino acid motifs at the screening sites, representing successively from top to bottom: rice (*Oryza sativa* L.), corn (*Zea mays*), *Arabidopsis thaliana*, soybean (*Glycine max*), tobacco (*Nicotiana tabacum*), *sorghum* (*Sorghum bicolor*), tomato (*Solanum lycopersicum*), barley (*Hordeum vulgare*), oilseed rape (*Brassica napus*), peanut (*Arachis hypogaea*), wheat (*Triticum aestivum*), cabbage (*Brassica oleracea*), foxtail millet (*Setaria italica*), radish (*Raphanus sativus*), potato (*Solanum tuberosum*), upland cotton (*Gossypium hirsutum*), yam (*Dioscorea cayenensis*), cassava (*Manihot esculenta*), pepper (*Capsicum annuum*), squash (*Cucurbita moschata*), cucumber (*Cucumis sativus*), lettuce (*Lactuca sativa*), sesame (*Sesamum indicum*), sunflower (*Helianthus annuus*), mulberry (*Morus alba*), cowpea (*Vigna unguiculata*), strawberry (*Fragaria ananassa*), apple (*Malus domestica*), peach (*Prunus persica*), cherry (*Prunus pseudocerasus*), apricot (*Prunus armeniaca*), grape vine (*Vitis vinfera*), *papaya* (*Carica papaya*), alfalfa (*Medicago sativa*).

Figure 10:
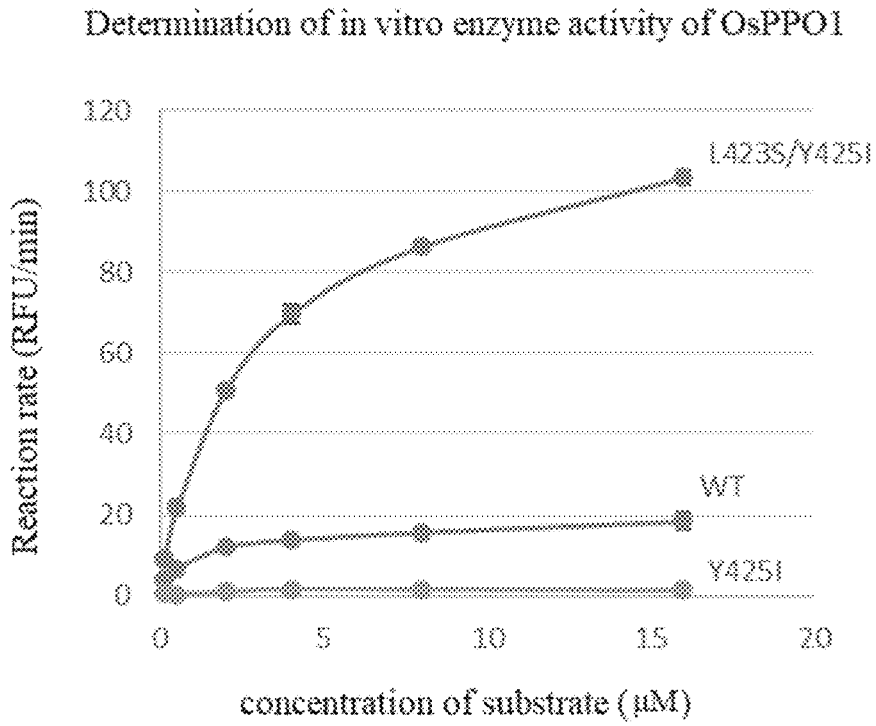

FIG. 10 shows mutant enzyme activity determination. Differences between enzymatic kinetics curves of the rice OsPPO1 wild-type (indicated as WT), Y425I, and L423S/Y425I are shown as well. The enzyme activity L423S/Y425 mutant is higher than WT, while the enzyme activity Y425I is lower than WT.

Figure 11:
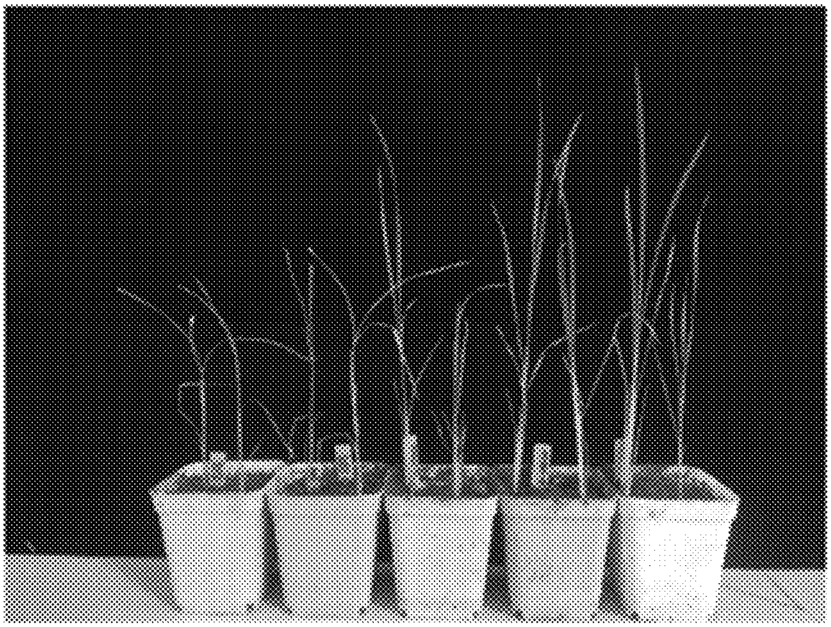

FIG. 11 shows the growth performance of rice seedling strains with homologous replacement at L423S/Y425I site when treated with compound A at the rate of 9 g/ha in comparison with wild-type strains.

Figure 12:
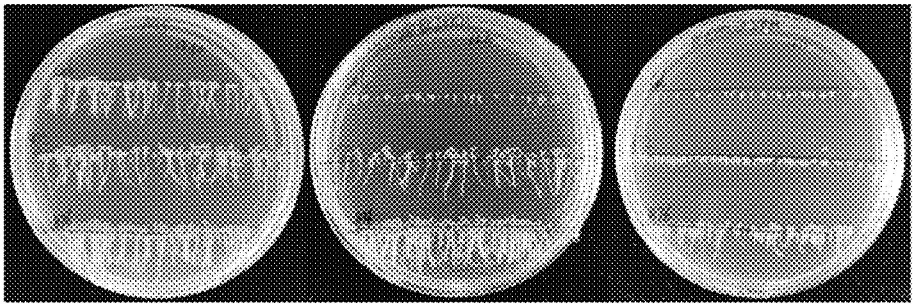

FIG. 12 shows the overexpressed soybean PPO1 WT and L430S/Y432I *Arabidopsis thaliana* seed treated with different concentrations of compound A. Compared with wild-type *Arabidopsis thaliana*, both the overexpressed soybean PPO1 WT and L430S/Y432I show certain level of tolerance to compound A in *Arabidopsis thaliana*, but the tolerance of the overexpressed L430S/Y432I to compound A is much higher than that of the overexpressed wild-type. Wherein, wild-type indicates wild-type *Arabidopsis thaliana*; pHSE-GmPPO1 WT indicates overexpressed soybean PPO1; pHSE-GmPPO1 L430S/Y432I indicates overexpressed soybean PPO1 L430S/Y432I.

Figure 13:
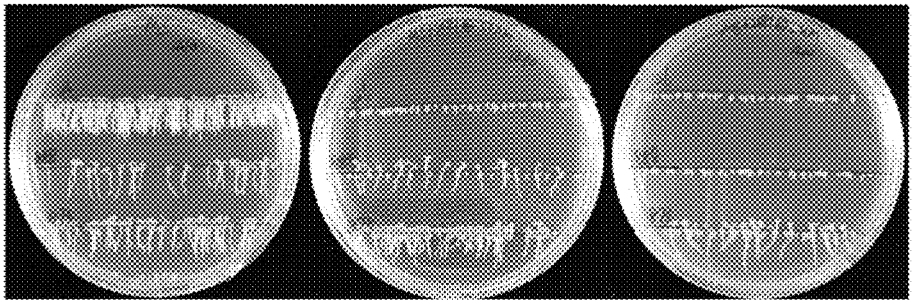

FIG. 13 shows the overexpressed oilseed rape PPO1 WT and L424S/Y426I *Arabidopsis thaliana* seed treated with different concentrations of compound A. Compared with wild-type *Arabidopsis thaliana*, both the overexpressed oilseed rape PPO1 WT and L424S/Y426I show certain level of tolerance to compound A in *Arabidopsis thaliana*, but the tolerance of the overexpressed L424S/Y426I to compound A is much higher than that of the overexpressed wild-type. Wherein, wild-type indicates wild-type *Arabidopsis thaliana*; pHSE-BnPPO1-C5 WT indicates overexpressed oilseed rape PPO1; pHSE-BnPPO1-C5L424S/Y426I indicates overexpressed oilseed rape PPO1 L424S/Y426I.

Figure 14:
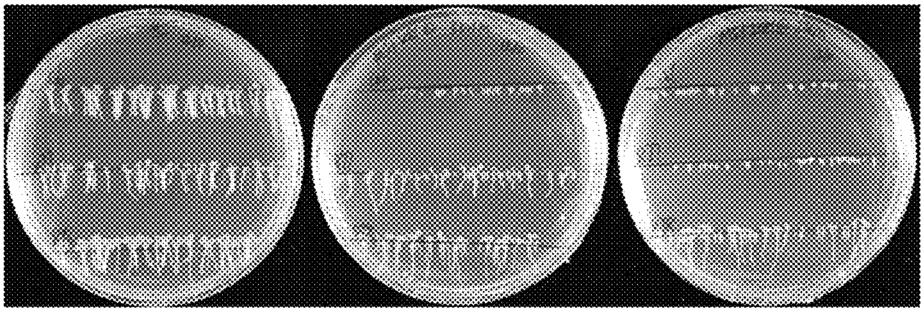

FIG. 14 shows the overexpressed corn PPO1 WT and L424W/Y426L *Arabidopsis thaliana* seed treated with different concentrations of compound A. Compared with wild-type *Arabidopsis thaliana*, both the overexpressed corn PPO1 WT and L424W/Y426L show certain level of tolerance to compound A in *Arabidopsis thaliana*, but the tolerance of the overexpressed L424W/Y426 μL to compound A is much higher than that of the overexpressed wild-type. Wherein, wild-type indicates wild-type *Arabidopsis thaliana*; pHSE-ZmPPO1 WT indicates overexpressed corn PPO1; pHSE-ZmPPO1 L424W/Y426 L indicates overexpressed corn PPO1 L424W/Y426L.

Figure 15:
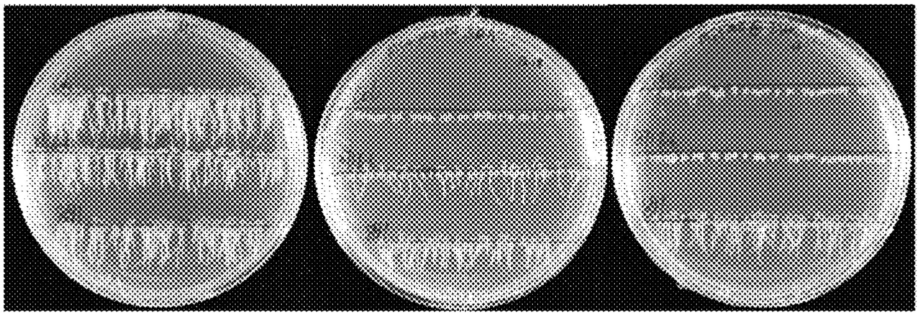

FIG. 15 shows the overexpressed rice PPO1 WT and L423S/Y425I *Arabidopsis thaliana* seed treated with different concentrations of compound A. Compared with wild-type *Arabidopsis thaliana*, both the overexpressed rice PPO1 WT and L423S/Y425I show certain level of tolerance to compound A in *Arabidopsis thaliana*, but the tolerance of the overexpressed L423S/Y425I to compound A is much higher than that of the overexpressed wild-type. Wherein, wild-type indicates wild-type *Arabidopsis thaliana*; pHSE-OsPPO1 WT indicates overexpressed rice PPO1; pHSE-OsPPO1 L423S/Y425I indicates overexpressed rice PPO1 L423S/Y425I.

Figure 16:
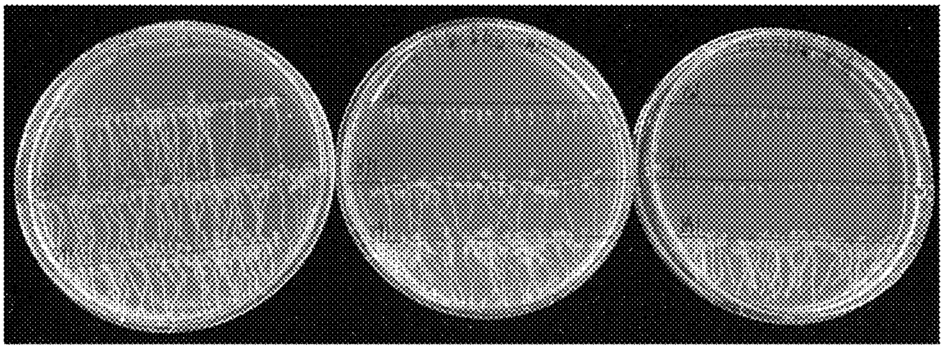

FIG. 16 shows the overexpressed rice PPO1 WT and L423S/Y425I *Arabidopsis thaliana* seed treated with different concentrations of flumioxazin. Compared with wild-type *Arabidopsis thaliana*, both the overexpressed rice PPO1 WT and L423S/Y425I show certain level of tolerance to flumioxazin in *Arabidopsis thaliana*, but the flumioxazin tolerance of the overexpressed L423S/Y425I is much higher than that of the overexpressed wild-type. Wherein, wild-type indicates wild-type *Arabidopsis thaliana*; pHSE-OsPPO1 WT indicates overexpressed rice PPO1; pHSE-OsPPO1 L423S/Y425I indicates overexpressed rice PPO1 L423S/Y425I.

Figure 17:
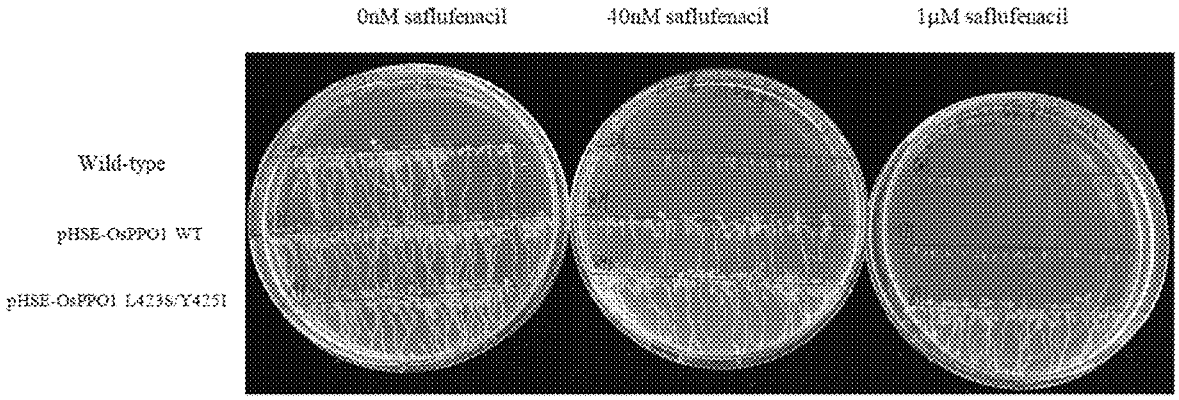

FIG. 17 shows the overexpressed rice PPO1 WT and L423S/Y425I *Arabidopsis thaliana* seed treated with different concentrations of saflufenacil. Compared with the wild type *Arabidopsis thaliana*, both the overexpressed rice PPO1 WT and L423S/Y425I show certain level of tolerance to saflufenacil in *Arabidopsis thaliana*, but the saflufenacil tolerance of overexpressed L423S/Y425I is much higher than that of the overexpressed wild type. Wherein, wild-type indicates wild-type *Arabidopsis thaliana*; pHSE-OsPPO1 WT indicates overexpressed rice PPO1; pHSE-OsPPO1 L423S/Y425I indicates overexpressed rice PPO1 L423S/Y425I.

Figure 18:
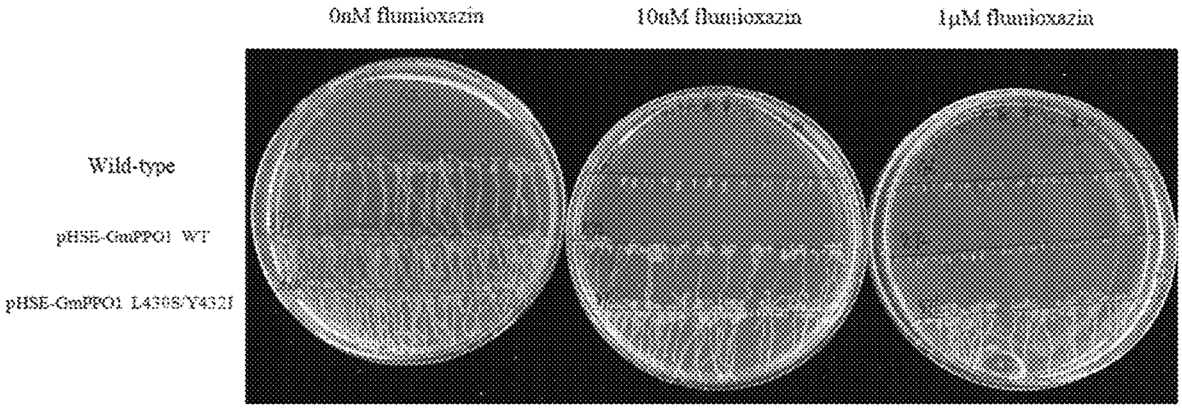

FIG. 18 shows the overexpressed soybean PPO1 WT and L430S/Y432I *Arabidopsis thaliana* seed treated with different concentrations of flumioxazin. Compared with the wild type *Arabidopsis thaliana*, both the overexpressed soybean PPO1 WT and L430S/Y432I show certain level of tolerance to flumioxazin in *Arabidopsis thaliana*, but the flumioxazin tolerance of overexpressed L430S/Y432I is much higher than that of the overexpressed wild type. Wherein, wild-type indicates wild-type *Arabidopsis thaliana*; pHSE-GmPPO1 WT indicates overexpressed soybean PPO1; pHSE-GmPPO1 L430S/Y432I indicates overexpressed soybean PPO1 L430S/Y432I.

Figure 19:
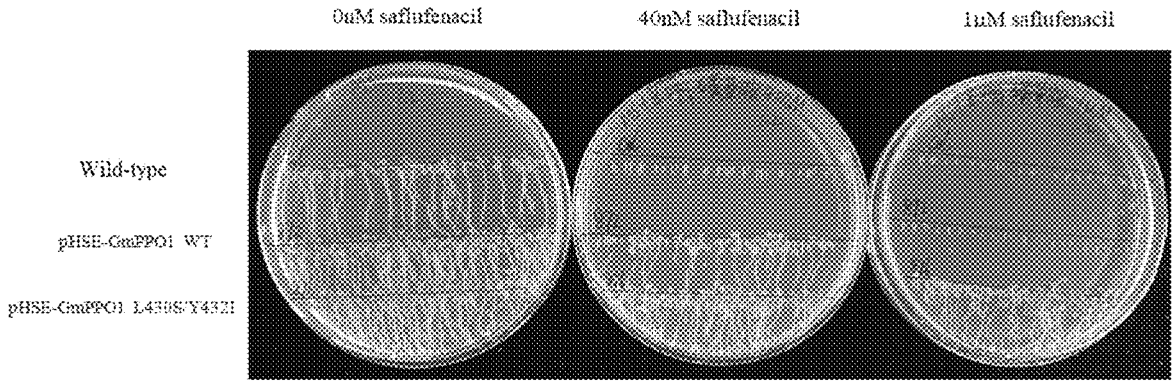

FIG. 19 shows the overexpressed soybean PPO1 WT and L430S/Y432I *Arabidopsis thaliana* seed treated with different concentrations of saflufenacil. Compared with the wild type *Arabidopsis thaliana*, both the overexpressed soybean PPO1 WT and L430S/Y432I show certain level of tolerance to saflufenacil in *Arabidopsis thaliana*, but the saflufenacil tolerance of overexpressed L430S/Y432I is much higher than that of the overexpressed wild type. Wherein, wild-type indicates wild-type *Arabidopsis thaliana*; pHSE-GmPPO1 WT indicates overexpressed soybean PPO1; pHSE-GmPPO1 L430S/Y432I indicates overexpressed soybean PPO1 L430S/Y432I.

Figure 20:
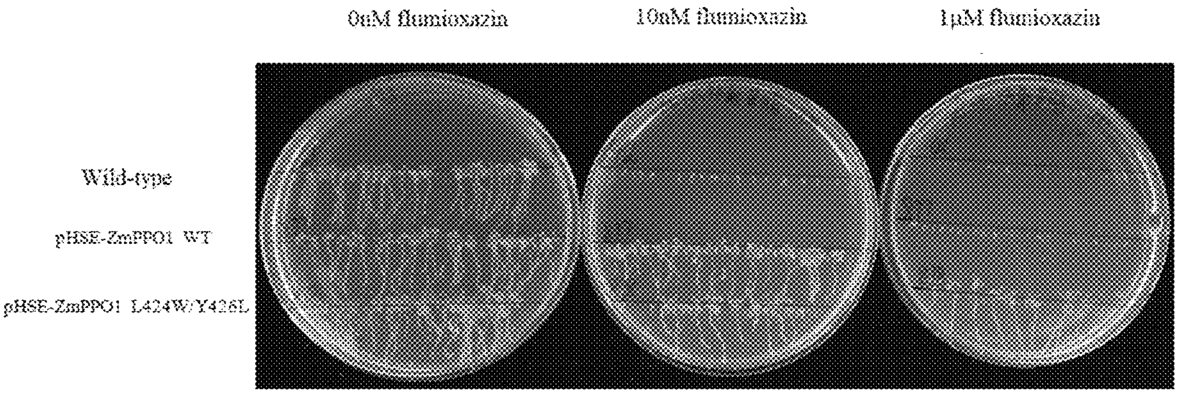

FIG. 20 shows the overexpressed corn PPO1 WT and L424W/Y426 L *Arabidopsis thaliana* seed treated with different concentrations of flumioxazin. Compared with the wild type *Arabidopsis thaliana*, both the overexpressed corn PPO1 WT and L424W/Y426 L show certain level of tolerance to flumioxazin in *Arabidopsis thaliana*, but the flumioxazin tolerance of overexpressed L424W/Y426 L is much higher than that of the overexpressed wild type. Wherein, wild-type indicates wild-type *Arabidopsis thaliana*; pHSE-ZmPPO1 WT indicates overexpressed corn PPO1; pHSE-ZmPPO1 L424W/Y426 L indicates overexpressed corn PPO1 L424W/Y426L.

Figure 21:
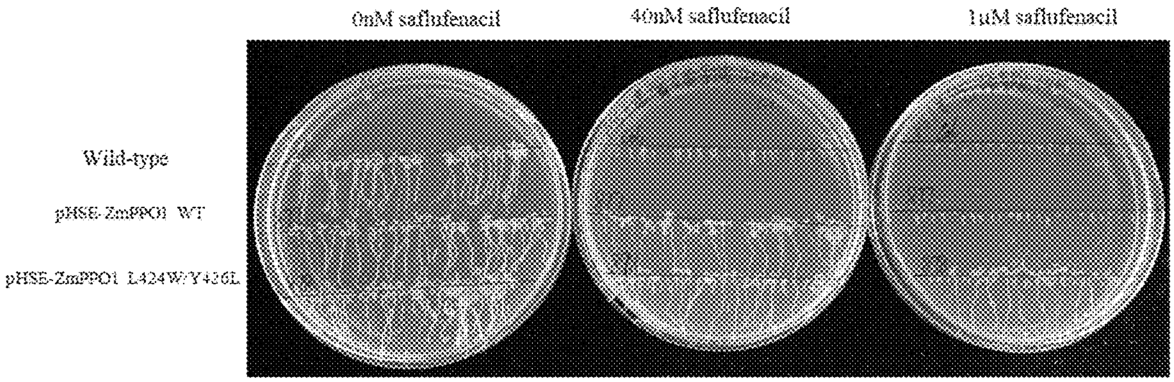

FIG. 21 shows the overexpressed corn PPO1 WT and L424W/Y426 L *Arabidopsis thaliana* seed treated with different concentrations of saflufenacil. Compared with the wild type *Arabidopsis thaliana*, both the overexpressed corn PPO1 WT and L424W/Y426 L show certain level of tolerance to saflufenacil in *Arabidopsis thaliana*, but the saflufenacil tolerance of overexpressed L424W/Y426 L is much higher than that of the overexpressed wild type. Wherein, wild-type indicates wild-type *Arabidopsis thaliana*; pHSE-ZmPPO1 WT indicates overexpressed corn PPO1; pHSE-ZmPPO1 WTL424W/Y426 L indicates overexpressed corn PPO1 L424W/Y426L.

Figure 22:
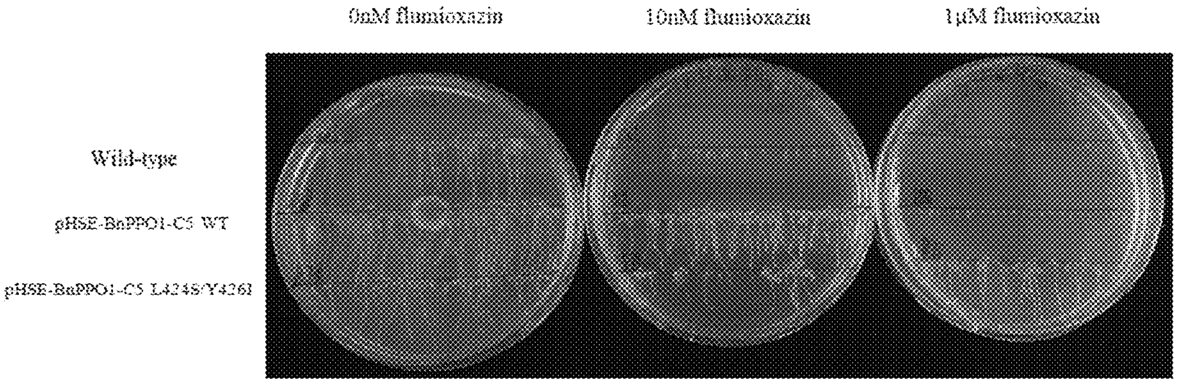

FIG. 22 shows the overexpressed oilseed rape PPO1 WT and L424S/Y426I *Arabidopsis thaliana* seed treated with different concentrations of flumioxazin. Compared with the wild type *Arabidopsis thaliana*, both the overexpressed oilseed rape PPO1 WT and L424S/Y426I show certain level of tolerance to flumioxazin in *Arabidopsis thaliana*, but the flumioxazin tolerance of overexpressed L424S/Y426I is much higher than that of the overexpressed wild type. Wherein, wild-type indicates wild-type *Arabidopsis thaliana*; pHSE-BnPPO1-C5 WT indicates overexpressed oilseed rape PPO1; pHSE-BnPPO1-C5 L424S/Y426I indicates overexpressed oilseed rape PPO1 L424S/Y426I.

Figure 23:
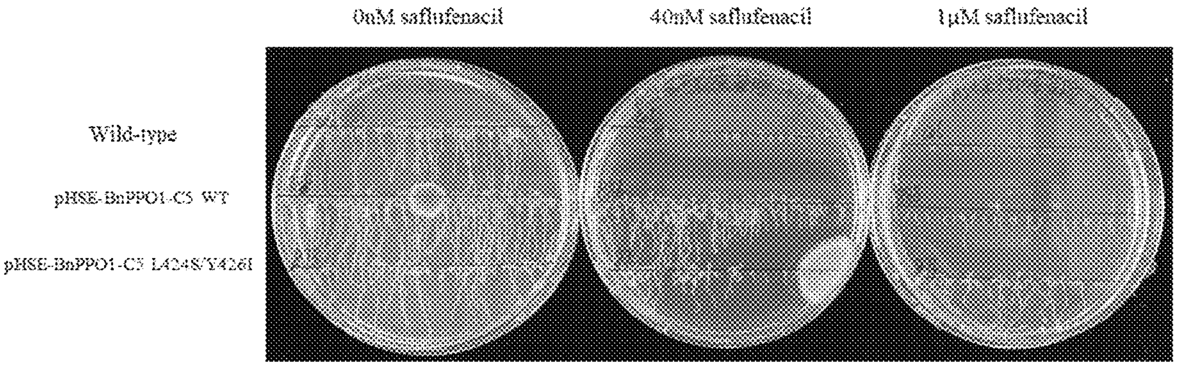

FIG. 23 shows the overexpressed oilseed rape PPO1 WT and L424S/Y426I *Arabidopsis thaliana* seed treated with different concentrations of saflufenacil. Compared with the wild type *Arabidopsis thaliana*, both the overexpressed oilseed rape PPO1 WT and L424S/Y426I show certain level of tolerance to saflufenacil in *Arabidopsis thaliana*, but the saflufenacil tolerance of overexpressed L424S/Y426I is much higher than that of the overexpressed wild type. Wherein, wild-type indicates wild-type *Arabidopsis thaliana*; pHSE-BnPPO1-C5 WT indicates overexpressed oilseed rape PPO1; pHSE-BnPPO1-C5 L424S/Y426I indicates overexpressed oilseed rape PPO1 L424S/Y426I.

Figure 24:
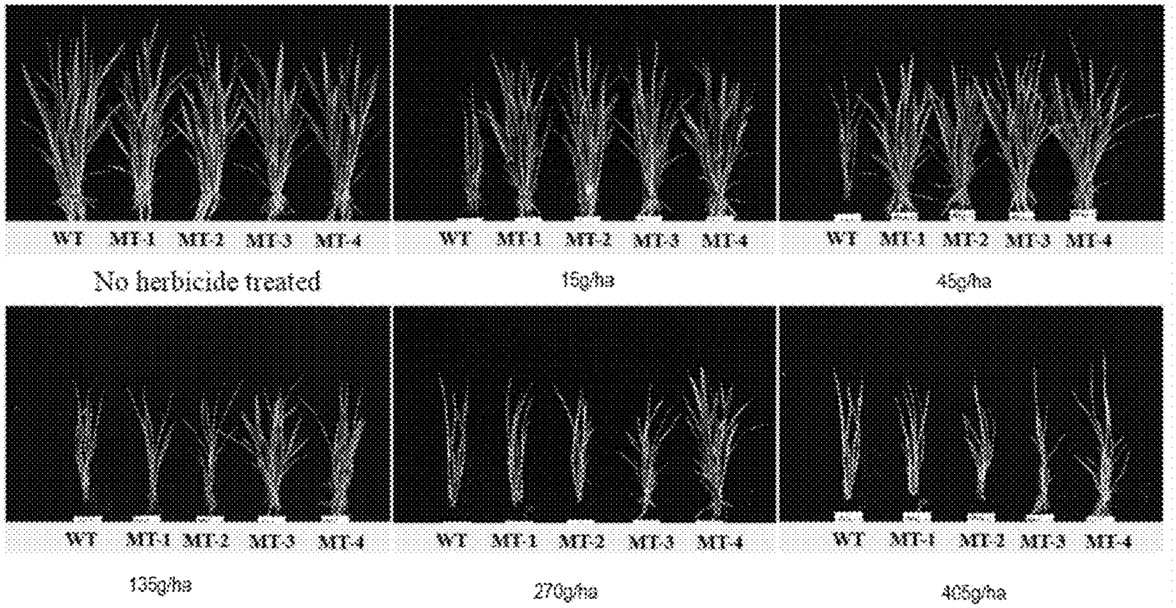

FIG. 24 shows the test result of overexpressed rice PPO1 WT and L423S/Y425I rice seedlings sprayed with different concentrations of compound A. Wherein, WT indicates Huaidao No. 5 wild-type; MT1 and MT2 indicate overexpressed rice PPO1 WT; MT3 and MT4 indicate overexpressed rice PPO1 L423S/Y425I.

| SEQ ID NO | Name |
|---|---|
| SEQ ID NO: 1 | Amino-acid sequence of PPO1 from wild-type rice (OsPPO1 WT) |
| SEQ ID NO: 2 | Amino-acid sequence of PPO1 from wild-type corn (ZmPPO1 WT) |
| SEQ ID NO: 3 | Amino-acid sequence of PPO1 wild-type from oilseed rape (BnPPO1-C5) |
| SEQ ID NO: 4 | Amino-acid sequence of PPO1 from wild-type oilseed rape (BnPPO1-A10) |
| SEQ ID NO: 5 | Amino-acid sequence of PPO1 from wild-type peanut (AhPPO1-A) |
| SEQ ID NO: 6 | Amino-acid sequence of PPO1 from wild-type peanut (AhPPO1-B) |
| SEQ ID NO: 7 | Amino-acid sequence of PPO1 from wild-type soybean (GmPPO1) |
| SEQ ID NO: 8 | Amino-acid sequence of PPO1 from wild-type sorghum (SbPPO1) |
| SEQ ID NO: 9 | Amino-acid sequence of PPO1 from wild-type wheat (TaPPO1-A) |
| SEQ ID NO: 10 | Amino-acid sequence of PPO1 from wild-type wheat (TaPPO1-B) |
| SEQ ID NO: 11 | Amino-acid sequence of PPO1 from wild-type wheat (TaPPO1-D) |
| SEQ ID NO: 12 | Amino-acid sequence of PPO1 form wild-type tomato (SlPPO1) |

-continued

| SEQ ID NO | Name |
|---|---|
| SEQ ID NO: 13 | Amino-acid sequence of PPO1 from wild-type potato (StPPO1) |
| SEQ ID NO: 14 | Amino-acid sequence of PPO1 form wild-type tobacco (NtPPO1) |
| SEQ ID NO: 15 | Amino-acid sequence of PPO1 from wild-type *Arabidopsis thaliana* (AtPPO1) |
| SEQ ID NO: 16 | Amino-acid sequence of PPO1 from wild-type upland cotton (GhPPO1) |
| SEQ ID NO: 17 | Amino-acid sequence of PPO1 from wild-type radish (RsPPO1) |
| SEQ ID NO: 18 | Amino-acid sequence of PPO1 from wild-type foxtail millet (SiPPO1) |
| SEQ ID NO: 19 | Amino-acid sequence of PPO1 form wild-type cabbage (BoPPO1) |
| SEQ ID NO: 20 | Amino-acid sequence of PPO1 from rice mutant (OsPPO1 L423S) |
| SEQ ID NO: 21 | Amino-acid sequence of PPO1 from rice mutant (OsPPO1 L423I) |
| SEQ ID NO: 22 | Amino-acid sequence of PPO1 from rice mutant (OsPPO1 L423G) |
| SEQ ID NO: 23 | Amino-acid sequence of PPO1 from rice mutant (OsPPO1 Y425M) |
| SEQ ID NO: 24 | Amino-acid sequence of PPO1 from rice mutant (OsPPO1 Y425I) |
| SEQ ID NO: 25 | Amino-acid sequence of PPO1 from rice mutant (OsPPO1 Y425V) |
| SEQ ID NO: 26 | Amino-acid sequence of PPO1 from rice mutant (OsPPO1 L423S/Y425I) |
| SEQ ID NO: 27 | Amino-acid sequence of PPO1 from corn mutant (ZmPPO1 L424T/Y426V) |
| SEQ ID NO: 28 | Amino-acid sequence of PPO1 form corn mutant (ZmPPO1 L424S/Y426V) |
| SEQ ID NO: 29 | Amino-acid sequence of PPO1 from corn mutant (ZmPPO1 L424V/Y426L) |
| SEQ ID NO: 30 | Amino-acid sequence of PPO1 from corn mutant (ZmPPO1 L424W/Y426L) |
| SEQ ID NO: 31 | Amino-acid sequence of PPO1 form corn mutant (ZmPPO1 L424S/Y426I) |
| SEQ ID NO: 32 | Amino-acid sequence of PPO1 from oilseed rape mutant (BnPPO1-C5 L424S/Y426I) |
| SEQ ID NO: 33 | Amino-acid sequence of PPO1 from oilseed rape mutant (BnPPO1-A10 L423S/Y425I) |
| SEQ ID NO: 34 | Amino-acid sequence of PPO1 from peanut mutant (AhPPO1-A L445S/Y447I) |
| SEQ ID NO: 35 | Amino-acid sequence of PPO1 from peanut mutant (AhPPO1-B L439S/Y441I) |
| SEQ ID NO: 36 | Amino-acid sequence of PPO1 from soybean mutant (GmPPO1 L430S/Y432I) |
| SEQ ID NO: 37 | Amino-acid sequence of PPO1 from sorghum mutant (SbPPO1 L423S/Y425I) |
| SEQ ID NO: 38 | Amino-acid sequence of PPO1 form wheat mutant (TaPPO1-A L418S/Y420I) |
| SEQ ID NO: 39 | Amino-acid sequence of PPO1 from wheat mutant (TaPPO1-B L418S/Y420I) |
| SEQ ID NO: 40 | Amino-acid sequence of PPO1 form wheat mutant (TaPPO1-D L418S/Y420I) |
| SEQ ID NO: 41 | Amino-acid sequence of PPO1 form tomato mutant (SlPPO1 L445S/Y447I) |
| SEQ ID NO: 42 | Amino-acid sequence of PPO1 form potato mutant (StPPO1 L444S/Y446I) |
| SEQ ID NO: 43 | Amino-acid sequence of PPO1 from tobacco mutant (NtPPO1 L440S/Y442I) |
| SEQ ID NO: 44 | Amino-acid sequence of PPO1 form *Arabidopsis thaliana* mutant (AtPPO1 L423S/Y425I) |
| SEQ ID NO: 45 | Amino-acid sequence of PPO1 from upland cotton mutant (GhPPO1 L426S/Y428I) |
| SEQ ID NO: 46 | Amino-acid sequence of PPO1 from radish mutant (RsPPO1 L425S/Y427I) |
| SEQ ID NO: 47 | Amino-acid sequence of PPO1 from foxtail millet mutant (SiPPO1 L422S/Y424I) |
| SEQ ID NO: 48 | Amino-acid sequence of PPO1 from cabbage mutant (BoPPO1 L424S/Y426I) |
| SEQ ID NO: 49 | Amino-acid sequence of PPO1 from homologous replacement repair template of rice mutant (OsPPO1 L423S/Y425I) |

DETAILED DESCRIPTION OF THE INVENTION

Some terms used in the specification are defined as follows.

In the present invention, the term "herbicide" refers to an active ingredient that can kill, control or otherwise adversely modifies the growth of plants. The term "herbicide tolerance" or "herbicide resistance" refers to a situation that a plant continues to grow even after the treatment of a herbicide which are capable of killing normal or wild-type plants or inhibiting growth thereof, or weakening or ceasing plant growth ability compared to wild-type plants. The above herbicide includes PPO-inhibiting herbicides, which can be divided into pyrimidinediones, diphenyl-ethers, phenylpyrazoles, N-phenylphthalimides, thiadiazoles, oxadiazoles, triazolinones, oxazolidinediones, and other herbicides with different chemical structures.

Generally, if the PPO-inhibiting herbicides and/or other herbicidal compounds, as described herein and available to be employed in the context of the present invention, are capable of forming geometrical isomers such as E/Z isomers, both of themselves, pure isomers and mixtures thereof may be used in the compositions according to the invention. If the PPO-inhibiting herbicides and/or other herbicidal compounds as described herein have one or more centers of chirality and, as a consequence, are present as enantiomers or diastereomers, both of themselves, pure isomers and mixtures thereof may be used in the compositions according to the invention. If the PPO-inhibiting herbicides and/or other herbicidal compounds as described herein have ionizable functional groups, they can also be used in the form of their agriculturally acceptable salts. Suitable are, in general, the salts of those cations and the acid addition salts of those acids whose cations and anions, respectively, have no adverse effects on the activity of the active compounds. Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methyl-ammonium, isopropyl-ammonium, dimethyl-ammonium, diisopropyl-ammonium, trimethyl-ammonium, heptyl-ammonium, dodecyl-ammonium, tetradecyl-ammonium, tetramethyl-ammonium, tetraethyl-ammonium, tetrabutyl-ammonium, 2-hydroxyethyl-ammonium (olamine salt), 2-(2-hydroxyeth-1-oxy)eth-1-ylammonium (diglycolamine salt), di(2-hydroxyeth-1-yl) ammonium (diolamine salt), tris(2-hydroxyethyl) ammonium(trolamine salt), tris(2-hydroxypropyl) ammonium, benzyltrimethylammonium, benzyltriethylammonium and N,N,N-trimethylethanolammonium (choline salt), additionally phosphonium ions, sulfonium ions, preferably tri(C1-C4-alkyl)sulfonium such as trimethylsulfonium, and sulfoxonium ions, preferably tri(C1-C4-alkyl)sulfoxonium ions, and finally the salts of polybasic amines such as N,N-bis-(3-aminopropyl)methylamine and diethylenetriamine. Anions of useful acid addition salts are primarily irons of chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of C1-C4-alkanoic acids, preferably formate, acetate, propionate and butyrate.

The PPO-inhibiting herbicides and/or other herbicidal compounds as described herein having a carboxyl group can be employed in the form of an acid, in the form of an agriculturally suitable salt as mentioned above or else in the form of an agriculturally acceptable derivative, for example as amides such as mono- and di-C1-C6-alkylamides or arylamides, as esters such as allylesters, propargyl esters, C1-C10-alkyl esters, alkoxyalkyl esters, tefuryl ((tetrahydrofuran-2-yl)methyl) esters and also as thioesters such as C1-C10-alkylthio esters. Preferred mono- and di-C1-C6-alkylamides are methyl and dimethylamides. Preferred arylamides are, for example, anilides and 2-chloroanilides. Preferred alkyl esters are, for example, methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred C1-C4-alkoxy-C1-C4-alkyl esters are the straight-chain or branched C1-C4-alkoxy ethyl esters, for example the 2-methoxyethylester, 2-ethoxyethylester, 2-butoxyethyl (butotyl)ester, 2-butoxypropyl ester or 3-butoxypropyl ester. An example of a straight-chain or branched C1-C10-alkylthio ester is the ethylthio ester.

In an exemplary embodiment, the pyrimidinediones herbicides include but are not limited to, butafenacil (CAS NO: 134605-64-4), saflufenacil (CAS NO: 372137-35-4), benzfendizone (CAS NO:158755-95-4), tiafenacil (CAS NO: 1220411-29-9), [3-[2-Chloro-4-fluoro-5-(1-methyl-6-trifluoromethyl-2,4-dioxo-1,2,3,4-tetrahydropyrimidine-3-yl) phenoxy]-2-pyridyloxy]acetic acid ethyl ester (Epyrifenacil, CAS NO: 353292-31-6), 1-Methyl-6-trifluoromethyl-3-(2, 2,7-trifluoro-3-oxo-4-prop-2-ynyl-3,4-dihydro-2H-benzo[1, 4]oxazin-6-yl)-1H-pyrimidine-2,4-dione (CAS NO: 1304113-05-0),3-[7-chloro-5-fluoro-2-(trifluoromethyl)-1H-benzimidazol-4-yl]-1-methyl-6-(trifluoromethyl)-1H-pyrimidine-2,4-dione (CAS NO: 212754-02-4), flupropacil (CAS NO: 120890-70-2), isoxazoline-containing uracils disclosed in CN105753853A (eg. compound

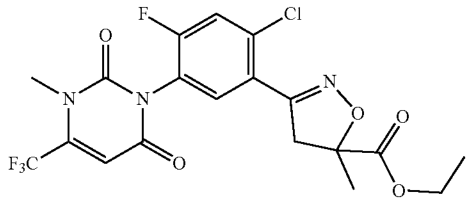), uracil pyridines disclosed in WO2017/202768, and uracils disclosed in WO2018/019842.

The diphenyl-ethers herbicides include but are not limited to, fomesafen (CAS NO: 72178-02-0), oxyfluorfen (CAS NO: 42874-03-3), aclonifen (CAS NO:74070-46-5), lactofen (CAS NO: 77501-63-4), chlomethoxyfen (CAS NO: 32861-85-1), chlornitrofen (CAS NO: 1836-77-7), fluoroglycofen-ethyl (CAS NO: 77501-90-7), acifluorfen or sodium salt (CAS NO: 50594-66-6 or 62476-59-9), bifenox (CAS NO: 42576-02-3), ethoxyfen (CAS NO: 188634-90-4), ethoxyfen-ethyl (CAS NO: 131086-42-5), fluoronitrofen (CAS NO: 13738-63-1), furyloxyfen (CAS NO: 80020-41-3), nitrofluorfen (CAS NO: 42874-01-1) and halosafen (CAS NO: 77227-69-1).

The phenylpyrazoles herbicides include but are not limited to, pyraflufen-ethyl (CAS NO: 129630-19-9) and fluazolate (CAS NO: 174514-07-9).

The N-Phenyl-imides herbicides include but are not limited to, flumioxazin (CAS NO: 103361-09-7), cinidon-ethyl (CAS NO: 142891-20-1), flumipropyn (CAS NO: 84478-52-4) and flumiclorac-pentyl (CAS NO: 87546-18-7).

The thiadiazoles herbicides include but are not limited to, fluthiacet-methyl (CAS NO: 117337-19-6), fluthiacet (CAS NO: 149253-65-6) and thidiazimin (CAS NO: 123249-43-4).

The oxadiazoles herbicides include but are not limited to, oxadiargyl (CAS NO: 39807-15-3) and oxadiazon (CAS NO: 19666-30-9).

The triazolinones herbicides include but are not limited to, carfentrazone (CAS NO: 128621-72-7), carfentrazone-ethyl (CAS NO: 128639-02-1), sulfentrazone (CAS NO: 122836-35-5), azafenidin (CAS NO: 68049-83-2) and bencarbazone (CAS NO: 173980-17-1).

The oxazolidinediones herbicides include but are not limited to, pentoxazone (CAS NO: 110956-75-7).

Other herbicides include but are not limited to, pyraclonil (CAS NO: 158353-15-2), flufenpyr-ethyl (CAS NO: 188489-07-8), profluazol (CAS NO: 190314-43-3), trifludimoxazin (CAS NO: 1258836-72-4), N-ethyl-3-(2,6-dichloro-4-trifluoromethylphenoxy)-5-methyl-1H-pyrazole-1-carboxamide (CAS NO: 452098-92-9), N-tetrahydrofurfuryl-3-(2,6-dichloro-4-trifluoromethylphenoxy)-5-methyl-1H-pyrazole-1-carboxamide (CAS NO: 915396-43-9), N-ethyl-3-(2-chloro-6-fluoro-4-trifluoromethylphenoxy)-5-methyl-1H-pyrazole-1-carboxamide (CAS NO: 452099-05-7), N-tetrahydrofurfuryl-3-(2-chloro-6-fluoro-4-trifluoromethylphenoxy)-5-methyl-1H-pyrazole-1-carboxamide (CAS NO: 452100-03-7), 3-[7-Fluoro-3-oxo-4-(prop-2-ynyl)-3,4-dihydro-2H-benzo[1,4]oxazin-6-yl]-1,5-dimethyl-6-thioxo[1,3,5]triazinane-2,4-dione (CAS NO: 451484-50-7), 2-(2,2,7-trifluoro-3-oxo-4-prop-2-ynyl-3,4-dihydro-2H-benzo[1,4]oxazin-6-yl)-4,5,6,7-tetrahydroisoindole-1,3-dione (CAS NO: 1300118-96-0), Methyl (E)-4-[2-chloro-5-[4-chloro-5-(difluoromethoxy)-1H-methylpyrazol-3-yl]-4-fluorophenoxy]-3-methoxy-but-2-enoate (CAS NO: 948893-00-3), phenylpyridines disclosed in WO2016/120116, benzoxazinone derivatives disclosed in EP09163242.2, and compounds shown in general formula I

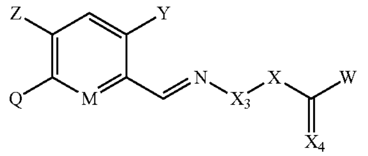

see patent CN202011462769.7);

in another exemplary embodiment, Q represents

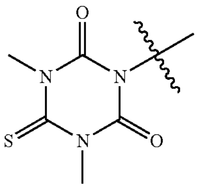,
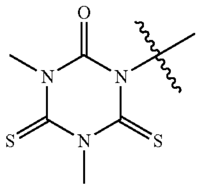,
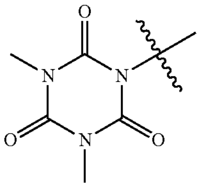,
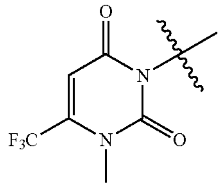,

-continued

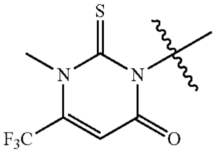, 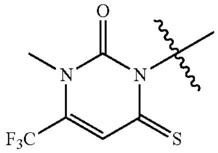,

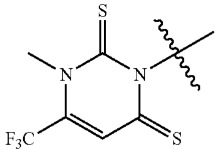, 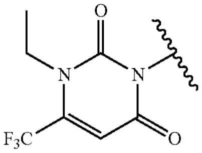,

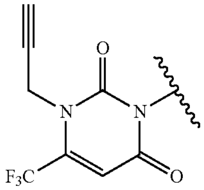, 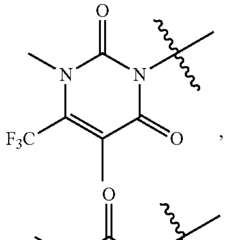,

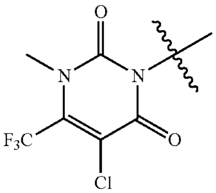, 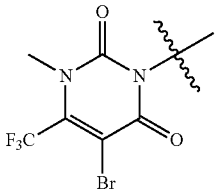,

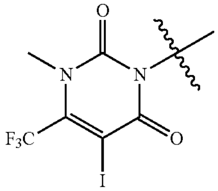, 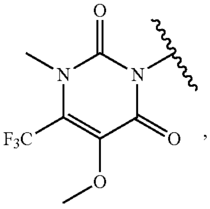,

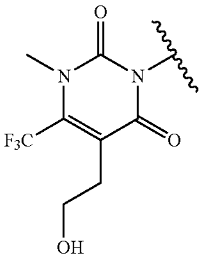, 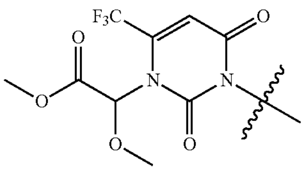 or

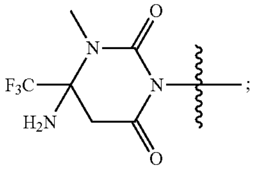;

Y represents halogen, halogenated C1-C6 alkyl or cyano;

Z represents halogen;

M represents CH or N;

X represents —$CX_1X_2$—(C1-C6 alkyl)$_n$-, —(C1-C6 alkyl)-$CX_1X_2$—(C1-C6 alkyl)$_n$— or —$(CH_2)$r-, n represents 0 or 1, r represents an integer greater than or equal to 2;

$X_1$ and $X_2$ independently represent hydrogen, halogen, C1-C6 alkyl, C2-C6 alkenyl, C2-C6 alkynyl, halogenated C1-C6 alkyl, halogenated C2-C6 alkenyl, halogenated C2-C6 alkynyl, C3-C6 cycloalkyl, C3-C6 cycloalkyl C1-C6 alkyl, C1-C6 alkoxy, C1-C6 alkylsulphanyl, hydroxy C1-C6 alkyl, C1-C6 alkoxy C1-C6 alkyl, phenyl or benzyl;

$X_3$ and $X_4$ independently represent O or S;

W represents hydroxyl, C1-C6 alkoxy, C2-C6 alkenyloxy, C2-C6 alkynyloxy, halogenated C1-C6 alkoxy, halogenated C2-C6 alkenyloxy, halogenated C2-C6 alkynyloxy, C3-C6 cycloalkyloxy, phenoxy, sulfydryl, C1-C6 alkylsulphanyl, C2-C6 alkenylsulphanyl, C2-C6 alkynylsulphanyl, halogenated C1-C6 alkylsulphanyl, halogenated C2-C6 alkenylsulphanyl, halogenated C2-C6 alkynylsulphanyl, C3-C6 cycloalkylsulphanyl, phenylsulphanyl, amino or C1-C6 alkylamino.

In another exemplary embodiment, the compound represented by the general formula I is selected from compound A: Q represents

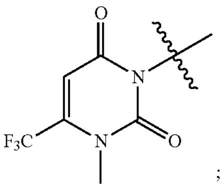;

Y represents chlorine; Z represents fluorine; M represents CH; X represents —C*$X_1X_2$—(C1-C6 alkyl)n-(C* is chiral center, R configuration), n represents 0; $X_1$ represents hydrogen; $X_2$ represents methyl; $X_3$ and $X_4$ independently represent O; W represents methoxy.

The PPO-inhibiting herbicides described above that are useful to carry out the present invention are often best applied in conjunction with one or more other herbicides to obtain control of a wider variety of undesirable vegetation. For example, PPO-inhibiting herbicides may further be used in conjunction with additional herbicides to which the crop plant is naturally tolerant, or to which it is resistant via expression of one or more additional transgenes as mentioned supra. When used in conjunction with other targeting herbicides, the presently claimed compounds can be formulated with the other herbicide or herbicides, tank mixed with the other herbicide or herbicides, or applied sequentially with the other herbicide or herbicides.

Suitable components for mixtures are, for example, selected from the herbicides of class b1) to b15):

b1) lipid biosynthesis inhibitors;

b2) acetolactate synthase inhibitors (ALS inhibitors);

b3) photosynthesis inhibitors;

b4) protoporphyrinogen-IX oxidase inhibitors, b5) bleacher herbicides;

b6) enolpyruvyl shikimate 3-phosphate synthase inhibitors (EPSP inhibitors);

b7) glutamine synthetase inhibitors;

b8) 7,8-dihydropteroate synthase inhibitors (DHP inhibitors);

b9) mitosis inhibitors;

b10) inhibitors of the synthesis of very long chain fatty acids (VLCFA inhibitors);

b11) cellulose biosynthesis inhibitors;

b12) decoupler herbicides;

b13) auxinic herbicides;

b14) auxin transport inhibitors; and b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M- isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS NO: 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters; including their agriculturally acceptable salts or derivatives.

Moreover, it may be useful to apply the PPO-inhibiting herbicides, when used in combination with other herbicidal compounds as described above, in combination with safeners. Safeners are chemical compounds which prevent or reduce damage on useful plants without having a major impact on the herbicidal action of herbicides towards unwanted plants. They can be applied either before sowings (e.g. on seed treatments, shoots or seedlings) or in the pre-emergence application or post-emergence application of the useful plant.

Furthermore, the safeners, the PPO-inhibiting herbicides and/or other herbicides can be applied simultaneously or in succession.

PPO-inhibiting herbicides, herbicidal compounds of groups b1)-b15) and safeners are known herbicides and safeners, respectively, for example, see WO2013/189984; The Compendium of Pesticide Common Names (http://www.alanwood.net/pesticides/); Farm Chemicals Handbook 2000, Volume 86, Meister Publishing Company, 2000; B. Hock, C. Fedtke, R. R. Schmidt, Herbizide [herbicide], Georg Thieme Verlag, Stuttgart, 1995; W. H. Ahrens, Herbicide Handbook, 7th edition, Weed Science Society of America, 1994, and K. K. Hatzios, Herbicide Handbook, supplement to the 7th edition, Weed Science Society of America, 1998.

The plant, to which the present invention is applied, is not particularly limited to, but includes monocotyledonous or dicotyledonous plants. Further, the plant includes herbaceous plants or woody plants. The monocotyledonous plant may include plants belonging to the family Alismataceae, Hydrocharitaceae, Juncaginaceae, Scheuchzeriaceae, Potamogetonaceae, Najadaceae, Zosteraceae, Liliaceae, Haemodoraceae, Agavaceae, Amaryllidaceae, Dioscoreaceae, Pontederiaceae, Iridaceae, Burmanniaceae, Juncaceae, Commelinaceae, Eriocaulaceae, Gramineae Poaceae, Araceae, Lemnaceae, Sparganiaceae, Typhaceae, Cyperaceae, Musaceae, Zingiberaceae, Cannaceae, Orchidaceae, but is not limited thereto.

The dicotyledonous plant may include plants belonging to the family Diapensiaceae, Clethraceae, Pyrolaceae, Ericaceae, Myrsinaceae, Primulaceae, Plumbaginaceae, Ebenaceae, Styracaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae, Umbelliferae (Apiaceae), but is not limited thereto.

In another exemplary embodiment, plants include but are not limited to: (1) food crops: *Oryza* spp., like *Oryza sativa, Oryza latifolia, Oryza sativa* L., *Oryza glaberrima; Triticum* spp., like *Triticum aestivum, T. Turgidum* ssp. *durum; Hordeum* spp., like *Hordeum vulgare, Hordeum arizonicum; Secale cereale; Avena* spp., like *Avena sativa, Avena fatua, Avena byzantine, Avena fatua* var. *sativa, Avena hybrida; Echinochloa* spp., like *Pennisetum glaucum, Sorghum* (*Sorghum bicolor*), *Sorghum vulgare, Triticale, Zea mays* or corn, Millet, Rice, Foxtail millet, Proso millet, *Sorghum bicolor, Panicum, Fagopyrum* spp., *Panicum miliaceum, Setaria italica, Zizania palustris, Eragrostis tef, Panicum miliaceum, Eleusine coracana*; (2) legume crops: *Glycine* spp. like *Glycine max, Vicia* spp., *Vigna* spp., *Pisum* spp., field bean, *Lupinus* spp., *Vicia, Tamarindus indica, Lens culinaris, Lathyrus* spp., *Lablab*, broad bean, mung bean, red bean, chickpea; (3) oil crops: *Arachis hypogaea, Arachis* spp, *Sesamum* spp., *Helianthus* spp. like *Helianthus annuus, Elaeis* like *Eiaeis guineensis* and *Elaeis oleifera*, rape, *Brassica napus, Sesamum orientale, Brassica juncea*, Oilseed rape, *Camellia oleifera*, oil palm, olive, castor-oil plant, *Brassica napus* L., *canola*; (4) fiber crops: *Agave sisalana, Gossypium* spp. like *Gossypium* and *Gossypium barbadense, Gossypium hirsutum, Hibiscus cannabinus, Agave sisalana, Musa textilis* Nee, *Linum usitatissimum, Corchorus capsularis* L, *Boehmeria nivea* (L.), *Cannabis sativa, Cannabis sativa*; (5) fruit crops: *Ziziphus* spp., *Cucumis* spp., *Passiflora edulis, Vitis* spp., *Vaccinium* spp., *Pyrus communis, Prunus* spp., *Psidium* spp., *Punica granatum, Malus* spp., *Citrullus lanatus, Citrus* spp., *Ficus carica, Fortunella* spp., *Fragaria* spp. (strawberry), *Crataegus* spp., *Diospyros* spp., *Eugenia unifora, Eriobotrya japonica, Dimocarpus longan, Carica papaya, Cocos* spp., *Averrhoa carambola, Actinidia* spp., *Prunus amygdalus, Musa* spp. (banana), *Persea* spp. (*Persea Americana*), *Psidium guajava, Mammea Americana, Mangifera indica, Canarium* album (*Olea europaea*), *Cocos nucifera, Malpighia emarginata, Manilkara zapota, Ananas comosus, Annona* spp., *Citrus reticulate* (*Citrus* spp.), *Artocarpus* spp., *Litchi chinensis, Ribes* spp., *Rubus* spp., pear, peach, apricot, plum, red bayberry, lemon, kumquat, durian, orange, blueberry, hami melon, muskmelon, date palm, walnut tree, cherry tree; (6) rhizome crops: *Manihot* spp., *Ipomoea batatas, Colocasia esculenta, tuber mustard, Allium cepa* (onion), *eleocharis tuberose* (water chestnut), *Cyperus rotundus, Rhizoma dioscoreae*; (7) vegetable crops: *Spinacia* spp., *Phaseolus* spp., *Lactuca sativa, Momordica* spp, *Petroselinum crispum, Capsicum* spp., *Solanum* spp. (such as *Solanum tuberosum, Solanum integrifolium, Solanum lycopersi-*

*cum*), *Lycopersicon* spp. (such as *Lycopersicon esculentum, Lycopersicon lycopersicum, Lycopersicon pyriforme*), *Macrotyloma* spp., Kale, *Luffa acutangula, lentil*, okra, onion, potato, artichoke, asparagus, broccoli, Brussels sprouts, cabbage, carrot, cauliflower, celery, collard greens, squash, *Benincasa hispida, Asparagus officinalis, Apium graveolens, Amaranthus* spp., *Allium* spp., *Abelmoschus* spp., *Cichorium endivia, Cucurbita* spp., *Coriandrum sativum, B. carinata, Rapbanus sativus, Brassica* spp. (such as *Brassica rapa* ssp., canola, turnip rape, leaf mustard, cabbage, black mustard, Brussels sprout, Solanaceae (eggplant), sweet pepper, cucumber, luffa, Chinese cabbage, rape, calabash, Chinese chives, lotus, lotus root, lettuce; (8) flower crops: *Tropaeolum minus, Tropaeolum majus, Canna indica, Opuntia* spp., *Tagetes* spp., *Cymbidium* (orchid), *Crinum asiaticum* L., *Clivia, Hippeastrum rutilum, Rosa rugosa, Rosa Chinensis, Jasminum sambac, Tulipa gesneriana* L., *Cerasus* sp. *Pharbitis nil* (L.) Choisy, *Calendula officinalis* L., *Nelumbo* sp., *Bellis perennis* L., *Dianthus caryophyllus, Petunia hybrida, Tulipa gesneriana* L., *Lilium brownii, Prunus mume, Narcissus tazetta* L., *Jasminum nudiflorum* Lindl., *Primula malacoides, Daphne odora, Camellia japonica, Michelia alba, Magnolia liliiflora, Viburnum macrocephalum, Clivia miniata, Malus spectabilis, Paeonia suffruticosa, Paeonia lactiflora, Syzygium aromaticum, Rhododendron simsii, Rhododendron hybridum, Michelia figo* (Lour.) Spreng., *Cercis chinensis, Kerria japonica, Weigela florida, Fructus forsythiae, Jasminum mesnyi, Parochetus communis, Cyclamen persicum* Mill., *Phalaenophsis hybrid, Dendrobium nobile, Hyacinthus orientalis, Iris tectorum Maxim, Zantedeschia aethiopica, Calendula officinalis, Hippeastrum rutilum, Begonia semperflorens* hybr, *Fuchsia hybrida, Begonia maculate Raddi, Geranium*; (9) medicinal crops: *Carthamus tinctorius, Mentha* spp., *Rheum rhabarbarum, Crocus sativus, Lycium chinense, Polygonatum odoratum, Polygonatum Kingianum, Anemarrhena asphodeloides* Bunge, *Radix ophiopogonis, Fritillaria cirrhosa, Curcuma aromatica, Amomum villosum* Lour., *Polygonum multiflorum, Rheum officinale, Glycyrrhiza uralensis* Fisch, *Astragalus membranaceus, Panax ginseng, Panax notoginseng, Acanthopanax gracilistylus, Angelica sinensis, Ligusticum wallichii, Bupleurum sinenses* DC., *Datura stramonium* Linn., *Datura metel* L., *Mentha haplocalyx, Leonurus sibiricus* L., *Agastache rugosus, Scutellaria baicalensis, Prunella vulgaris* L., *Pyrethrum carneum, Cinchona ledgeriana, Hevea brasiliensis* (wild), *Piper Nigrum* L.; (10) raw material crops: *Hevea brasiliensis, Ricinus communis, Vernicia fordii, Morus alba* L., Hops *Humulus lupulus, Betula, Alnus cremastogyne* Burk., *Rhus verniciflua* stokes; (11) pasture crops: *Agropyron* spp., *Trifolium* spp., *Miscanthus sinensis, Pennisetum* sp., *Phalaris arundinacea, Panicum virgatum*, prairie grasses, Indiangrass, Big bluestem grass, *Phleum pratense*, turf, *cyperaceae* (*Kobresia pygmaea, Carex pediformis, Carex humilis*), *Medicago sativa* Linn, *Phleum pratense* L., *Medicago sativa, Melilotus suavcolen, Astragalus sinicus, Crotalaria juncea, Sesbania cannabina, Azolla imbircata, Eichhornia crassipes, Amorpha fruticosa, Lupinus micranthus, Trifolium, Astragalus adsurgens* pall, *Pistia stratiotes* linn, *Alternanthera philoxeroides, Lolium*; (12) sugar crops: *Saccharum officinarum* (*Saccharum* spp.), *Beta vulgaris*; (13) beverage crops: *Camellia sinensis, Camellia Sinensis, tea, Coffee* (*Coffea* spp.), *Theobroma cacao, Humulus lupulus* Linn.; (14) lawn plants: *Ammophila arenaria, Poa* spp. (*Poa pratensis* (bluegrass)), *Agrostis* spp. (*Agrostis matsumurae, Agrostis palustris*), *Lolium* spp. (*Lolium*), *Festuca* spp. (*Festuca ovina* L.), *Zoysia* spp. (*Zoysia japonica*), *Cynodon* spp. (*Cynodon dactylon*/Bermuda grass), *Stenotaphrum secunda* tum (*Stenotaphrum secunda* tum), *Paspalum* spp. (*Paspalum notatum*), *Eremochloa ophiuroides* (centipede grass), *Axonopus* spp. (carpetweed), *Bouteloua dactyloides* (buffalo grass), *Bouteloua* var. spp. (*Bouteloua gracilis*), *Digitaria sanguinalis, Cyperus rotundus, Kyllinga brevifolia, Cyperus amuricus, Erigeron canadensis, Hydrocotyle sibthorpioides, Kummerowia striata, Euphorbia humifusa, Viola arvensis, Carex rigescens, Carex heterostachya*, turf; (15) tree crops: *Pinus* spp., *Salix* spp., *Acer* spp., *Hibiscus* spp., *Eucalyptus* spp., *Ginkgo biloba, Bambusa* sp., *Populus* spp., *Prosopis* spp., *Quercus* spp., *Phoenix* spp., *Fagus* spp., *Ceiba pentandra, Cinnamomum* spp., *Corchorus* spp., *Phragmites australis, Physalis* spp., *Desmodium* spp., *Populus, Hedera helix, Populus tomentosa* Carr, *Viburnum odoratissinum, Ginkgo biloba* L., *Quercus, Ailanthus altissima, Schima superba, Ilex* purpurea, *Platanus acerifolia, ligustrum lucidum, Buxus megistophylla* Levl., *Dahurian larch, Acacia mearnsii, Pinus massoniana, Pinus khasys, Pinus yunnanensis, Pinus finlaysoniana, Pinus tabuliformis, Pinus koraiensis, Juglans nigra, Citrus limon, Platanus acerifolia, Syzygium jambos, Davidia involucrate, Bombax malabarica* L., *Ceiba pentandra* (L.), *Bauhinia blakeana, Albizia saman, Albizzia julibrissin, Erythrina corallodendron, Erythrina indica, Magnolia gradiflora, Cycas revolute, Lagerstroemia indica*, coniferous, macrophanerophytes, *Frutex, Morus alba* L.; (16) nut crops: *Bertholletia excelsea, Castanea* spp., *Corylus* spp., *Carya* spp., *Juglans* spp., *Pistacia vera, Anacardium occidentale, Macadamia* (*Macadamia integrifolia*), *Carya illinoensis* Koch, *Macadamia*, Pistachio, Badam, other plants that produce nuts; (17) others: *Arabidopsis thaliana, Brachiaria eruciformis, Cenchrus echinatus, Setaria faberi, Eleusine indica, Cadaba farinose, algae, Carex elata*, ornamental plants, *Carissa macrocarpa, Cynara* spp., *Daucus carota, Dioscorea* spp., *Erianthus* sp., *Festuca arundinacea, Hemerocallis fulva, Lotus* spp., *Luzula sylvatica, Medicago sativa, Melilotus* spp., *Morus nigra, Nicotiana* spp., *Olea* spp., *Ornithopus* spp., *Pastinaca sativa, Sambucus* spp., *Sinapis* sp., *Syzygium* spp., *Tripsacum dactyloides, Triticosecale rimpaui, Viola odorata*, and the like.

In one exemplary embodiment, the plant is rice (*Oryza sativa* L.), *sorghum* (*Sorghum bicolor*), wheat (*Triticum aestivum*), barley (*Hordeum vulgare*), foxtail millet (*Setaria italica*), corn (*Zea mays*), sugarcane (*Saccharum officinarum*), *Arabidopsis thaliana*, soybean (*Glycine max*), peanut (*Arachis hypogaea*), tobacco (*Nicotiana tabacum*), cotton (*Gossypium hirsutum*), radish (*Raphanus sativus*), cabbage (*Brassica oleracea*), sweet potato (*Dioscorea esculenta*), yam (*Dioscorea cayenensis*), cassava (*Manihot esculenta*), potato (*Solanum tuberosum*), tomato (*Solanum lycopersicum*), pepper (*Capsicum annuum*), eggplant (*Solanum melongena*), watermelon (*Citrullus lanatus*), squash (*Cucurbita moschata*), cucumber (*Cucumis sativus*), lettuce (*Lactuca sativa*), sesame (*Sesamum indicum*), oilseed rape (*Brassica napus*), sunflower (*Helianthus annuus*), mulberry (*Morus alba*), cowpea (*Vigna unguiculata*), strawberry (*Fragaria ananassa*), apple (*Malus domestica*), peach (*Prunus persica*), cherry (*Prunus pseudocerasus*), apricot (*Prunus armeniaca*), grape vine (*Vitis vinfera*), *papaya* (*Carica papaya*) or alfalfa (*Medicago sativa*).

In the present invention, the term "plant tissue" or "plant part" includes plant cells, protoplasts, plant tissue cultures, plant callus, plant blocks, and plant embryos, pollens, ovules, seeds, leaves, stems, flowers, branches, seedlings, fruits, cores, spikes, roots, root tips, anthers, etc.

In the present invention, the "plant cell" should be understood to mean any cell derived from or found in a plant that is capable of forming, for example, an undifferentiated tissue such as callus, a differentiated tissue such as an embryo, a plant part, a plant or a seed.

In the present invention, the "host organism" should be understood to mean any single or multicellular organism into which a nucleic acid encoding a mutant protein can be introduced, including, for example, bacteria such as *Eescherichia coli*, fungi such as yeast (e.g., *Saccharomyces cerevisiae*), molds (e.g., *aspergillus*), plant cells, plants and the like.

In one aspect, the present invention discloses a PPO polypeptide or a bioactive fragment thereof tolerant to a PPO-inhibiting herbicide, and the polypeptide comprises the motif "LLLNYI" (namely "leucine-leucine-leucine-aspartyl-tyrosine-isoleucine") wherein the leucine L at position 3 within the motif is substituted with any other amino acid, or the tyrosine Y at position 5 is substituted with any other amino acid.

In one embodiment, within the motif "LLLNYI", the leucine L at position 3 is mutated to serine S, abbreviated as "LLSNYI"; or
- the leucine L at position 3 is mutated to isoleucine I, abbreviated as "LLINYI"; or
- the leucine L at position 3 is mutated to glycine G, abbreviated as "LLGNYI"; or
- the leucine L at position 3 is mutated to threonine T, abbreviated as "LLTNYI"; or
- the leucine L at position 3 is mutated to valine V, abbreviated as "LLVNYI"; or
- the leucine L at position 3 is mutated to tryptophan W, abbreviated as "LLWNYI"; or
- the tyrosine Y at position 5 is mutated to methionine M, abbreviated as "LLLNMI"; or
- the tyrosine Y at position 5 is mutated to isoleucine I, abbreviated as "LLLNII"; or
- the tyrosine Y at position 5 is mutated to leucine L, abbreviated as "LLLNLI"; or
- the tyrosine Y at position 5 is mutated to valine V, abbreviated as "LLLNVI".

In another embodiment, within the motif "LLLNYI", the leucine L at position 3 is substituted with any other amino acid and the tyrosine Y at position 5 is substituted with any other amino acid.

In another embodiment, within the motif "LLLNYI", the leucine L at position 3 is mutated to serine S and the tyrosine Y at position 5 is mutated to isoleucine I, abbreviated as "LLSNII"; or
- the leucine L at position 3 is mutated to threonine T and the tyrosine Y at position 5 is mutated to isoleucine I, abbreviated as "LLTNII"; or
- the leucine L at position 3 is mutated to threonine T and the tyrosine Y at position 5 is mutated to valine V, abbreviated as "LLTNVI"; or
- the leucine L at position 3 is mutated to serine S and the tyrosine Y at position 5 is mutated to valine V, abbreviated as "LLSNVI"; or
- the leucine L at position 3 is mutated to valine V and the tyrosine Y at position 5 is mutated to leucine L, abbreviated as "LLVNLI"; or
- the leucine L at position 3 is mutated to tryptophan W and the tyrosine Y at position 5 is mutated to leucine L, abbreviated as "LLWNLI".

In one embodiment, the polypeptide comprises the mutant of freely-combined amino acid sequence and a fragment thereof that has at least 60%, at least 65%, at least 70%, at least 75%, at least 80%, at least 85%, at least 90%, at least 95%, at least 96%, at least 97%, at least 98% or at least 99% sequence identity to the amino acid sequence as set forth in any one from SEQ ID NO: 1-19, and the mutant comprises one or more amino acid mutations as defined above.

In another embodiment, the polypeptide has amino acid sequence as set forth in any one from SEQ ID NO: 1-19, except that it has one or more amino acid mutations as defined above; preferably, the amino acid sequence of the polypeptide is as set forth in any one from SEQ ID NO: 1-19, except for one or more amino acid mutations as defined above.

In another embodiment, as compared to the amino acid sequence of a wild-type rice PPO1, the amino acid sequence of the PPO polypeptide has one or more mutations at one or more positions (only) corresponding to 423 and 425 of the amino acid sequence of wild-type rice PPO1 protein as set forth in SEQ ID NO: 1; or
- as compared to the amino acid sequence of a wild-type corn PPO1, the amino acid sequence of the PPO polypeptide has one or more mutations at one or more positions (only) corresponding to 424 and 426 of the amino acid sequence of wild-type corn PPO1 protein as set forth in SEQ ID NO: 2; or
- as compared to the amino acid sequence of a wild-type oilseed rape PPO1, the amino acid sequence of the PPO polypeptide has one or more mutations at one or more positions (only) corresponding to 424 and 426 of the amino acid sequence of wild-type oilseed rape PPO1 protein as set forth in SEQ ID NO: 3; or
- as compared to the amino acid sequence of a wild-type oilseed rape PPO1, the amino acid sequence of the PPO polypeptide has one or more mutations at one or more positions (only) corresponding to 423 and 425 of the amino acid sequence of wild-type oilseed rape PPO1 protein as set forth in SEQ ID NO: 4; or
- as compared to the amino acid sequence of a wild-type peanut PPO1, the amino acid sequence of the PPO polypeptide has one or more mutations at one or more positions (only) corresponding to 445 and 447 of the amino acid sequence of wild-type peanut PPO1 protein as set forth in SEQ ID NO: 5; or
- as compared to the amino acid sequence of a wild-type peanut PPO1, the amino acid sequence of the PPO polypeptide has one or more mutations at one or more positions (only) corresponding to 439 and 441 of the amino acid sequence of wild-type peanut PPO1 protein as set forth in SEQ ID NO: 6; or
- as compared to the amino acid sequence of a wild-type soybean PPO1, the amino acid sequence of the PPO polypeptide has one or more mutations at one or more positions (only) corresponding to 430 and 432 of the amino acid sequence of wild-type soybean PPO1 protein as set forth in SEQ ID NO: 7; or
- as compared to the amino acid sequence of a wild-type *sorghum* PPO1, the amino acid sequence of the PPO polypeptide has one or more mutations at one or more positions (only) corresponding to 423 and 425 of the amino acid sequence of wild-type *sorghum* PPO1 protein as set forth in SEQ ID NO: 8; or
- as compared to the amino acid sequence of a wild-type wheat PPO1, the amino acid sequence of the PPO polypeptide has one or more mutations at one or more positions (only) corresponding to 418 and 420 of the amino acid sequence of wild-type wheat PPO1 protein as set forth in SEQ ID NO: 9, 10 or 11; or as compared to the amino acid sequence of a wild-type tomato PPO1, the amino acid sequence of the PPO polypeptide has one or more mutations at one or more positions (only) corresponding to 445 and 447 of the amino acid sequence of wild-type tomato PPO1 protein as set forth in SEQ ID NO: 12; or as compared to the amino acid sequence of a wild-type potato PPO1, the amino acid sequence of the PPO polypeptide has one or more mutations at one or more positions (only) corresponding to 444 and 446 of the amino acid sequence of wild-type potato PPO1 protein as set forth in SEQ ID NO: 13; or as compared to the amino acid sequence of a wild-type tobacco PPO1, the amino acid sequence of the PPO polypeptide has one or more mutations at one or more positions (only) corresponding to 440 and 442 of the amino acid sequence of wild-type tobacco PPO1 protein as set forth in SEQ ID NO: 14; or as compared to the amino acid sequence of a wild-type *Arabidopsis thaliana* PPO1, the amino acid sequence of the PPO polypeptide has one or more mutations at one or more positions (only) corresponding to 423 and 425 of the amino acid sequence of wild-type *Arabidopsis thaliana* PPO1 protein as set forth in SEQ ID NO: 15; or as compared to the amino acid sequence of a wild-type upland cotton PPO1, the amino acid sequence of the PPO polypeptide has one or more mutations at one or more positions (only) corresponding to 426 and 428 of the amino acid sequence of wild-type upland cotton PPO1 protein as set forth in SEQ ID NO: 16; or as compared to the amino acid sequence of a wild-type radish PPO1, the amino acid sequence of the PPO polypeptide has one or more mutations at one or more positions (only) corresponding to 425 and 427 of the amino acid sequence of wild-type radish PPO1 protein as set forth in SEQ ID NO: 17; or as compared to the amino acid sequence of a wild-type foxtail millet PPO1, the amino acid sequence of the PPO polypeptide has one or more mutations at one or more positions (only) corresponding to 422 and 424 of the amino acid sequence of wild-type foxtail millet PPO1 protein as set forth in SEQ ID NO: 18; or as compared to the amino acid sequence of a wild-type cabbage PPO1, the amino acid sequence of the PPO polypeptide has one or more mutations at one or more positions (only) corresponding to 424 and 426 of the amino acid sequence of wild-type cabbage PPO1 protein as set forth in SEQ ID NO: 19.

In another embodiment, as compared to the amino acid sequence of a wild-type rice PPO1, the amino acid sequence of the PPO polypeptide has one or more mutations selected from the group consisting of L423S, L423I, L423G, Y425M, Y425I and Y425V at one or more positions (only) corresponding to 423 and 425 of the amino acid sequence of wild-type rice PPO1 protein as set forth in SEQ ID NO: 1; preferably, it has the following mutations: L423S/Y425I; or as compared to the amino acid sequence of a wild-type corn PPO1, the amino acid sequence of the PPO polypeptide has one or more mutations selected from the group consisting of L424T, L424S, L424V, Y424W, Y426V, Y426I and Y426 L at one or more positions (only) corresponding to 424 and 426 of the amino acid sequence of wild-type corn PPO1 protein as set forth in SEQ ID NO: 2; preferably, it has the following mutations: L424T/Y426V, L424S/Y426V, L424V/Y426L, L424W/Y426 L or L424S/Y426I; or as compared to the amino acid sequence of a wild-type oilseed rape PPO1, the amino acid sequence of the PPO polypeptide has one or more mutations selected from the group consisting of L424S and Y426I at one or more positions (only) corresponding to 424 and 426 of the amino acid sequence of wild-type oilseed rape PPO1 protein as set forth in SEQ ID NO: 3; preferably, it has the following mutations: L424S/Y426I; or as compared to the amino acid sequence of a wild-type oilseed rape PPO1, the amino acid sequence of the PPO polypeptide has one or more mutations selected from the group consisting of L423S and Y425I at one or more positions (only) corresponding to 423 and 425 of the amino acid sequence of wild-type oilseed rape PPO1 protein as set forth in SEQ ID NO: 4; preferably, it has the following mutations: L423S/Y425I; or as compared to the amino acid sequence of a wild-type peanut PPO1, the amino acid sequence of the PPO polypeptide has one or more mutations selected from the group consisting of L445S and Y447I at one or more positions (only) corresponding to 445 and 447 of the amino acid sequence of wild-type peanut PPO1 protein as set forth in SEQ ID NO: 5; preferably, it has the following mutations: L445S/Y447I; or as compared to the amino acid sequence of a wild-type peanut PPO1, the amino acid sequence of the PPO polypeptide has one or more mutations selected from the group consisting of L439S and Y441I at one or more positions (only) corresponding to 439 and 441 of the amino acid sequence of wild-type peanut PPO1 protein as set forth in SEQ ID NO: 6; preferably, it has the following mutations: L439S/Y441I; or as compared to the amino acid sequence of a wild-type soybean PPO1, the amino acid sequence of the PPO polypeptide has one or more mutations selected from the group consisting of L430S and Y432I at one or more positions (only) corresponding to 430 and 432 of the amino acid sequence of wild-type soybean PPO1 protein as set forth in SEQ ID NO: 7; preferably, it has the following mutations: L430S/Y432I; or as compared to the amino acid sequence of a wild-type *sorghum* PPO1, the amino acid sequence of the PPO polypeptide has one or more mutations selected from the group consisting of L423S and Y425I at one or more positions (only) corresponding to 423 and 425 of the amino acid sequence of wild-type *sorghum* PPO1 protein as set forth in SEQ ID NO: 8; preferably, it has the following mutations: L423S/Y425I; or as compared to the amino acid sequence of a wild-type wheat PPO1, the amino acid sequence of the PPO polypeptide has one or more mutations selected from the group consisting of L418S and Y420I at one or more positions (only) corresponding to 418 and 420 of the amino acid sequence of wild-type wheat PPO1 protein as set forth in SEQ ID NO: 9, 10 or 11; preferably, it has the following mutations: L418S/Y420I; or as compared to the amino acid sequence of a wild-type tomato PPO1, the amino acid sequence of the PPO polypeptide has one or more mutations selected from the group consisting of L445S and Y447I at one or more positions (only) corresponding to 445 and 447 of the amino acid sequence of wild-type tomato PPO1 protein as set forth in SEQ ID NO: 12; preferably, it has the following mutations: L445S/Y447I; or as compared to the amino acid sequence of a wild-type potato PPO1, the amino acid sequence of the PPO polypeptide has one or more mutations selected from the group consisting of L444S and Y446I at one or more positions (only) corresponding to 444 and 446 of the amino acid sequence of wild-type potato PPO1 protein as set forth in SEQ ID NO: 13; preferably, it has the following mutations: L444S/Y446I; or as compared to the amino acid sequence of a wild-type tobacco PPO1, the amino acid sequence of the PPO polypeptide has one or more mutations selected from the group consisting of L440S and Y442I at one or more positions (only) corresponding to 440 and 442 of the amino acid sequence of wild-type tobacco PPO1 protein as set forth in SEQ ID NO: 14; preferably, it has the following mutations: L440S/Y442I; or as compared to the amino acid sequence of a wild-type *Arabidopsis thaliana* PPO1, the amino acid sequence of the PPO polypeptide has one or more mutations selected from the group consisting of L423S and Y425I at one or more positions (only) corresponding to 423 and 425 of the amino acid sequence of wild-type *Arabidopsis thaliana* PPO1 protein as set forth in SEQ ID NO: 15; preferably, it has the following mutations: L423S/Y425I; or as compared to the amino acid sequence of a wild-type upland cotton PPO1, the amino acid sequence of the PPO polypeptide has one or more mutations selected from the group consisting of L426S and Y428I at one or more positions (only) corresponding to 426 and 428 of the amino acid sequence of wild-type upland cotton PPO1 protein as set forth in SEQ ID NO: 16; preferably, it has the following mutations: L426S/Y428I; or as compared to the amino acid sequence of a wild-type radish PPO1, the amino acid sequence of the PPO polypeptide has one or more mutations selected from the group consisting of L425S and Y427I at one or more positions (only) corresponding to 425 and 427 of the amino acid sequence of wild-type radish PPO1 protein as set forth in SEQ ID NO: 17; preferably, it has the following mutations: L425S/Y427I; or as compared to the amino acid sequence of a wild-type foxtail millet PPO1, the amino acid sequence of the PPO polypeptide has one or more mutations selected from the group consisting of L422S and Y424I at one or more positions (only) corresponding to 422 and 424 of the amino acid sequence of wild-type foxtail millet PPO1 protein as set forth in SEQ ID NO: 18; preferably, it has the following mutations: L422S/Y424I; or as compared to the amino acid sequence of a wild-type cabbage PPO1, the amino acid sequence of the PPO polypeptide has one or more mutations selected from the group consisting of L424S and Y426I at one or more positions (only) corresponding to 424 and 426 of the amino acid sequence of wild-type cabbage PPO1 protein as set forth in SEQ ID NO: 19; preferably, it has the following mutations: L424S/Y426I.

In another embodiment, the polypeptide has an amino acid sequence as set forth in any one from SEQ ID NO: 20-48; preferably, the amino acid sequence of the polypeptide is as set forth in any one from SEQ ID NO: 20-48.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

The terms "protein", "polypeptide" and "peptide" can be used interchangeably in the present invention and refer to a polymer of amino acid residues, including polymers of chemical analogs in which one or more amino acid residues are natural amino acid residues. The proteins and polypeptides of the present invention may be recombinantly produced or chemically synthesized.

For the terms regarding amino acid substitutions used in the specification, the first letter represents a naturally occurring amino acid at a certain position in a particular sequence, the following number represents the position corresponding to the SEQ ID NO: 1, and the second letter represents a different amino acid substituting for the naturally occurring amino acid. For example, L423S represents that the leucine at position 423 is substituted with serine relative to the amino acid sequence of SEQ ID NO: 1. For double or multiple mutations, each mutation is separated by "/". For example, L423S/Y425I means that, relative to the amino acid sequence of SEQ ID NO: 1, the leucine at position 423 is substituted with serine, and the tyrosine at position 425 is substituted with isoleucine, and both mutations are present in the specific mutant OsPPO1 protein.

A particular amino acid position (numbering) within the protein of the present invention is determined by aligning the amino acid sequence of a protein of interest with SEQ ID NO: 1 or SEQ ID NO: 2-19, etc. using a standard sequence alignment tool, for example, Smith-Waterman algorithm or CLUSTALW2 algorithm is used to align two sequences, wherein the sequences are considered to be aligned when the alignment score is the highest. The alignment score can be calculated according to the method described in Wilbur, W. J. and Lipman, D. J. (1983), "Rapid similarity searches of nucleic acid and protein data banks", Proc. Natl. Acad. Sci. USA, 80: 726-730. The default parameters used in the ClustalW2 (1.82) algorithm are preferably: protein gap opening penalty=10.0; protein gap extension penalty=0.2; protein matrix=Gonnet; protein/DNA end gap=−1; and protein/DNA GAPDIST=4.

Preferably, the AlignX program (a part of the vector NTI set) is used to match the default parameters for the multiple alignment (gap opening penalty: 10 og, gap extension penalty: 0.05), and the position of a particular amino acid within a protein of the present invention is determined by aligning the amino acid sequence of the protein with SEQ ID NO: 1.

The identity of amino acid sequences can be determined by conventional methods using the BLAST algorithm (Altschul et al., 1990, Mol. Biol. 215:403-10) available from the National Center for Biotechnology Information (www.ncbi.nlm.nih.gov/) with the default parameters.

It will also be apparent for a person skilled in the art that the structure of a protein can be altered, without adversely affecting its activity and functionality, for example, one or more conservative amino acid substitutions can be introduced into the amino acid sequence of the protein without adversely affecting the activity and/or three-dimensional configuration of the protein molecule. A person skilled in the art knows examples and embodiments of conservative amino acid substitutions. Specifically, an amino acid residue at certain site may be substituted with another amino acid residue belonging to the same group as the amino acid to be substituted, that is, a non-polar amino acid residue is substituted with another non-polar amino acid residue, a polar uncharged amino acid residue is substituted with another polar uncharged amino acid residue, a basic amino acid residue is substituted with another basic amino acid residue, and an acidic amino acid residue is substituted with an acidic amino acid residue. As long as a substitution does not impair the biological activity of the protein, such a conservative substitution that one amino acid is substituted by other amino acid which belong to the same group falls within the scope of the present invention.

Accordingly, the mutant protein of the present invention may further contain one or more other mutations such as conservative substitutions in the amino acid sequence in addition to the above mutations. In addition, the invention also encompasses mutant proteins that further contain one or more other non-conservative substitutions, so long as the non-conservative substitutions do not significantly affect the desired function and biological activity of the protein of the present invention.

As is well known in the art, one or more amino acid residues can be deleted from the N- and/or C-terminus of a protein, and the protein still retains the function and activity. Accordingly, in another aspect, the present invention also relates to fragments which lack one or more amino acid residues at the N- and/or C-terminus of a mutant protein while retaining the desired function and activity. Within the scope of the invention, and the fragments are referred to as bioactive fragments. In the present invention, the "bioactive fragment" refers to a portion of a mutant protein of the present invention which retains the biological activity of the mutant protein of the present invention. For example, a bioactive fragment of a mutant protein may be a bioactive fragment that lacks a moiety of one or more (for example, 1-50, 1-25, 1-10 or 1-5, e.g., 1, 2, 3, 4 or 5) of amino acid residues at the N- and/or C-terminus of the protein, but still retains the desired biological activity of the full-length protein.

As used herein, the term "mutation" refers to a single amino acid variation in a polypeptide and/or at least a single nucleotide variation in a nucleic acid sequence relative to the normal sequence or wild-type sequence or a reference sequence. In some embodiments a mutation refers to a single amino acid variation in a polypeptide and/or at least a single nucleotide variation in a nucleic acid sequence relative to a nucleotide or amino acid sequence of a PPO protein that is not herbicide resistant. In certain embodiments, mutation refers to having one or more mutations at the amino acid location corresponding to the reference PPO amino acid sequence, for example, as set forth in any one from SEQ ID NO: 1-19 or at the homologous location of a homologous gene from a different species. In certain embodiments, a mutation may include a substitution, a deletion, an inversion or an insertion. In some embodiments, a substitution, deletion, insertion, or inversion may include a variation at 1, 2, 3, 4, 5, 6, 7, 8, 9, 10, 11, 12, 13, 14, 15, 16, 17, 18, 19, 20, 21, 22, 23 or 24 nucleotides. In some embodiments, a substitution, deletion, insertion, or inversion may include a variation at 1, 2, 3, 4, 5, 6, 7 or 8 amino acid positions.

The term "wild type" is relative to mutation, which refers to the phenotype with the highest frequency in a specific population, or a system, organism and gene that has this phenotype. In some instances, a wild-type allele refers to the standard allele at a locus, or the allele having the highest frequency in a particular population, and may be represented by a particular amino acid or nucleic acid sequence. For example, a wild-type rice PPO protein may be represented by SEQ ID NO: 1. For example, a wild-type corn PPO protein may be represented by SEQ ID NO: 2.

In another aspect, the present invention also provides an isolated polynucleotide comprising a nucleic acid sequence selected from the group consisting of:

(1) a nucleic acid sequence encoding the PPO polypeptide or a biologically active fragment thereof, or a partial sequence thereof, or a complementary sequence thereof, (2) a nucleic acid sequence that hybridizes to the sequence shown in (1) under stringent conditions; and (3) a nucleic acid sequence encoding the same amino acid sequence as the sequence shown in (1) due to degeneracy of genetic code, or a complementary sequence thereof.

In one embodiment, the polynucleotide is a DNA molecule.

The terms "polynucleotide", "nucleic acid", "nucleic acid molecule" or "nucleic acid sequence" are used interchangeably to refer to an oligonucleotide, nucleotide or polynucleotide, and fragments or portions thereof, which may be single or double stranded, and represent the sense or antisense strand. A nucleic acid may include DNA, RNA or hybrids thereof, and may be of natural or synthetic origin. For example, a nucleic acid may include mRNA or cDNA. Nucleic acid may include nucleic acid that has been amplified {e.g., using polymerase chain reaction}. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymine (uracil if RNA); "M" means adenine or cytosine; "K" means guanine or thymine; and "W" means adenine or thymine. The term "isolated", when referring to a nucleic acid refers to a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

It will be apparent for a person skilled in the art that a variety of different nucleic acid sequences can encode the amino acid sequences disclosed herein due to the degeneracy of genetic codes. A person skilled in the art is able to generate additional nucleic acid sequences encoding a same protein, and thus the present invention encompasses nucleic acid sequences encoding the same amino acid sequence due to the degeneracy of genetic codes. For example, in order to achieve high expression of a heterologous gene in a host organism, such as a plant, the gene can be optimized using host-preferred codons for better expression.

The present invention also provides a plant genome comprising the polynucleotide.

In one embodiment, the plant genome is modified with at least one mutation. In another embodiment, the plant genome is modified with at least two mutations.

In one embodiment, the plastid PPO gene is modified by the plant genome mutation, such as rice plastid OsPPO1. In another embodiment, the plastid PPO gene allele is modified by the plant genome mutation, such as BnPPO1-C5 or BnPPO1-A10.

The present invention also provides a vector construct comprising the polynucleotide and the homologous or non-homologous promoter operably linked thereto.

The present invention also provides a host cell comprising the polynucleotide or the vector construct.

In one embodiment, the host cell is a plant cell.

The present invention also provides a producing method of a plant cell to gain or improve its tolerance to a PPO-inhibiting herbicide, comprising producing the above polynucleotide or the above vector construct in the plant cell by using gene editing method, or introducing the above polynucleotide or the above vector construct into the plant cell by using transgenic method.

The present invention also provides a producing method of a plant to gain or improve its tolerance to a PPO-inhibiting herbicide, comprising regenerating the above plant cell or a plant cell produced by the above method.

The present invention also provides a plant produced by the above method.

In one embodiment, the above plant or plant cell is non-transgenic.

In another embodiment, the above plant or plant cell is transgenic.

The term "transgenic" plant refers to a plant that comprises a heterologous polynucleotide. Preferably, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been so altered by the presence of heterologous nucleic acid including those transgenic organisms or cells initially so altered, as well as those created by crosses or asexual propagation from the initial transgenic organism or cell. The term "transgenic" as used herein is not intended to encompass the alteration of the genome (chromosomal or extra-chromosomal) by conventional plant breeding methods (e.g., crosses) or by naturally occurring events such as, e.g., self-fertilization, random cross-fertilization, non-recombinant viral infection, non-recombinant bacterial transformation, non-recombinant transposition, or spontaneous mutation.

The terms "gene-edited plant", "gene-edited plant part" or "gene-edited plant cell" refer to a plant, plant part or plant cell thereof comprising one or more endogenous genes edited through a gene-editing system. The term "gene editing system" refers to a protein, nucleic acid, or combination thereof that is capable of modifying a target locus of an endogenous DNA sequence when introduced into a cell. Numerous gene editing systems suitable for use in the methods of the present invention are known in the art including, but not limited to, zinc-finger nuclease systems (ZFNs), transcription activator-like effector nuclease systems (TALEN), and CRISPR/Cas systems. The term "gene editing" as used in the present invention usually refers to a technique by which DNA is inserted, deleted, modified or replaced in a genome. For example, the gene editing may include a knock-in method which may be a common operating method used by a person skilled in the art. See "Gene Target: A Practical Method" (Edited by Joyner, Oxford University Press, 2000) by reference.

The present invention also provides a method of enabling a plant to gain or improve tolerance to a PPO-inhibiting herbicide, comprising introducing a modification in the gene encoding a protein with PPO activity to produce the PPO polypeptide or a bioactive fragment thereof.

The present invention also provides a method of gaining or improving the tolerance of a plant cell, plant tissue, plant part or plant to a PPO-inhibiting herbicide, comprising expressing the PPO polypeptide or a bioactive fragment thereof in the plant cell, plant tissue, plant part or plant;

or, comprising hybridizing a plant expressing the PPO polypeptide or a bioactive fragment thereof with another plant, and screening of a plant or a part thereof capable of gaining or improving the tolerance to a PPO-inhibiting herbicide;

or, comprising gene editing a protein with PPO activity of the plant cell, plant tissue, plant part or plant to achieve expression of the PPO polypeptide or a bioactive fragment thereof.

The present invention also provides use of the PPO polypeptide or a bioactive fragment thereof or the polynucleotide for gaining or improving tolerance of a host cell, plant cell, plant issue, plant part or plant to a PPO-inhibiting herbicide.

In one embodiment, the host cell is a bacterial cell or a fungal cell.

The herbicide-resistant PPO protein may be obtained from a natural source by extraction and purification using methods widely known in the art. Alternatively, it may be obtained as a synthetic protein prepared by chemical synthesis, or as a recombinant protein prepared by a genetic recombination technology. When chemically synthesized, the protein may be obtained by a polypeptide synthesis method widely known in the art. When the genetic recombination technology is used, the nucleic acid encoding the herbicide-resistant PPO protein is inserted into a proper expression vector, this vector is transformed into a host cell, the host cell is cultured to express the desired protein, and then the herbicide-resistant PPO protein is recovered from the host cell. After the protein is expressed in a selected host cell, general biochemical separation techniques, for example, treatment with a protein precipitating agent (salting out), centrifugation, ultrasonic disruption, ultrafiltration, dialysis, chromatography such as molecular sieve chromatography (gel filtration), adsorption chromatography, ion exchange chromatography, affinity chromatography and the like may be used for the isolation and purification thereof. Generally, in order to separate the protein with a high purity, these methods may be used in combination.

The herbicide-resistant PPO nucleic acid molecule may be isolated or prepared using standard molecular biological techniques, for example, a chemical synthesis or recombination method. Alternatively, commercially available one may be used.

The PPO protein provided herein may be introduced into a plant, thereby being used for enhancement of the herbicide resistance of the plant.

The herbicide-resistant PPO gene provided herein may be introduced into the plant by various methods known in the art, and can be transgenic or gene-edited by using an expression vector for plant transformation.

An appropriate promoter which may be included in the vector may be any promoter generally used in the art for plant transgenic or gene editing. For example, the promoter commonly used in plant transgenic or gene editing may include an SP6 promoter, a T7 promoter, a T3 promoter, a PM promoter, a corn ubiquitin promoter, a cauliflower mosaic virus (CaMV) 35S promoter, a nopaline synthase (nos) promoter, a figwort mosaic virus 35S promoter, a sugarcane bacilliform virus promoter, a commelina yellow mottle virus promoter, a light-inducible promoter from the small subunit of ribulose-1,5-bisphosphate carboxylase (ssRUBISCO), a rice cytosolic triosephosphate isomerase (TPI) promoter, an adenine phosphoribosyltransferae (APRT) promoter of *Arabidopsis*, an octopine synthase promoter, and a BCB (blue copper binding protein) promoter, but is not limited thereto.

Plant transgenic or gene editing vectors include a polyadenylation signal sequence causing polyadenylation of 3-terminus, and for example, it may include NOS 3'-end derived from a nopaline synthase gene of *Agrobacterium tumefaciens*, an octopine synthase 3'-end derived from an octopine synthase gene of *Agrobacterium tumefaciens*, 3'-end of protease inhibitor I or II gene of tomato or potato, a CaMVPoly A signal sequence, 3'-end of a rice α-amylase gene and 3'-end of a phaseolin gene, but is not limited thereto.

In the above-mentioned transgenic vector, a transit peptide required for targeting to chloroplasts may be linked to 5'-end of the PPO gene in order to express the herbicide-resistant PPO gene in the chloroplasts.

The vector may further include a gene encoding selectable marker as a reporter molecule, and example of the selectable marker may include antibiotics (e.g., neomycin, carbenicillin, kanamycin, spectinomycin, hygromycin, bleomycin, chloramphenicol, etc.) or herbicide (glyphosate, glufosinate, phosphinothricin, etc.)—resistant genes, but is not limited thereto.

Methods of vector transformation include introduction of the recombinant plasmid into the plant using *Agrobacterium*-mediated transformation, electroporation, microparticle bombardment, polyethylene glycol-mediated uptake, etc.

Plant transformation recipients in the present invention include a plant cell (containing a suspension-cultured cell), a protoplast, a callus, a hypocotyl, a seed, a cotyledon, a shoot as well as a mature plant.

Further, the scope of the transgenic or gene-edited plant includes a contemporary plant introduced with the gene as well as a clone or progeny thereof (T1 generation, T2 generation, or any subsequent generations). For example, the transgenic or gene edited plant comprising nucleotide sequence encoding the PPO polypeptide tolerant to the PPO-inhibiting herbicides provided in the present inventions, and a progeny comprising nucleotide sequence encoding the PPO polypeptide tolerant to the above mentioned PPO-inhibiting herbicides obtained by sexual and asexual reproduction, and the plant with inherited herbicide resistant characteristic is also included. The scope of the present invention also includes all mutants and variants showing the characteristics of the initial transgenic or gene-edited plant, together with all hybridization and fusion products of the above-mentioned transgenic or gene-edited plant. Furthermore, the scope of the present invention also includes a part of the plant, such as a seed, a flower, a stem, a fruit, a leaf, a root, a tuber, a tuberous root, which is originated from a plant which is modified by transgenic or gene editing in advance by the method of the present invention, or a progeny thereof, and is composed of at least a part of the cells modified by transgenes or gene editing.

The present invention also provides a method for controlling weeds in a plant cultivation site, comprising applying to the cultivation site a herbicidally effective amount of PPO-inhibiting herbicide, wherein the plant comprises the aforementioned plant or a plant produced by the aforementioned method.

In one embodiment, one PPO-inhibiting herbicide is used to control weeds.

In another embodiment, two or more PPO-inhibiting herbicides are used in sequence or in the mean time to control weeds.

In another embodiment, the PPO-inhibiting herbicide is applied in combination with one or more additional herbicides.

In the present invention, the term "cultivation site" includes a site in which plants of the present invention are cultivated, such as soil, and also includes, for example, plant seeds, plant seedlings, and grown plants. The term "herbicidally effective amount" means the amount of an herbicide that is enough to affect the growth or development of target weeds, for example, preventing or inhibiting the growth or development of the target weeds, or killing the weeds. Advantageously, said herbicidally effective amount does not significantly affect the growth and/or development of a plant seed, plant seedling or plant of the present invention. A person skilled in the art can determine such a herbicidally effective amount through conventional experiments.

This invention may be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that, although the terms "first," "second," "third" etc. may be used herein to describe various elements or components, these elements or components should not be limited by these terms. These terms are only used to distinguish one element or component from another element or component.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, elements, and/or components, but do not preclude the presence or addition of one or more other features, elements or components, and/or groups thereof. As used herein, the term "and/or" includes any and all combinations of one or more of the associated listed items.

While the invention has been described in detail in connection with a number of embodiments, the invention is not limited to such disclosed embodiments. Rather, the invention can be modified to incorporate any number of variations, alterations, substitutions or equivalent arrangements not heretofore described, but which are commensurate with the scope of the invention.

The beneficial effects of the present invention are: the mutation forms can reduce the inhibition effect of PPO-inhibiting herbicides against PPO with mutation forms, but at the same time, these mutants do not reduce the catalytic activity of PPO itself. The resistance of plants to PPO-inhibiting herbicides can be greatly improved by modifying the endogenous PPO into these mutation forms by gene editing or introducing genes with such PPO mutation forms into plants by transgenic means. Such PPO mutation forms can be used in plants including commercial crops according to the herbicide resistance characteristics and herbicide selectivity, so as to control weed growth economically.

The present invention will be further described in conjunction with the examples below. All of the methods and operations described in the examples are provided by way of exemplifications and should not be construed as limitation.

EXAMPLE 1

Example 1: Alignment of Amino Acid Sequences of PPO from Plants

PPO, existing in animals, plants, bacteria and fungi, catalyzes protoporphyrinogen IX into protoporphyrin IX in the presence of molecular oxygen. PPO is the last key enzyme in the biosynthesis of tetrapyrrole with ferroheme and chlorophyll as its main synthetic products. There are two PPO isoenzymes in plants, which are located in mitochondrion and chloroplast, respectively. FIG. 1 shows the alignment of PPO amino acid sequences from different plants, including rice (NCBI NO: XM 015770568.2 (SEQ ID NO: 1)), corn (NCBI NO: NM_001112094(SEQ ID NO: 2)), oilseed rape (NCBI NO: BnPPO1-C5: XM_013841402.2 (SEQ ID NO: 3); BnPPO1-A10: XM_013810914.2(SEQ ID NO: 4)), peanut (NCBI NO: AhPPO1-A: XM_025762937.2 (SEQ ID NO: 5); AhPPO1-B: XM_025820369.2(SEQ ID NO: 6)), soybean (NCBI NO: XM_003535957.4(SEQ ID NO: 7)), *sorghum*(NCBI NO: XM_002455439.2(SEQ ID NO: 8)), wheat (NCBI NO: TaPPO1-A: XP_037432241.1 (SEQ ID NO: 9); TaPPO1-B: XM_037583444.1(SEQ ID NO: 10); TaPPO1-D: (SEQ ID NO: 11)), tomato (NCBI NO: NM_001348379.1(SEQ ID NO: 12)), potato (NCBI NO: NP_001275224.1(SEQ ID NO: 13)), tobacco (NCBI NO: XM_016654498.1(SEQ ID NO: 14)), *Arabidopsis thaliana* (NCBI NO: AT4G01690(SEQ ID NO: 15)), upland cotton (NCBI NO: XM_016840317.1(SEQ ID NO: 16)), radish (NCBI NO: XP_018459031.1(SEQ ID NO: 7)), foxtail millet (NCBI NO: XP_004967639.1(SEQ ID NO: 18)), cabbage (NCBI NO: XM_013731605.1(SEQ ID NO: 19)), yam (NCBI NO: XP_039129342.1), cassava (NCBI NO: XM_021757904.2), pepper (NCBI NO: XM_016683798.1), squash (NCBI NO: XM_023107680.1), barley (NCBI NO: XM_045092307.1), cucumber (NCBI NO: XM_004149431.3), lettuce (NCBI NO: XM_023904577.2), sesame (NCBI NO: XM_011081162.2), sunflower (NCBI NO: XM_022132124.2), mulberry (NCBI NO: XM_010093132.2), cowpea (NCBI NO: XM_017556834.1), strawberry (NCBI NO: XM_004289391.2), apple (NCBI NO: XM_008383404.3), peach (NCBI NO: XM_007221411.2), cherry (NCBI NO: XM_021956996.1), apricot (NCBI NO: XM_034353497.1), grape vine (NCBI NO: XM_002273757.4), *papaya* (NCBI NO: XM_022041496.1), alfalfa (NCBI NO: XM_013613689.3), which indicates that the PPO protein motif LLLNYI is conservative between different plant species. Therefore, the biological effect of mutations at the corresponding sites of this motif may also be consistent across different species.

EXAMPLE 2

Example 2: Cloning of Rice Proporphyrinogen Oxidase PPO1 Gene

The rice (*Oryza sativa, Japonica* Group) protoporphyrinogen IX oxidase (PPO) gene is located at Os01g18320 site of No. 1 chromosome. The primers NusOs-F:acgattgatgacgacgacaagATGGCGGCGGCGGCGGCG and NusOs-R:tccacgagctcccggactcTTACTTGTACGCATACTTGGTC were designed and synthesized according to its cDNA sequence and the vector pET-44a sequence. The cDNA of wild-type rice was used as template and Kod DNA polymerase was used for PCR amplification. The amplification was carried out under the following conditions: 98° C. for 2 minutes; then 98° C. for 20 seconds, 65° C. for 30 seconds, and 68° C. for 60 seconds, 35 cycles; and at last 68° C. for 5 minutes. The amplified fragment was shown as 1.6 Kb in agarose gel electrophoresis and the DNA concentration thereof was determined by ultraviolet absorption after recovery.

The pET-44a (Novagen) plasmid was digested by PshAI (NEB, New England Biolabs, Boston, USA) at 37° C. for 1 hour, and then heated to 65° C. to inactivate PshAI. Equal amounts of OsPPO1DNA fragment and PshAI linearized pET-44a vector were mixed, then equal volumes of 2×Gibson Assembly Master Mix (Hanbio, Shanghai, China) were added. After mixing, the homogeneous mixture was incubated at 50° C. for one hour. 5 μl of the ligation product was used to transform the competent *Escherichia coli* DH5a; the bacterial solution was spreaded to the surface of an LB solid medium plate containing 100 ppm of ampicillin and cultured overnight at 37° C. On the next day, individual clones were selected and the correct clones were confirmed by individual bacterial colony PCR, after that, three correct clones were cultivated overnight at 37° C., and sufficient plasmid DNA was extracted and sent to Qingke Biotechnology Co., Ltd. (Beijing, China) for Sanger sequencing. The sequencing primers used were NUS-F: GCTGCTGCGAAATTTGAACG and NUS-R: TACAGCTGTGCGGCCGCAAG. The sequencing result proved that the correct full-length rice OsPPO1 coding region DNA could be obtained, and the expression vector of the expressed wild-type rice PPO was named as pET44a-OsPPO1 WT.

The tolerance of rice OsPPO1 to herbicides was tested by using PPO-deficient *Escherichia coli* (ΔhemG). ΔhemG strain is an *E. coli* strain lacking the hemG-type PPO gene and having kanamycin tolerance (Watanabe N, Che F S, Iwano M, et al. Dual Targeting of Spinach Protoporphyrinogen Oxidase II to Mitochondria and Chloroplasts by Alternative Use of Two In-frame Initiation Codons[J]. Journal of Biological Chemistry, 2001, 276(23):20474-20481.). The cloned rice OsPPO1 plasmid prepared above was transfected into competent cells of ΔhemG, and the PPO activity of the knockout bacteria was recovered by electrotransformation. The rice OsPPO1 plasmid could be grown on LB AGAR medium supplemented with ampicillin and kanamycin.

In order to verify whether this system could be used for evolutionary screening of rice PPO1 gene tolerance to compound A, a complementary strain of wild-type rice pET44a-OsPPO1 WT was used to test the growth difference of complementary strain on the plate containing PPO-inhibiting herbicides. Clones of the transformed complementary strains ΔhemG/pET44a and ΔhemG/pET44a-OsPPO1 WT were selected and resuspended in 100 ul LB medium. The diluted solution was then diluted again for four consecutive times with a coefficient of one-tenth. Then, 3 μl of each diluted solution was added onto LB agar medium (culture dish) containing compound A at concentrations of 0 nM, 300 nM and 1000 nM. The LB agar medium was cultured at 28° C. and the growth inhibition was assessed after 40 to 48 hours of cultivation.

Figure 2:
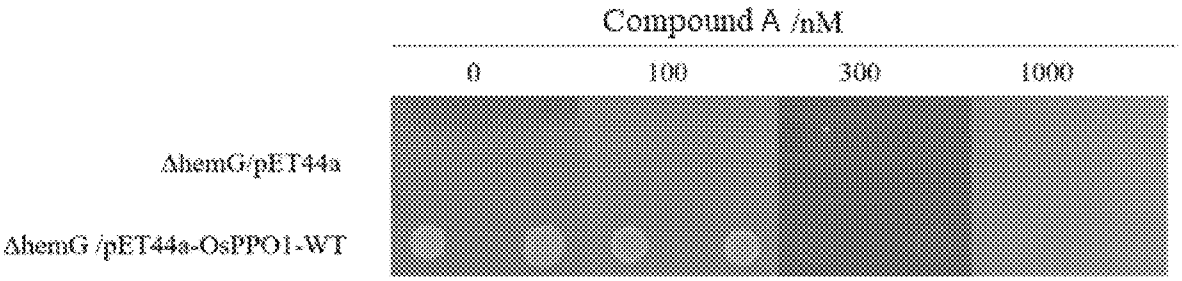
FIG. 2 shows the cell growth level of PPO-deficient *Escherichia coli* (ΔhemG) treated with compound A at 0 nM, 100 nM, 300 nM and 1000 nM (nanomloar) after transformed by pET44a empty vector and rice OsPPO1 wild-type gene (WT).

As shown in FIG. 2, on culture medium without herbicide, the ΔhemG/pET44a complementary strain did not grow while the complementary strain of the transformed rice ΔhemG/pET44a-OsPPO1 WT was able to grow normally, which indicated that the complemented OsPPO1 could perform normal PPO functions in defective *E. coli.*

It can also be seen that the growth of wild type rice ΔhemG/pET44a-OsPPO1 WT complementary strain was inhibited at 300 nM and no clone grew on the plate in the medium containing different concentrations of compound A. It was also demonstrated that this system could be used for evolutionary screening of rice OsPPO1 gene tolerance to compound A.

EXAMPLE 3

Figure 3:
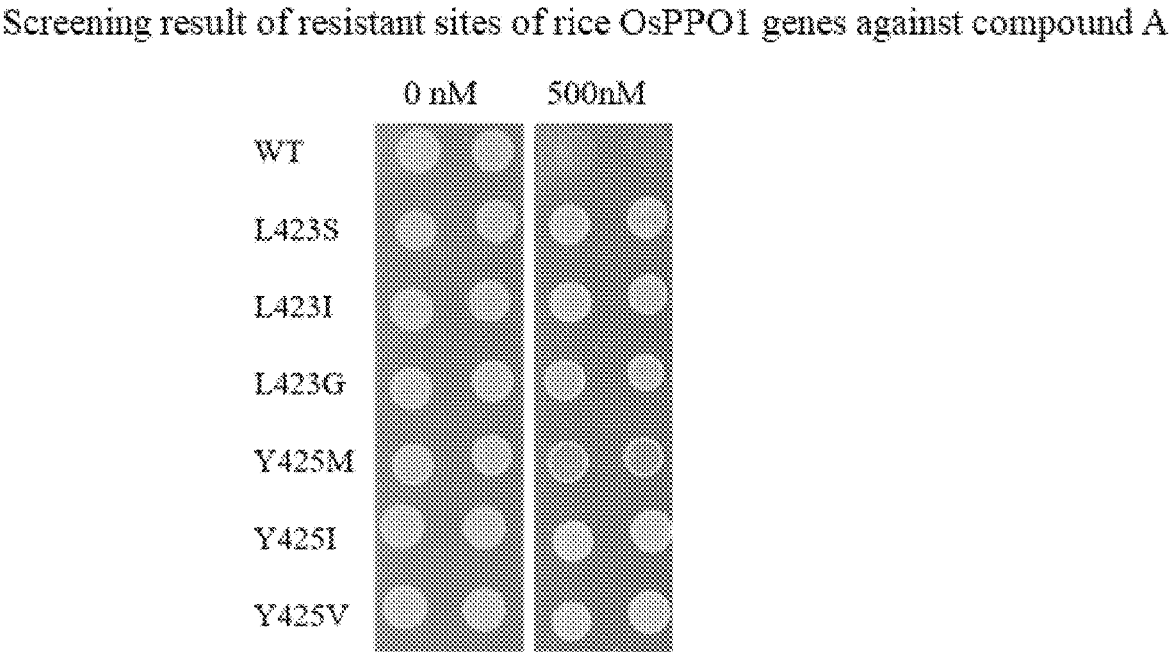
FIG. 3 shows the cell growth level of PPO-deficient *Escherichia coli* (ΔhemG) transformant transformed by OsPPO1 wild-type gene (indicated as WT) or various OsPPO1 mutant genes when treated with compound A at concentrations of 0 nM and 500 nM.

Example 3: Using PPO-Deficient *E. coli* (ΔhemG) to Screen the Site of Rice OsPPO1 Tolerance to Compound a In order to screen out the sites of rice OsPPO1 gene tolerance to compound A, a saturated mutation of amino acid was carried out at the sites with motif LLLNYI in rice according to the alignment result of PPO amino acid from different plants in Example 1. This was achieved by the PCR amplification of a primer containing the desired mutation of changing amino acid coding sequence into NNK and another suitable conventional primer. In NNK, N represented A/T/G/C and K represented G/T, and the NNK codon could encode any one of the 20 amino acids or stop condons. Accordingly, this was a saturated saturation mutagenesis. please see: Kille S, Acevedo-Rocha C G, Parra L P, Zhang Z G, Opperman D J, Reetz M T, Acevedo J P (2013) Reducing codon redundancy and screening effort of combinatorial protein libraries created by saturation mutagenesis. ACS Synth Biol 2(2):83-92; Directed Evolution Library Creation: methods and protocols 2nd ed. Edited by Elizabeth M. J. Gillam, Janine N. Copp and David F. Ackerley New York, NY United States: Springer, 2014.doi:10.1007/978-1-4939-1053-3. A large number of mutants would be produced. The constructed plasmids of saturation libraries with different sites were transformed into ΔhemG competent cells and the screening test of the tolerance of rice PPO1 gene different sites to compound A was conducted by using *E. coli* screening system in Example 2, then the normally-growing resistant clones were selected from the plate containing compound A and the genotypes thereof were identified. Six single amino acid mutants were screened out, which respectively were L423S (SEQ ID NO: 20), L423I(SEQ ID NO: 21), L423G(SEQ ID NO: 22), Y425M(SEQ ID NO: 23), Y425I(SEQ ID NO: 24) and Y425V(SEQ ID NO: 25). Compared with the wild type, these resistant mutants grew normally on LB medium containing 500 nM compound A, as shown in FIG. 3.

Specific Experimental Methods

1. PCR amplification was carried out by using Kod DNA polymerase with synthesized OsPPO1-423-F and OsPPO1-423-R as primer and pET44a-OsPPO1 WT plasmid prepared in Example 2 as template. The amplification was carried out under the following conditions: 98° C. for 3 minutes; 98° C. for 20 seconds, 65° C. for 30 seconds, and 72° C. for 3 minutes, 35 cycles; and 72° C. for 5 minutes. After detection by agarose gel electrophoresis, the bands with correct size (about 9 KB) were recovered and the concentrations were determined by ultraviolet absorption.

2. 5 μl of recovery product was added to an equal volume of 2×Gibson Assembly Master Mix (Hanbio, Shanghai, China), and incubated at 50° C. for one hour after mixing well; 5 μl of the ligation product was used to transform the competent *Escherichia coli* DH5a, and the bacterial solution was spreaded onto the surface of an LB solid medium plate containing 100 ppm of ampicillin, and cultured overnight at 37° C. All the clones (colonies) on the plate were scrapped, plasmids were extracted, and the DNAs were quantified by UV absorption.

3. 100 ng of the constructed plasmid was transformed into ΔhemG competent cells, an LB medium plate containing 500 nM compound A was spreaded, and the cultivation was performed overnight. The normally-growing resistant clones were selected from the plate containing compound A and the genotypes thereof were identified.

TABLE 1

Primers used to prepare rice PPO mutants

| Name of the primer | Sequence of the primer (5'-3') |
|---|---|
| NusOs-F | acgattgatgacgacgacaagATGGCGGCGGCGGCGGCG |
| NusOs-R | tccacgagctcccggactcTTACTTGTACGCATACTTGGTC |
| OsPPO1-421-F | CCGGCGGGTCGTGTTNNKCTGCTGAACTATATC |
| OsPPO1-421-R | AACACGACCCGCCGGCGCAC |
| OsPPO1-422-F | CCGGCGGGTCGTGTTCTGNNKCTGAACTATATCGGC |
| OsPPO1-422-R | CAGAACACGACCCGCCGGCGCACGG |
| OsPPO1-423-F | GGTCGTGTTCTGCTGNNKAACTATATCGGCGGTAG |
| OsPPO1-423-R | CAGCAGAACACGACCCGCCGGCGCACG |
| OsPPO1-424-F | TCGTGTTCTGCTGCTGNNKTATATCGGCGGT |
| OsPPO1-424-R | CAGCAGCAGAACACGACCCGCCGGCGC |
| OsPPO1-425-F | GTTCTGCTGCTGAACNNKATCGGCGGTAGCACC |
| OsPPO1-425-R | GTTCAGCAGCAGAACACGACCCGCCG |
| OsPPO1-426-F | CTGCTGCTGAACTATNNKGGCGGTAGCACCAA |
| OsPPO1-426-R | ATAGTTCAGCAGCAGAACACGACCCGC |

TABLE 1-continued

| Primers used to prepare rice PPO mutants | |
|---|---|
| Name of the primer | Sequence of the primer (5'-3') |
| OsPPO1-423S/425I-F | GGTGTTACTTTCCAACATCATAGGAGGTTCTACAAAT |
| OsPPO1-423S/425I-R | GTATTTGTAGAACCTCCTATGATGTTGGAAAGTAACACC |

EXAMPLE 4

Example 4: Verifying the Herbicide Tolerance of Rice OsPPO1 Resistance Site Combination by Using the PPO-Deficient *E. coli* (ΔhemG)

Figure 4:
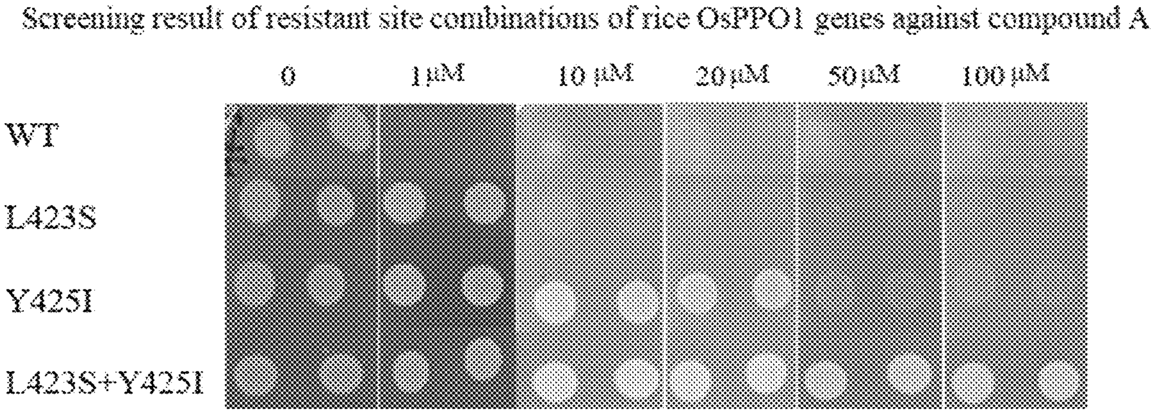
FIG. 4 shows the cell growth level of PPO-deficient *Escherichia coli* (ΔhemG) transformant transformed by OsPPO1 wild-type gene (indicated as WT) or various OsPPO1 mutant genes when treated with compound A at concentrations of 0 μM, 1 μM, 10 μM, 20 μM, 50 μM and 100 μM, respectively.

To further enhance the tolerance of rice OsPPO1 to PPO-inhibiting herbicides, the screened single mutants L423S and Y425I with tolerance to compound A were preferably selected and combined, and the tolerance to herbicides thereof was tested by using the *E. coli* screening system. It can be seen that the L423S/Y425I site combination (SEQ ID NO: 26) also showed tolerance to compound A. The screened single sites or site combinations were cultured on plates containing compound A at different concentrations of 0 μM, 1 μM, 10 μM, 20 μM, 50 μM and 100 μM, and the growth inhibition thereof was observed. The screening results were shown in FIG. 4, showing significant inhibition of growth occurred at certain site combinations as the concentration of compound A increased, but the mutant site combination L423S/Y425I showed higher tolerance and also normal growth with the treatment of compound A at the concentration of 100 μM. It indicated that the mutant site L423S/Y425I combination improved rice tolerance to herbicide compound A as compared with the single mutants L423S and Y425I.

Specific Experimental Methods

1. PCR amplification was carried out by using Kod DNA polymerase with the synthesized OsPPO1-423S/425I-F and OsPPO1-423S/425I-R as primer and the pET44a-OsPPO1 WT plasmid prepared in Example 2 as template. The amplification was carried out under the following conditions: 98° C. for 3 minutes; 98° C. for 20 seconds, 65° C. for 30 seconds, and 72° C. for 3 minutes, 35 cycles; and 72° C. for 5 minutes. After detection by agarose gel electrophoresis, the bands with correct size (about 9 KB) were recovered and the concentrations were determined by ultraviolet absorption.

2. 5 μl of recovery product was added to an equal volume of 2×Gibson Assembly Master Mix (Hanbio, Shanghai, China), and incubated at 50° C. for one hour after mixing well; 5 μl of the ligation product was used to transform the competent *Escherichia coli* DH5a, and the bacterial solution was coated to the surface of an LB solid medium plate containing 100 ppm of ampicillin, and cultured overnight at 37° C. All the clones (colonies) on the plate were scrapped, plasmids were extracted, and the DNAs were quantified by UV absorption.

3. 100 ng of the constructed plasmid was transformed into ΔhemG competent cells, an LB medium plate containing 500 nM compound A was spreaded, and the cultivation was performed overnight. The growth inhibition was observed.

4. Clones of the transformed complementary strains ΔhemG/pET44a-OsPPO1 WT, ΔhemG/pET44a-OsPPO1 L423S, ΔhemG/pET44a-OsPPO1 Y425I and ΔhemG/pET44a-OsPPO1 L423S/Y425I were selected and resuspended in an 100 ul LB medium, and the diluted solution was then diluted again for four consecutive times with a coefficient of one-tenth. Then, 3 μl of each diluted solution was added onto LB agar medium (culture dish) containing compound A at concentrations of 0 nM, 1 nM, 10 nM, 20 nM, 50 nM and 100 nM. The LB agar medium was cultured at 28° C. and the growth inhibition was assessed after 40 to 48 hours of cultivation.

EXAMPLE 5

Figure 5:
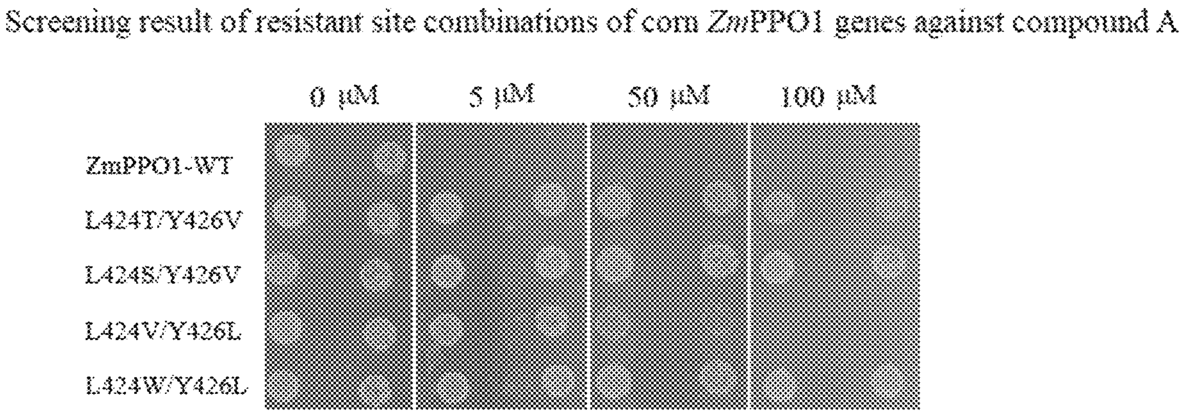
FIG. 5 shows the cell growth level of PPO-deficient *Escherichia coli* (ΔhemG) transformant transformed by ZmPPO1 wild-type gene (indicated as ZmPPO1-WT) or various ZmPPO1 mutant genes when treated with compound A at concentrations of 0 μM, 5 μM, 50 μM and 100 μM, respectively.

Example 5: Verifying the Tolerance of a Mutant LLLNYI Protein Motif in Corn ZmPPO1 to Compound A To verify whether the mutation of the PPO1-conserved protein motif LLLNYI in other plants could also confer resistance to herbicides, the mutation combination of leucine residues at the third position and tyrosine residues at the fifth position in the protein motif LLLNYI was carried out by using the same method as described in the above examples and screened by using of the LB medium containing herbicidal compound A, and the growth inhibition was observed. As shown in FIG. 5, compared with wild-type ZmPPO1-WT (SEQ ID NO: 2), the mutation combinations of leucine residues at the third position and tyrosine residues at the fifth position in the protein motif LLLNYI, comprising L424T/Y426V (SEQ ID NO: 27), L424S/Y426V (SEQ ID NO: 28), L424V/Y426L (SEQ ID NO: 29) and L424W/Y426L (SEQ ID NO: 30), grew normally without an inhibition on plates containing compound A at the concentration of 5 μM. The majority thereof showed a high tolerance with the increased concentration of compound A, indicating that tolerance to herbicides conferred by the mutation at the corresponding site of the PPO-conserved protein motif LLLNYI in different plants also had the consistent effects.

EXAMPLE 6

Figure 6:
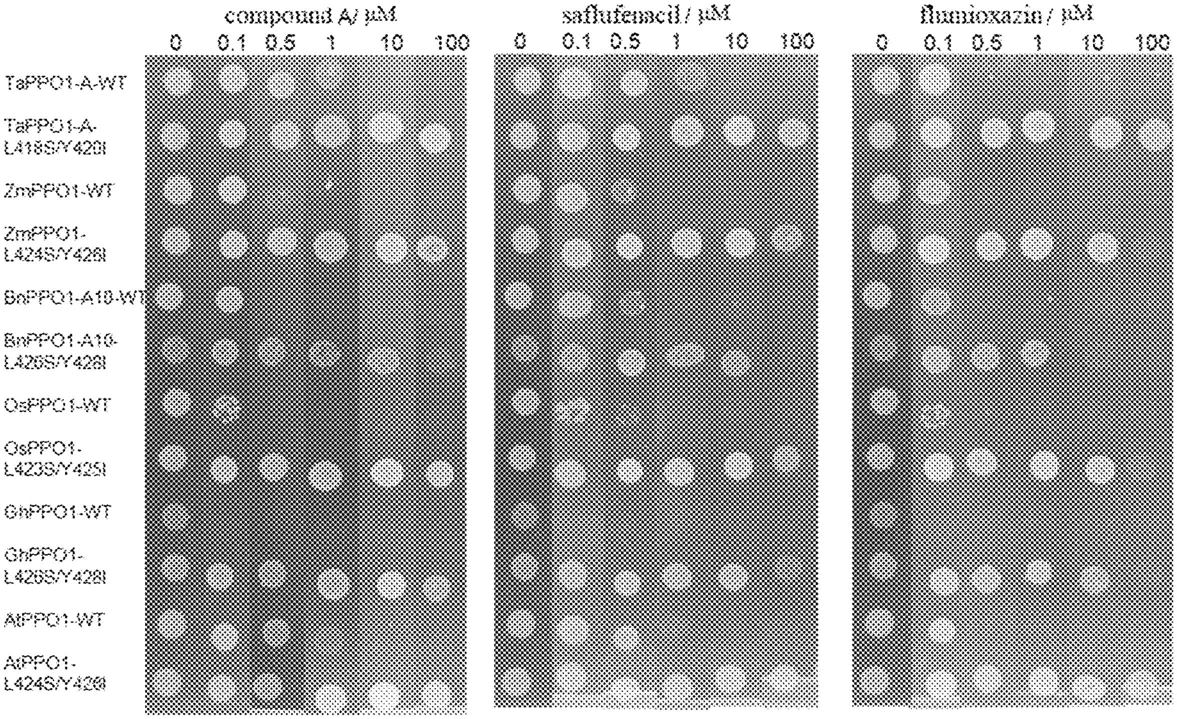
FIG. 6 shows the resistance test of other crop resistance site combinations against different PPO-inhibiting herbicides such as compound A, saflufenacil and flumioxazin.
Figure 7:
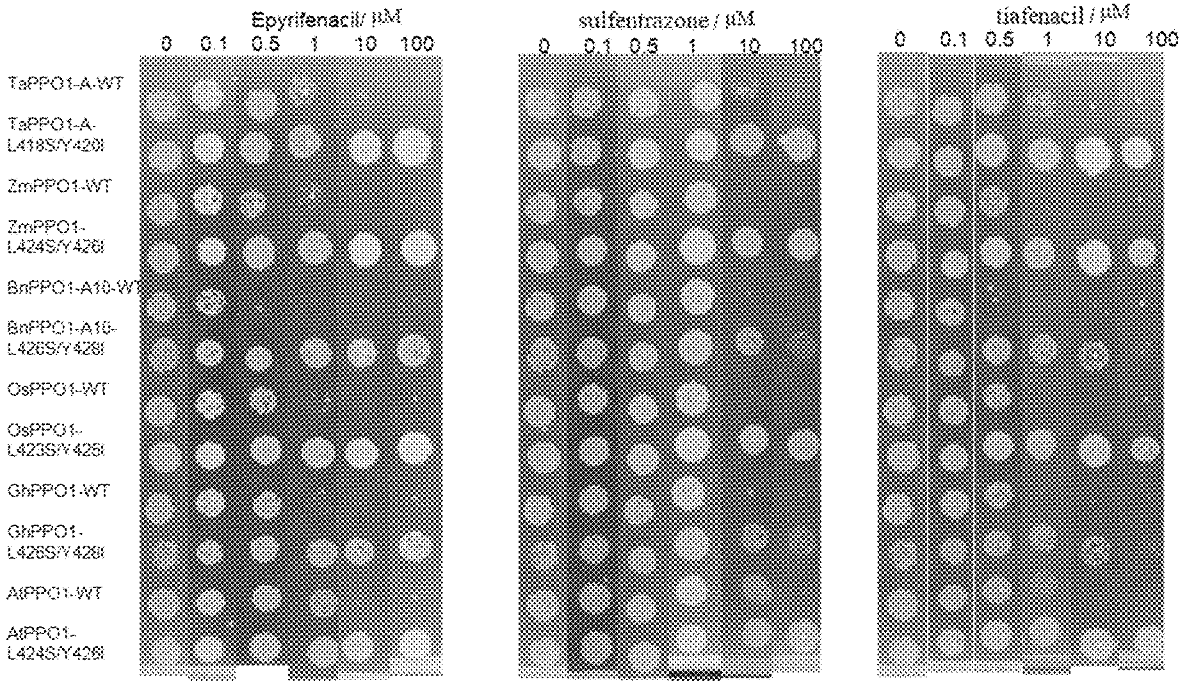
FIG. 7 shows the resistance test of other crop resistance site combinations against different PPO-inhibiting herbicides such as epyrifenacil, sulfentrazone and tiafenacil.
Figure 8:
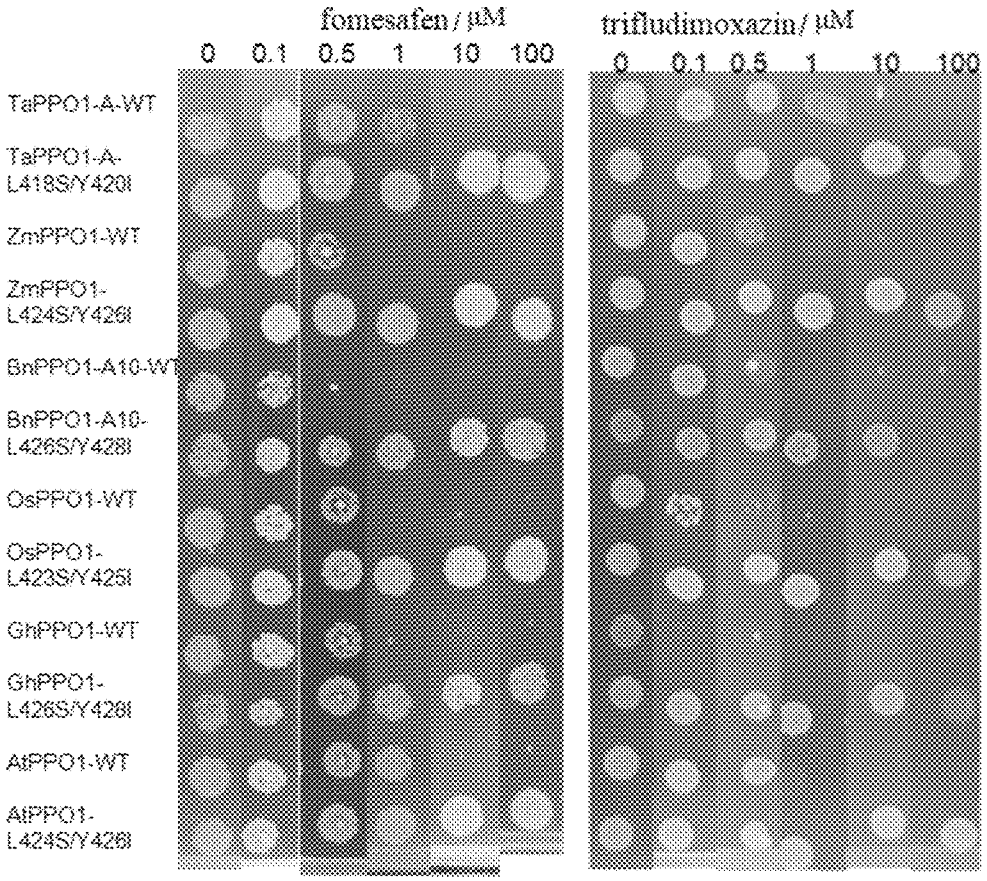
FIG. 8 shows the resistance test of other crop resistance site combinations against different PPO-inhibiting herbicides such as fomesafen and trifludimoxazin.

Example 6: Verifying the Tolerance of LLLNYI Protein Motif Mutation to Compound a and Other PPO-Inhibiting Herbicides in PPO1 of Other Crops To further verify the effect on the tolerance to herbicides conferred by a mutation at the corresponding site of the PPO-conserved protein motif LLLNYI in other crops, the vector containing the expressed genes comprising OsPPO1 WT (SEQ ID NO: 1) of wild-type rice PPO1, OsPPO1 L423S/Y425I (SEQ ID NO: 26) of mutant rice PPO1, ZmPPO1WT (SEQ ID NO: 2) of wild-type corn PPO1, ZmPPO1 L424S/Y426I (SEQ ID NO: 31) of mutant corn PPO1, TaPPO1-A WT (SEQ ID NO: 9) of wild-type wheat PPO1, TaPPO1-A L418S/Y420I (SEQ ID NO: 38) of mutant wheat PPO1, BnPPO1-A10 WT (SEQ ID NO: 4) of wild-type oilseed rape PPO1, BnPPO1-A10 L423S/Y425I (SEQ ID NO: 33) of mutant oilseed rape PPO1, GhPPO1 WT (SEQ ID NO: 16) of wild-type cotton PPO1, GhPPO1 L426S/Y428I (SEQ ID NO: 45) of mutant cotton PPO1, AtPPO1 WT (SEQ ID NO: 15) of wild-type *Arabidopsis thaliana* PPO1 and AtPPO1 L423S/Y425I (SEQ ID NO: 44) of mutant *Arabidopsis* PPO1, was constructed and transformed into PPO-deficient *Escherichia coli* (ΔhemG) for complementary by using the same method described in Example 3 and Example 4 and the primers as shown in Table 2. Clones of PPO-deficient *Escherichia coli* (ΔhemG) transformed by wild-type PPO1 genes or various mutant PPO1 genes in different crops were selected and resuspended in an 100 ul LB medium, and the diluted solution was then diluted again for two times with a coefficient of one-tenth. Then, 3 μl of each diluted solution was added onto LB agar medium (culture dish) containing respectively compound A at concentrations of 0.1 μM, 0.5 μM, 1 μm, 10 μM and 100 μM, saflufenacil at concentrations of 0.1 μM, 0.5 μM, 1 μM, 10 μM and 100 μM, flumioxazin at concentrations of 0.1 μM, 0.5 μM, 1 μM, 10 μM and 100 μM, epyrifenacil at concentrations of 0.1 μM, 0.5 μM, 1 μM, 10 μM and 100 μM, sulfentrazone at concentrations of 0.1 μM, 0.5 μM, 1 μM, 10 μM and 100 μM, tiafenacil at concentrations of 0.1 μM, 0.5 μM, 1 μM, 10 μM and 100 μM, fomesafen at concentrations of 0.1 μM, 0.5 μM, 1 μM, 10 μM and 100 μM and trifludimoxazin at concentrations of 0.1 μM, 0.5 μM, 1 μM, 10 μM and 100 μM. The LB agar medium was cultured at 28° C. in thermostatic incubator and the growth inhibition was assessed after 40 to 48 hours of cultivation. The results were shown in FIGS. 6-8, indicating that the resistance sites or combinations in examples 3 and 4 were also tolerant to other PPO herbicides.

TABLE 2

List of primers

| Name of the primer | Sequence of the primer (5'-3') |
|---|---|
| NusOs-F | acgattgatgacgacgacaagATGGCGGCGGCGGCGGCG |
| NusOs-R | tccacgagctcccggactcTTACTTGTACGCATACTTGGTC |
| OsPPO1-423S/425I-F | GGTGTTACTTTCCAACATCATAGGAGGTTCTACAAAT |
| OsPPO1-423S/425I-R | GTATTTGTAGAACCTCCTATGATGTTGGAAAGTAACACC |
| TaPPO1A-F | ccgcgcggcagccatATGGCCGGCGCAACAATG |
| TaPPO1A-R | tttgttagcagccggatcTCACTTGTAGGCATACTTGGTC |
| TaPPO1-418S/420I-F | GGAAGAGTGTTACTTtcGAACatTATCGGGGGTTC |
| TaPPO1-418S/420I-R | AAGTAACACTCTTCCAGCAGGAGCACG |
| ZmPPO1-T38F | ccgcgcggcagccatatggctgctgtggcgggggcg |
| ZmPPO1-R | tttgttagcagccggatctcacttgtaggcatacttggtcaag |
| ZmPPO1-424S/426I-F | ggtagggtgttacttAGCaacATTataggaggtgct |
| ZmPPO1-424S/426I-R | aagtaacaccctaccgtcaggagcacg |
| AtPPO1-F | tgccgcgcggcagccatatgTCagtggccggtggaccaac |
| AtPPO1-R | tttgttagcagccggatcttacttgtaagcgtaccgtgacatg |
| AtPPO1-423S/425I-F | ggaagaattttgctgAGCaacATTattgggggtctacaaac |
| AtPPO1-423S/425I-R | cagcaaaattcttccgggcggtgc |
| GhPPO1-F | TGCCGCGCGGCAGCCATatgacggctctaatcgacc |
| GhPPO1-R | GCTTTGTTAGCAGCCGGATCCttatttgtatgcatattgtg |
| GhPPO1-426S/428I-F | ggcagggtgttgctctCgaacATCataggaggag |
| GhPPO1-426S/428I-R | gagcaacaccctgccagatggagctcg |
| BnPPO1-A10-F | cgcgcggcagccatATGGATTTCTCTCTTCTCCGTCCGGC |
| BnPPO1-A10-R | gttagcagccggatcTTACTTGTAAGCATACCTTGACAT |
| BnPPO1-A10-426S/428I-F | GGAAGAGTGTTGCTATcGAACatCATCGGTGGAGCTAC |
| BnPPO1-A10-426S/428I-R | TAGCAACACTCTTCCAGGTGGTGCT |

EXAMPLE 7

Figure 9:
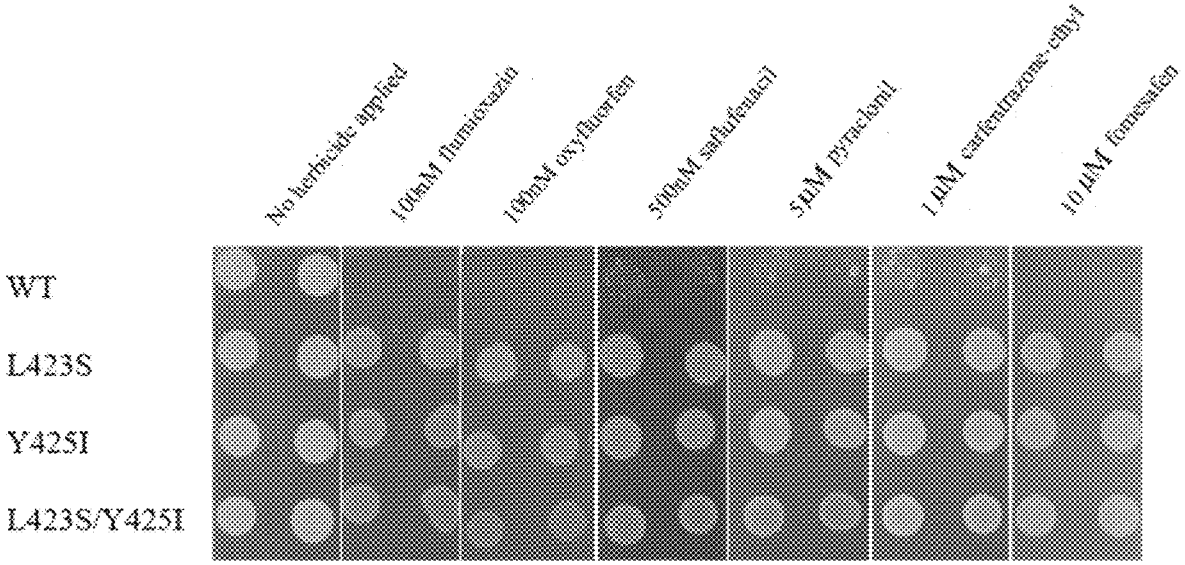
FIG. 9 shows the cell growth level of PPO-deficient *Escherichia coli* (ΔhemG) transformant transformed by OsPPO1 wild-type gene (indicated as WT) or various OsPPO1 mutant genes when treated with 100 nM flumioxazin, 100 nM oxyfluorfen, 500 nM saflufenacil, 5 μM pyraclonil, 1 μM carfentrazone-ethyl and 10 μM fomesafen, respectively.

Example 7: Verifying the Tolerance of the Resistance Sites or Combinations of Rice OsPPO1 to Different Types of PPO Herbicides To verify whether the resistance sites or combinations in examples 3 and 4 were also tolerant to other PPO herbicides, some sites or combinations were preferably selected to verify the tolerance thereof to different types of PPO herbicides. Clones of PPO-deficient *Escherichia coli* (ΔhemG) transformants transformed by wild-type (WT) OsPPO1 genes or various mutant OsPPO1 genes were selected and resuspended in an 100 ul LB medium, and the diluted solution was then diluted again for two consecutive times with a coefficient of one-tenth. Then, 3 of each diluted solution was added onto LB agar medium (culture dish) containing respectively flumioxazin at the concentration of 100 nM, oxyfluorfen at the concentration of 100 nM, saflufenacil at the concentration of 500 nM, pyraclonil at the concentration of 5 μM, carfentrazone-ethyl at the concentration of 1 μM and fomesafen at the concentration of 10 μM. The LB agar medium was cultured at 28° C. in thermostatic incubator and the growth inhibition was assessed after 40 to 48 hours of cultivation. The results were shown in FIG. 9, indicating that the resistance sites or combinations in examples 3 and 4 were also tolerant to other PPO herbicides.

EXAMPLE 8

Example 8: An In Vitro Enzyme Activity and Resistance Test of Resistance Site Combination Proteins (Polypeptides) of Rice OsPPO1

1. Preparation of Protoporphyrinogen

Protoporphyrinogen, a substrate catalyzed by PPO, was prepared by reducing protoporphyrin with sodium amalgam. 10 mg of protoporphyrin was dissolved in 10 mL solvent, added with 20% sodium amalgam at the rate of 0.2 g/mL, reacted for 2 hours, then filtered under the protection of nitrogen in dark place. After the reaction was completed, the reaction solution should become achromatic or light brown. The reaction solution was diluted by adding with reaction buffer (100 mM Tris-HCl, 1 mM EDTA, 5 mM DTT, 0.1% Tween 20/80), and 10% hydrochloric acid was used to adjust pH to about 8.0. Protoporphyrinogen at an approximate concentration of 100 μM was finally obtained, subpackaged and stored with liquid nitrogen or in a −80° C. temperature.

2. Expression and Purification of OsPPO1 Proteins

1) PCR amplification was carried out by using Kod DNA polymerase with pET44a-OsPPO1-WT and screening mutants as template and 28MBP-OsPPO1-T38F: CCGCGCGGCAGCCATATGGCGGGTTCTGGTACGATTG and 28MBP-OsPPO1-T38Rn: GAGCTCGAATTCGGATCCTTACTTGTACGCATACTTGGTCAG as primers. The amplification was carried out under the following conditions: 95° C. for 3 minutes; 98° C. for 10 seconds; 60° C. for 30 seconds; 68° C. for 1 minute, 35 cycles; and 68° C. for 5 minutes. After detection by agarose gel electrophoresis, the bands with correct size (about 1.5 KB) were recovered and the concentrations were determined by ultraviolet absorption.

2) 4 μl of recovery product and 1 μl of pET28a-MBP vector were added to an equal volume of 2×Gibson Assembly Master Mix (Hanbio, Shanghai, China), mixed, and incubated at 50° C. for one hour; 5 μl of the ligation product was used to transform the competent *Escherichia coli* DH5a, and the bacterial solution was spreaded to the surface of an LB solid medium plate containing 100 mg/L of kanamycin sulfate, and cultured overnight at 37° C. All the clones on the plate were selected and sequenced.

3) The constructed fusion expression vector pET28a-MBP-OsPPO1 was transferred into *E. coli* BL21 (DE3), subjected to induced-expression with 0.5 mM IPTG, then purified with the Ni-NTA column, afterwards subjected to thrombin digestion, dialysed, and purified secondly by dextrin-column and Ni-column. The specific methods were as follows. The OsPPO1 enzyme recombinant expression vector was transformed into the BL21 (DE3) cell, and the clone thereof was selected into 10 ml of LB medium and cultivated overnight with Kana resistance at 37° C. and on a shaker at 200 rpm, then transferred into a 2 L shake flask containing 1 L TB medium, cultivated on a shaker at 37° C. and 200 rpm until the OD600 reached 0.6-0.8, cooled to a temperature of 18° C., and subjected to induced-expression with 0.5 mM IPTG overnight. The strains were collected by centrifugation at 4000×g. The collected strains were re-suspended with the Ni-buffer A (50 mM Tris pH 8.0, 500 mM NaCl, 50 mM imidazole), homogenized by high pressure cell homogenizer, and centrifuged at 4000×g at 4° C. for 30 minutes; the supernatant was purified with the Ni column, then the purity thereof was detected by SDS-PAGE. The thrombin enzyme was added according to the quantity of proteins, dialyzed with 50 mM Tris pH 8.0, 500 mM NaCl, 1 mM DTT buffer. On the second day, then purified by dextrin-column and Ni column successively; and the eluates containing of the protein of interest were collected, concentrated, subpackaged and stored in a −80° C. temperature for later use.

3. Activity Test of OsPPO1

Determination of substrate affinity and catalytic activity of enzymes: the reaction buffer (100 mM Tris-HCl, 1 mM EDTA, 5 mM DTT, 0.1% Tween 20/80) was used to prepare the reaction solution containing the substrate protoporphyrinogen with different concentrations, and the test concentrations were 0.125, 0.5, 2, 4, 8 and 16 μM. The OsPPO1 enzyme was diluted to 10 μM and 5 μl was absorbed to a black 96-well ELISA plate, to which the reaction solution was added until the total volume reached 100 μl. The final working concentration of enzyme was 500 nM. The solution was immediately well mixed and monitored by a fluorescence microplate reader. The mix was stimulated at 410 nm and detected at 630 nm. The reaction curves were made, as shown in FIG. 10.

EXAMPLE 9

Example 9: Homologous Replacement of Rice PPO1 Mutant Mediated by CRISPR/Cas9 to Obtain Herbicide Resistance To obtain non-transgenic rice with herbicide resistance, the above mentioned L423S/Y425I mutation site combination was subjected to homologous replacement mediated by CRISPR/cas9. There were nine exons and eight introns in rice OsPPO1 gene, however, the two target sites L423S and Y425I were located at the eighth exon.

Design of gRNA: one gRNA was designed upstream of L423S and downstream of Y425I, respectively, and cleaved once at each site, respectively; and the DNA between two sites were simultaneously replaced by the means of homologous replacement. The sequence of rice OsPPO1 was input in http://crispor.tefor.net/crispor.py to evaluate all possible gRNAs. According to the principles that specificity scoring value was greater than 90 (Hsu P D, Scott D A, Weinstein J A, Ran F A, Konermann S, Agarwala V, Li Y, Fine E J, Wu X, Shalem O, Cradick T J, Marraffini L A, Bao G, Zhang F. Nat Biotechnol. 2013 September; 31(9):827-32. doi: 10.1038/nbt.2647. Epub 2013 Jul. 21), the off-target effect was avoided and the length was shortened as far as possible, the following two gRNAs were selected: gRNA: Osppo1 gRNA5-2:acatgaactagtaatgattgggg (top strand); and Osppo1 gRNA8-3: agcagctggagttgaaaaacagg (bottomstrand), wherein the underlined was the PAM sequence.

Design of repair template: the DNA fragment cleaved by two selected targeted RNAs was in length of 1212 bp. However, due to the close location of the sites 423 and 425, while designing the repair template, the left homology arm was in length of 1127 bp and the right homology arm was in length of 82 bp. Moreover, the digestion target sites were left at each of the left and right ends in order to cleave the repair template from the vector. So the total length of the template was 1258 bp (SEQ ID NO: 49).

Editing vector: the Osppo1 gRNA5-2 and Osppo1 gRNA8-3 were expressed respectively by rice U3 promoter. Thus, the two gRNA expression cassettes were sent together with the repair template to GenScript (Nanjing) Co., Ltd. for synthesis. The two synthesized gRNA expression cassettes and a vector pRGEB32 (Addgene #63142) were subjected to enzyme digestion with BsaI enzyme, detected by agarose gel electrophoresis, then purified and recovered, and ligated and transformed with T4DNA ligase (NEB, New England Biolabs, Boston, USA) to generate an editing vector.

Transformation by gene gun, screening, differentiation, rooting and soil cultivating seedlings: the above constructed editing vector was verified by sequencing and multi-enzyme digestion, and was then used together with the synthesized repair template NDA for rice transformation mediated by gene gun.

Specific Methods of the Transformation of Rice Callus Mediated by Gene Gun:

1. High-quality seeds from Huaidao No. 5 and Jinjing 818 rice varieties were selected, sterilized with the solution comprising 70% alcohol and 20% sodium hypochlorite, rinsed with sterile water, and inoculated into callus induction medium. After one week of cultivation, the embryos were removed and the exfoliated callus was inoculated into callus induction medium. After two weeks, subculture was carried out for subsequent infection.
2. Preparation of microprojectile and gene gun transformation (1) Preparation of gold powder suspension: 30 mg of gold powder (diameter 0.6 μm) was weighted by imported 1.5 mL EP tube, to which 1 mL of 70% ethanol was added, fully vortexed, and the supernatant was abandoned by centrifugation; sterile water was added to rinse and repeated for 3 times. 500 μL of sterile glycerol (50%) was added and vortexed thoroughly, and the gold powder suspension at a concentration of 60 μg/L was prepared, then stored at −20° C.

(2) DNA wrapping: 25 μL of gold powder suspension (60 μg/μL), editing vector and repair template (1:10), 25 μL of $CaCl_2$(SIGMA) (2.5 mol/L) and 10 μL of spermidine (0.1 mol/L) were added into 1.5 mL centrifuge tube successively. The above mixed sample was fully vortexed for 3-5 minutes and placed on ice for 10 minutes, and the supernatant was abandoned by centrifugation; finally, 30 μL of anhydrous ethanol was added for re-suspending and the final volume.

(3) Gene gun bombardment: the super clean bench was cleaned, the bench top was wiped with alcohol, the instrument was adjusted and the bombardment was carried out in accordance with the operation instructions. The bombardment parameter was adjusted to 27 vacuum degree, 1100 psi, 6 cm. After bombardment, the callus was cultured in darkness for 16 hours at 25° C., then the callus was transferred to the recovery medium at 25° C. for dark cultivation for one week.

(4) Screening of resistant callus and differentiation of plants: the callus was transferred to a screening medium for screening, and the medium was changed every two weeks. After four weeks of screening, samples were taken to detect whether target replacement occurred.

(5) The callus that tested positive was transferred to a differentiation medium wherein the differential culture was carried out in a light incubator at 28° C.

The transgenic rice genomic DNA was extracted after the resistant callus was induced into rice seedlings, and PCR amplification test was performed by using the DNA thereof as a template. The T0-generation rice line was successfully obtained by simultaneously replacement at site L423S/Y425I of the rice OsPPO1 gene. To further verify the tolerance of the obtained TO-generation rice seedlings to compound A, the rice seedlings were treated with compound A at the rate of 9 g/ha, and lines that carried homologous replacement at the site of L423S/Y425I grew normally, compared with wild-type lines which died 3 days after treatment, as shown in FIG. 11, indicating that the mutation of rice OsPPO1 gene at site L423S/Y425I conferred herbicidal compound A tolerance to the plant. Rice seedlings of T1-generation and T2-generation were obtained from the cultivation cultivated by harvesting seeds. It was proved that the obtained rice seedlings of T1-generation and T2-generation were also tolerant to compound A and the tolerance of T2-generation rice seedlings to compound A was shown in Table 3.

TABLE 3

Tolerance of T2-generation rice seedlings to compound A (soil treatment, 13DAA)

| Test Product | Rate (g a.i./ha) | Efficacy (Phytotoxicity) Ranking: T2-generation rice | Efficacy (Phytotoxicity) Ranking: Wild-type rice |
|---|---|---|---|
| 4.25% Compound A | 15 | 1 | 5 |
| | 30 | 2 | 7 |
| | 60 | 4 | 8 |
| | 120 | 6 | 9 |

Note:
0—No difference;
1—the plants are slightly burned;
2—the plants are significantly burned;
3—the plants are severely burned;
4—the plants are slight wilted;
5—the plants are significantly wilted;
6—the plants are severely wilted;
7—the minority die;
8—the majority die;
9—all die.

EXAMPLE 10

Example 10: Overexpressing the Tolerance of LLLNYI Protein Motif Mutations in PPO1 from Other Crops to Compound a in *Arabidopsis thaliana*

In order to rapidly verify the tolerance of LLLNYI protein motif mutations in PPO1 from different crops to compound A, vectors of overexpressed wild-type and mutant PPO1 genes in rice, corn, soybean and oilseed rape were constructed respectively.

1. Construction of the Overexpression Vector

1) Primers: Primers were designed according to the selected restriction enzyme cutting sites and the nucleotide sequence of the gene itself to amplify the wild-type and mutant. The designed primers were synthesized by Beijing Qingke Biotechnology Co., Ltd.

| Name of the primer | Sequence of the primer (5'-3') |
|---|---|
| 401V-OsPPO1-F | gatactcgagtaatctagaatggccgccgccgccgcag |
| 401V-OsPPO1-R | cgaacgaaagctctgagctctcacttgtaggcgtacttg |
| 401V-ZmPPO1-F | gatactcgagtaatctagaatggtcgccgccaccgcc |
| 401V-ZmPPO1-R | cgaacgaaagctctgagctctcacttgtaggcatacttg |
| 401V-GmPPO1-F | gatactcgagtaatctagaAtggtttccgtcttcaac |
| 401V-GmPPO1-R | cgaacgaaagctctgagctcctatttgtacactctatttg |
| 401V-BnA10-PPO1-F | gatactcgagtaatctagaATGGATTTCTCTCTTCTCC |
| 401V-BnA10-PPO1-R | cgaacgaaagctctgagctcTTACTTGTAAGCATACCTTG |

2) PCR amplification: The gene of interest was amplified by using the synthesized primers and Q5DNA polymerase (NEB, New England Biolabs, Boston, USA). The amplified product was detected by agarose gel electrophoresis and recovered according to the operating instructions of TIAN quick Midi Purification kit. After the completion of the recovery, the concentration of DNA extracted was determined by Nanodrop.

3) Construction of overexpression vector: an overexpression vector was constructed with the recovered PPO1 fragment and plasmid pHSE401V digested by XbaI and SacI by using the HB-in fusionTM seamless cloning kit of HanBio Biotechnology Co., Ltd., (Shanghai), and then transformed into the competent *E. coli* DH5α to obtain a positive clone; the positive clone was transformed into *Agrobacterium* for later use after verified by sequencing and restriction endonuclease digestion.

2. Transformation of *Arabidopsis thaliana* by Dipping Inflorescences

1) Sowing: plump and vernalized wild-type *Arabidopsis thaliana* seeds were selected, treated with 75% alcohol for 1 minute, disinfected with 10% NaClO for 6 minutes, and washed with sterile water for 5 to 6 times. After the sterilization was completed, the seeds were placed on a MS medium plate for one week, then transplanted to sterilized nutrient soil (nutrient soil:vermiculite=1:1) and cultured in a greenhouse at (25±2) ° C. with a photoperiod of 16 h/8 h (light/dark).

2) Activation and preparation of *Agrobacterium: Agrobacterium* strains with expression vector stored at low temperature were streaked on a resistant plate containing clarithromycin and rifampicin. Single colonies were picked out and inoculated into the 5 mL liquid LB medium to which corresponding antibiotics were added, cultured in a shaker at 28° C. and 250 rpm for 18 to 24 hours. Then the cultivation was enlarged according to 1:100 inoculation under the same conditions and the total volume of bacteria solution was 50 ml until the OD6000 was in the range of 1.0-1.5.

3) Preparation of the infestation solution: the cultured bacteria solution was centrifuged at 6000 rpm for 10 minutes, and the supernatant was discharged. The stains were resuspended in the infestation solution containing 5% sucrose until the OD6000 was about 0.8. SilwetL-77 (0.02%-0.04%) was added to the bacteria solution and well mixed.

4) Infestation of *Arabidopsis thaliana* inflorescences: the uninfected *Arabidopsis thaliana* with good growth state and lush inflorescences were selected for infection and their fruit pods were cut off from the plants by scissors prior to transformation. The *Arabidopsis thaliana* inflorescences were dipped in the prepared infection solution for 0.5 to 1 minute. Then the infected *Arabidopsis thaliana* seedlings were placed in dark and humid conditions for 24 hours. After one week, the infection was repeated.

5) Screening of transgenic lines

After the transformation of dipped *Arabidopsis thaliana* inflorescences, *Arabidopsis thaliana* TO-generation seeds were collected and sowed on a resistant MS plate containing 30 mg/L hygromycin to screen positive plants. The screened positive seedlings were transferred to a pot containing soil and placed in a greenhouse for cultivation to obtain the following: the overexpressed rice OsPPO1 L423S/Y425I and the overexpressed the OsPPO1 WT seedlings or events in *Arabidopsis thaliana*; the overexpressed soybean GmPPO1 L430S/Y432I and the overexpressed GmPPO1 WT seedlings or events in *Arabidopsis thaliana*; the overexpressed oilseed rape BnPPO1-C5 L424S/Y426I and the overexpressed BnPPO1-C5 WT seedlings or events in *Arabidopsis thaliana*; the overexpressed corn ZmPPO1 L424T/Y426V, ZmPPO1 L424S/Y426V, ZmPPO1 L424V/Y426L, ZmPPO1 L424W/Y426L, ZmPPO1 L424S/Y426I and the overexpressed ZmPPO1 WT seedlings or events in *Arabidopsis thaliana*.

3. Herbicide Resistance Test

The obtained overexpressed mutant and wild-type *Arabidopsis thaliana* seeds of different crops were tested for resistance on a MS medium (petri dish) containing different concentrations of PPO-inhibiting herbicidal compounds, as shown in FIG. 12-23. Compared with wild-type *Arabidopsis thaliana*, both the overexpressed LLLNYI protein motif mutation in PPO1 from different crops and the overexpressed PPO1 WT showed certain level of tolerance/resistance to herbicides in the present invention, and their resistance levels were similar at the application concentration of 50 nM. However, at the higher application concentration of 2 μM, the overexpressed LLLNYI protein motif mutation in PPO1 from different crops still showed resistance while the overexpressed PPO1 WT from different crops showed no difference with the wild-type *Arabidopsis thaliana* control, indicating that after the overexpression of LLLNYI protein motif mutation in PPO1 from different crops, such crops would have a higher tolerance to PPO-inhibiting herbicidal compounds.

EXAMPLE 11

Example 11: Overexpressing Rice OSPPO1 L423S/Y425I Mutation to Obtain Herbicide Resistance In order to further test the tolerance of the obtained mutants in plants to compound A, the mutants L423S/Y425I screened from rice were overexpressed in rice.

1. Construction of the Overexpression Vector

1) Primers: primers were designed according to the selected restriction enzyme cleavage sites and the nucleotide sequence of the gene itself to amplify the mutant L423S/Y425I. The designed primers comprising PPO1-F: GCCAGTGCCAAGCTCTGCAGattcgggtcaaggcgga and PPO1-R:ACATGATTACGAATTCtctagtaacata-gatgacaccgcgc were synthesized by Beijing Qingke Biotechnology Co., Ltd.

2) PCR amplification: the gene of interest was amplified by using the synthesized primers and Q5DNA polymerase (NEB, New England Biolabs, Boston, USA). The amplified product was detected by agarose gel electrophoresis and recovered according to the operating instructions of TIAN quick Midi Purification kit. After the completion of the recovery, the concentration of extracted DNAs was determined by Nanodrop.

3) Construction of rice overexpression vector: a rice overexpression vector pCAMBIA1301-OsPPO1 L423S/Y425I was constructed with the recovered PPO1 fragment and plasmid pCAMBIA1301 digested by KpnI and Hind III by using the HB-in fusionTM seamless cloning kit of HanBio Biotechnology Co., Ltd., (Shanghai), and then transformed into the competent *E. coli* DH5a to obtain a positive clone. The positive clone was transformed into *Agrobacterium* after verified by sequencing and restriction endonuclease digestion.

2. *Agrobacterium*-Mediated Transformation of Rice Callus and Occurrence of Transgenic Events:

1) 100 ng of vector plasmid of rice overexpression vector pCAMBIA1301-OsPPO1 L423S/Y425I and pCAMBIA1301-OsPPO1 WT was aspirated and added in the competent *Agrobacterium* EH105, respectively, placed on ice for 5 minutes, rapidly frozed by immersing in liquid nitrogen for 5 minutes, fished out and stood at 37° C. for 5 minutes and finally placed on ice for 5 minutes; to which 500 μl of YEB solution culture (antibiotic-free) was added, and cultivated on a shaker at 28° C. and 200 rpm/minute for 2-3 hours; the colonies were collected by centrifugation at 3500 rpm/minute, and the collected cells were coated on the YEB (clarithromycin+rifampicin) plate and cultivated for 2 days in a 28° C. incubator; the single clones were picked out, cultivated in liquid medium and stored at −80° C. to keep the life of bacteria.

2) Cultivation of *Agrobacterium*: the transformed *Agrobacterium* single clones were picked out and cultured in YEB liquid medium (clarithromycin+rifampicin) in a shaker at 28° C. until the OD600 was 0.5, the colonies were collected at 3500 rpm, diluted with equal amount of AAM (1 ml AAM+1 μl 1000×AS) liquid medium to infect the callus.

3) Induction of callus from Huaidao No. 5 rice variety: prior to the preparation of *Agrobacterium*, rice callus was prepared at first. Rice seeds were peeled, washed with sterile water as many times as needed until the washing water became clear. Then the seeds were disinfected with 70% alcohol for 30 seconds and then with 5% sodium hypochlorite. The seeds were cultivated in a horizontal shaker for 20 minutes, disinfected with sodium hypochlorite and washed with sterile water for 5 times, placed on a sterile absorbent paper to air-dry the surface moisture of the seeds, and inoculated in an induction medium to cultivate the callus at 28° C.

4) Infection of rice callus with *Agrobacterium*: the Huaidao No. 5 callus with a diameter of 3 mm was selected for sub-cultivation for 10 days and the callus was collected into a 50 ml centrifuge tube. A bacterial solution of *Agrobacterium* with a modulated concentration was added into the centrifuge tube containing the callus, and the centrifuge tube was placed on a shaker at 28° C. and 200 rpm to infect for 20 minutes; after the infection was completed, the bacterial solution was discharged, and the callus was placed on a sterile filter paper and air-dried for about 20 minutes and co-cultivated on a co-culture plate on which an sterile filter paper wetted with an AAM (1 ml AAM+30 μl 1000×AS) liquid culture was covered; after 3 days of infestation, *Agrobacterium* was washed and removed (i.e., washed with sterile water for 5 times and then washed with 500 mg/L of cephalosporin antibiotic for 20 minutes), and then the callus was screened and cultivated in 50 mg/L hygromycin screening medium.

5) Screening, differentiation and rooting of resistant callus: the co-cultured callus was transferred to screening medium for the first round of screening (2 weeks); after the first round of screening was completed, the newly grown callus was transferred to screening medium (containing 50 mg/L hygromycin) for the second round of screening (2 weeks); after the screening was completed, yellow-white callus with a good growth state were picked out for differentiation, and seedlings of about 1 cm were obtained after 3 to 4 weeks. The differentiated seedlings were transferred to a rooting medium for rooting culture; the rooted seedlings were subjected to acclimatization treatment, and then transferred to a pot containing soil for cultivation in a greenhouse; and overexpressed OsPPO1 L423S/Y425I and overexpressed OsPPO1 WT seedlings or events were obtained.

3. Detection of herbicide resistance of transgenic seedlings (T0 generation): different concentrations of compound A were sprayed to overexpressed rice OsPPO1 L423S/Y425I and OsPPO1 WT of T0 generation rice seedlings for resistance test. As shown in FIG. 24, compared with wild-type Huaidao No. 5, both the overexpressed rice OsPPO1 L423S/Y425I and the overexpressed OsPPO1 WT showed certain level of tolerance/resistance to compound A. Their resistance levels were similar at 45 g/ha application concentration, but at higher application concentrations such as 135 g/ha and 270 g/ha, the overexpressed OsPPO1 L423S/Y425I still showed resistance while the overexpressed OsPPO1 WT showed no difference with the wild-type control, indicating that rice with overexpressed OsPPO1 L423S/Y425I has a higher tolerance to compound A.

At the same time, through many tests, it is found that introducing the corresponding resistance site or combination in the present invention into other plants by transgenic technology or gene editing technique would confer tolerance to PPO-inhibiting herbicides as well, indicating that it has good industrial value.

All publications and patent applications mentioned in the description are incorporated herein by reference, as if each publication or patent application is individually and specifically incorporated herein by reference.

Although the aforementioned invention has been described in more details by way of examples and embodiments for clear understanding, it is obvious that certain changes and modifications can be implemented within the scope of the appended claims, and such changes and modifications are all within the scope of the present invention.

The invention claimed is:

1. A PPO polypeptide tolerant to a PPO inhibitor herbicide, which is characterized in that the polypeptide comprises the motif "LLLNYI" (SEQ ID NO: 50), wherein the leucine L at position 3 within the motif is substituted with other amino acid, and the tyrosine Y at position 5 is substituted with other amino acid; and wherein:

as compared to the amino acid sequence of a wild-type rice PPO1, the amino acid sequence of the PPO polypeptide has mutations L423S/Y425I at positions corresponding to 423 and 425 of the amino acid sequence of wild-type rice PPO1 protein as set forth in SEQ ID NO: 1; or as compared to the amino acid sequence of a wild-type corn PPO1, the amino acid sequence of the PPO polypeptide has mutations L424S/Y426I at positions corresponding to 424 and 426 of the amino acid sequence of wild-type corn PPO1 protein as set forth in SEQ ID NO: 2; or as compared to the amino acid sequence of a wild-type oilseed rape PPO1, the amino acid sequence of the PPO polypeptide has mutations L424S/Y426I at positions corresponding to 424 and 426 of the amino acid sequence of wild-type oilseed rape PPO1 protein as set forth in SEQ ID NO: 3; or as compared to the amino acid sequence of a wild-type oilseed rape PPO1, the amino acid sequence of the PPO polypeptide has mutations L423S/Y425I at positions corresponding to 423 and 425 of the amino acid sequence of wild-type oilseed rape PPO1 protein as set forth in SEQ ID NO: 4; or as compared to the amino acid sequence of a wild-type peanut PPO1, the amino acid sequence of the PPO polypeptide has mutations L445S/Y447I at positions corresponding to 445 and 447 of the amino acid sequence of wild-type peanut PPO1 protein as set forth in SEQ ID NO: 5; or as compared to the amino acid sequence of a wild-type peanut PPO1, the amino acid sequence of the PPO polypeptide has mutations L439S/Y441I at positions corresponding to 439 and 441 of the amino acid sequence of wild-type peanut PPO1 protein as set forth in SEQ ID NO: 6; or as compared to the amino acid sequence of a wild-type soybean PPO1, the amino acid sequence of the PPO polypeptide has mutations L430S/Y432I at positions corresponding to 430 and 432 of the amino acid sequence of wild-type soybean PPO1 protein as set forth in SEQ ID NO: 7; or as compared to the amino acid sequence of a wild-type sorghum PPO1, the amino acid sequence of the PPO polypeptide has mutations L423S/Y425I at positions corresponding to 423 and 425 of the amino acid sequence of wild-type sorghum PPO1 protein as set forth in SEQ ID NO: 8; or as compared to the amino acid sequence of a wild-type wheat PPO1, the amino acid sequence of the PPO polypeptide has mutations L418S/Y420I at positions corresponding to 418 and 420 of the amino acid sequence of wild-type wheat PPO1 protein as set forth in SEQ ID NO: 9, 10 or 11; or as compared to the amino acid sequence of a wild-type tomato PPO1, the amino acid sequence of the PPO polypeptide has mutations s L445S/Y447I at positions corresponding to 445 and 447 of the amino acid sequence of wild-type tomato PPO1 protein as set forth in SEQ ID NO: 12; or as compared to the amino acid sequence of a wild-type potato PPO1, the amino acid sequence of the PPO polypeptide has mutations L444S/Y446I at positions corresponding to 444 and 446 of the amino acid sequence of wild-type potato PPO1 protein as set forth in SEQ ID NO: 13; or as compared to the amino acid sequence of a wild-type tobacco PPO1, the amino acid sequence of the PPO polypeptide has mutations L440S/Y442I at positions corresponding to 440 and 442 of the amino acid sequence of wild-type tobacco PPO1 protein as set forth in SEQ ID NO: 14; or as compared to the amino acid sequence of a wild-type *Arabidopsis thaliana* PPO1, the amino acid sequence of the PPO polypeptide has mutations L424S/Y426I at positions corresponding to 424 and 426 of the amino acid sequence of wild-type *Arabidopsis thaliana* PPO1 protein as set forth in SEQ ID NO: 15; or as compared to the amino acid sequence of a wild-type upland cotton PPO1, the amino acid sequence of the PPO polypeptide has mutations L426S/Y428I at positions corresponding to 426 and 428 of the amino acid sequence of wild-type upland cotton PPO1 protein as set forth in SEQ ID NO: 16; or as compared to the amino acid sequence of a wild-type radish PPO1, the amino acid sequence of the PPO polypeptide has mutations L425S/Y427I at positions corresponding to 425 and 427 of the amino acid sequence of wild-type radish PPO1 protein as set forth in SEQ ID NO: 17; or as compared to the amino acid sequence of a wild-type foxtail millet PPO1, the amino acid sequence of the PPO polypeptide has mutations L422S/Y424I at positions corresponding to 422 and 424 of the amino acid sequence of wild-type foxtail millet PPO1 protein as set forth in SEQ ID NO: 18; or as compared to the amino acid sequence of a wild-type cabbage PPO1, the amino acid sequence of the PPO polypeptide has mutations L424S/Y426I at positions corresponding to 424 and 426 of the amino acid sequence of wild-type cabbage PPO1 protein as set forth in SEQ ID NO: 19.

2. The PPO polypeptide according to claim 1, wherein the polypeptide has an amino acid sequence as set forth in any one from SEQ ID NO: 26-48.

3. An isolated polynucleotide comprising a nucleic acid sequence selected from:

(1) a nucleic acid sequence encoding the PPO polynucleotide according to claim 1, or a complementary sequence thereof; and (2) a nucleic acid sequence encoding the same amino acid sequence as the sequence shown in (1) due to degeneracy of genetic codes, or a complementary sequence thereof.

4. A plant genome comprising the polynucleotide according to claim 3.

5. A vector construct comprising the polynucleotide according to claim 3 and a homologous or non-homologous promoter operably linked thereto.

6. A host cell comprising the polynucleotide according to claim 3 or a vector construct comprising the polynucleotide.

7. A producing method of a plant cell capable of gaining or improving its tolerance to a PPO inhibitor herbicide, comprising producing the polynucleotide according to claim 3 or a vector construct comprising the polynucleotide in the plant cell by using gene editing methods, or introducing the polynucleotide or the vector construct into the plant cell by using transgenic methods.

8. A producing method of a plant capable of gaining or improving its tolerance to a PPO inhibitor herbicide, comprising regenerating a plant cell into a plant, wherein the plant cell comprises the polynucleotide according to claim 3 or a vector construct comprising the polynucleotide, or the plant cell is produced by the following method: producing the polynucleotide or the vector construct in the plant cell by using gene editing methods, or introducing the polynucleotide or the vector construct into the plant cell by using transgenic methods.

9. A plant produced by the method according to claim 8.

10. A method of enabling a plant to gain or improve tolerance to a PPO inhibitor herbicide, comprising introducing a modification into the gene encoding a protein with PPO activity to produce the PPO polypeptide according to claim 1.

11. A method of gaining or improving the tolerance of a plant cell, plant tissue, plant part or plant to a PPO inhibitor herbicide, comprising expressing the PPO polypeptide according to claim 1 in the plant cell, plant tissue, plant part or plant;

or, comprising hybridizing a plant expressing the PPO polypeptide with another plant, and screening a plant or a part thereof capable of gaining or improving the tolerance to a PPO inhibitor herbicide;

or, comprising gene editing a protein with PPO activity of the plant cell, plant tissue, plant part or plant to achieve expression of the PPO polypeptide.

12. A method for controlling weeds in a plant cultivation site, comprising applying to the cultivation site a herbicidally effective amount of PPO inhibitor herbicide, wherein:

(i) the plant is regenerated from a plant cell, wherein the plant cell comprises a polynucleotide or a vector construct comprising the polynucleotide which comprising a nucleic acid sequence selected from:

(ia) a nucleic acid sequence encoding the PPO polynucleotide according to claim 1, or a complementary sequence thereof; and (ib) a nucleic acid sequence encoding the same amino acid sequence as the sequence shown in (ia) due to degeneracy of genetic codes, or a complementary sequence thereof;

or, (ii) the plant is regenerated from a plant cell wherein the plant cell is produced by the following method: producing the polynucleotide or the vector construct as defined in (i) in the plant cell by using gene editing methods, or introducing the polynucleotide or the vector construct into the plant cell by using transgenic methods:

or, (iii) the plant is produced by introducing a modification into the gene encoding a protein with PPO activity to produce the PPO polypeptide in the plant;

or, (iv) the plant is produced by expressing the PPO polypeptide in the plant;

or, (v) the plant is produced by hybridizing a plant expressing the PPO polypeptide with another plant, and screening a plant or a part thereof capable of gaining or improving the tolerance to a PPO inhibitor herbicide;

or, (vi) the plant is produced by gene editing a protein with PPO activity of the plant to achieve expression of the PPO polypeptide.

13. The method according to claim 12, wherein the PPO inhibitor herbicide is applied in combination with one or more additional herbicides.

14. The plant genome according to claim 4, wherein the plant is a monocotyledonous or dicotyledonous plant.

15. The method according to claim 8, wherein the PPO inhibitor herbicide is one or more compounds selected from a group consisting of pyrimidinediones, diphenyl-ethers, phenylpyrazoles, N-phenylphthalimides, thiadiazoles, oxadiazoles, triazolinones, oxazolidinediones, and others.

16. The isolated polynucleotide according to claim 3, wherein the polynucleotide being a DNA molecule.

17. The host cell according to claim 6, wherein the host cell being a plant cell.

18. The plant genome according to claim 14, wherein the plant is rice (*Oryza sativa* L.), sorghum (*Sorghum bicolor*), wheat (*Triticum aestivum*), barley (*Hordeum vulgare*), foxtail millet (*Setaria italica*), corn (*Zea mays*), sugarcane (*Saccharum officinarum*), *Arabidopsis thaliana*, soybean (*Glycine max*), peanut (*Arachis hypogaea*), tobacco (*Nicotiana tabacum*), cotton (*Gossypium hirsutum*), radish (*Raphanus sativus*), cabbage (*Brassica oleracea*), sweet potato (*Dioscorea esculenta*), yam (*Dioscorea* cayenensis), cassava (*Manihot esculenta*), potato (*Solanum tuberosum*), tomato (*Solanum lycopersicum*), pepper (*Capsicum annuum*), eggplant (*Solanum melongena*), watermelon (*Citrullus lanatus*), squash (*Cucurbita moschata*), cucumber (*Cucumis sativus*), lettuce (*Lactuca sativa*), sesame (*Sesamum indicum*), oilseed rape (*Brassica napus*), sunflower (*Helianthus annuus*), mulberry (*Morus alba*), cowpea (*Vigna unguiculata*), strawberry (*Fragaria ananassa*), apple (*Malus domestica*), peach (*Prunus persica*), cherry (*Prunus* pseudocerasus), apricot (*Prunus armeniaca*), grape vine (*Vitis vinifera*), *papaya* (*Carica papaya*) or alfalfa (*Medicago sativa*).

19. The method according to claim 15, wherein:

(1) the pyrimidinediones include: butafenacil, saflufenacil, benzfendizone, tiafenacil, [3-[2-chloro-4-fluoro-5-(1-methyl-6-trifluoromethyl-2,4-dioxo-1,2,3,4-tetrahydropyrimidin-3-yl) phenoxy]-2-pyridyloxy]acetic acid ethyl ester, 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, 3-[7-chloro-5-fluoro-2-(trifluoromethyl)-1H-benzimidazol-4-yl]-1-methyl-6-(trifluoromethyl)-1H-pyrimidine-2,4-dione, flupropacil, and

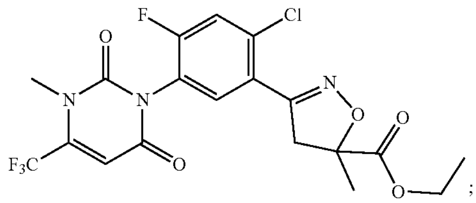 [SMILES: CCOC(=O)C1(C)CC(c2cc(-n3c(=O)cc(C(F)(F)F)n(C)c3=O)c(F)cc2Cl)=NO1];

(2) the diphenyl-ethers include: fomesafen, oxyfluorfen, aclonifen, lactofen, chlomethoxyfen, chlornitrofen, fluoroglycofen-ethyl, acifluorfen or sodium salt thereof, bifenox, ethoxyfen, ethoxyfen-ethyl, fluoronitrofen, furyloxyfen, nitrofluorfen, and halosafen;

(3) the phenylpyrazoles include: pyraflufen-ethyl and fluazolate;

(4) the N-phenylphthalimides include: flumioxazin, cinidon-ethyl, flumipropyn, and flumiclorac-pentyl;

(5) the thiadiazoles include: fluthiacet-methyl, fluthiacet, and thidiazimin;

(6) the oxadiazoles include: oxadiargyl and oxadiazon;

(7) the triazolinones include: carfentrazone, carfentrazone-ethyl, sulfentrazone, azafenidin, and bencarbazone;

(8) the oxazolidinediones include: pentoxazone;

(9) the others include: pyraclonil, flufenpyr-ethyl, profluazol, trifludimoxazin, N-ethyl-3-(2,6-dichloro-4-trifluoromethylphenoxy)-5-methyl-1H-pyrazole-1-carboxamide, N-tetrahydrofurfuryl-3-(2,6-dichloro-4-trifluoromethylphenoxy)-5-methyl-1H-pyrazole-1-carboxamide, N-ethyl-3-(2-chloro-6-fluoro-4-trifluoromethylphenoxy)-5-methyl-1H-pyrazole-1-carboxamide, N-tetrahydrofurfuryl-3-(2-chloro-6-fluoro-4-trifluoromethylphenoxy)-5-methyl-1H-pyrazole-1-carboxamide, 3-[7-fluoro-3-oxo-4-(prop-2-ynyl)-3,4-dihydro-2H-benzo[1,4]oxazin-6-yl]-1,5-dimethyl-6-thioxo[1,3,5]triazinane-2,4-dione, 2-(2,2,7-trifluoro-3-oxo-4-prop-2-ynyl-3,4-dihydro-2H-benzo[1,4]oxazin-6-yl)-4,5,6,7-tetrahydroisoindole-1,3-dione, methyl (E)-4-[2-chloro-5-[4-chloro-5-(difluoromethoxy)-1H-methylpyrazol-3-yl]-4-fluorophenoxy]-3-methoxy-but-2-enoate, phenylpyridines, benzoxazinone derivatives and compounds represented by general formula I

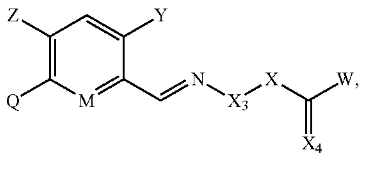

wherein,

Q represents

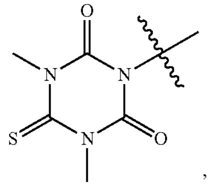,
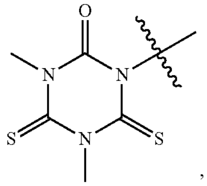,
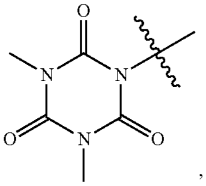,
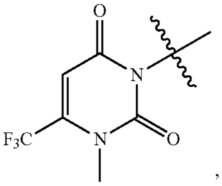,
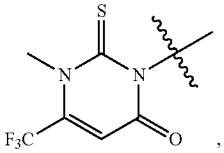,
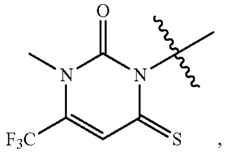,
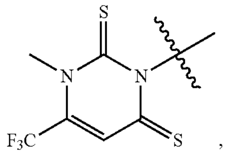,
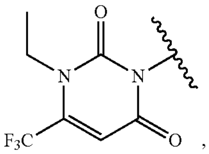,
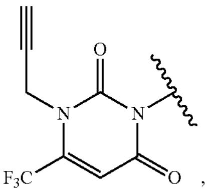,
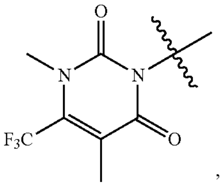,
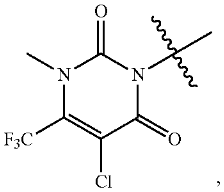,
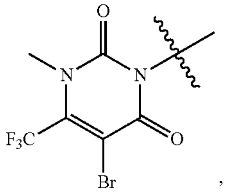,
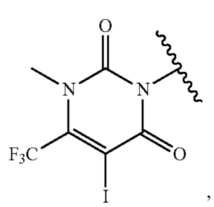,
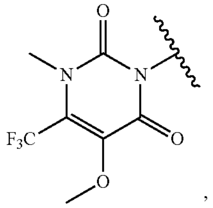, -continued

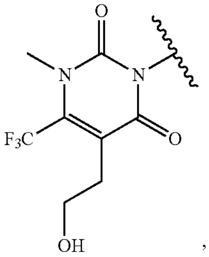,
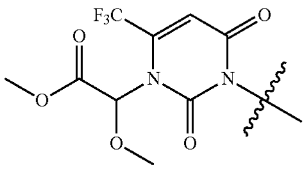 or
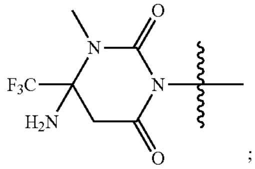;

Y represents halogen, halogenated C1-C6 alkyl or cyano;

Z represents halogen;

M represents CH or N;

X represents —$CX_1X_2$—(C1-C6 alkyl)$_n$—, —(C1-C6 alkyl)-$CX_1X_2$—(C1-C6 alkyl)$_n$— or —$(CH_2)_r$—, n represents 0 or 1, r represents an integer greater than or equal to 2;

$X_1$ and $X_2$ each independently represent hydrogen, halogen, C1-C6 alkyl, C2-C6 alkenyl, C2-C6 alkynyl, halogenated C1-C6 alkyl, halogenated C2-C6 alkenyl, halogenated C2-C6 alkynyl, $C_3$-$C_6$ cycloalkyl, $C_3$-$C_6$ cycloalkyl C1-C6 alkyl, C1-C6 alkoxy, C1-C6 alkylsulphanyl, hydroxy C1-C6 alkyl, C1-C6 alkoxy C1-C6 alkyl, phenyl or benzyl;

$X_3$ and $X_4$ each independently represent O or S;

W represents hydroxyl, C1-C6 alkoxy, C2-C6 alkenyloxy, C2-C6 alkynyloxy, halogenated C1-C6 alkoxy, halogenated C2-C6 alkenyloxy, halogenated C2-C6 alkynyloxy, $C_3$-$C_6$ cycloalkyloxy, phenoxy, sulfydryl, C1-C6 alkylsulphanyl, C2-C6 alkenylsulphanyl, C2-C6 alkynylsulphanyl, halogenated C1-C6 alkylsulphanyl, halogenated C2-C6 alkenylsulphanyl, halogenated C2-C6 alkynylsulphanyl, $C_3$-$C_6$ cycloalkylsulphanyl, phenylsulphanyl, amino or C1-C6 alkylamino.

20. The method according to claim 19, wherein Q represents

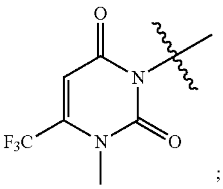 [SMILES: *n1c(=O)cc(C(F)(F)F)n(C)c1=O];

Y represents chlorine; Z represents fluorine; M represents CH; X represents —C*$X_1X_2$—(C1-C6 alkyl)$_n$-, n represents 0; $X_1$ represents hydrogen; $X_2$ represents methyl; $X_3$ and $X_4$ each independently represent O; W represents methoxy; wherein, C* is a chiral center, and the compound is in R configuration.

* * * * *